United States Patent
Acharya

(10) Patent No.: US 12,234,228 B2
(45) Date of Patent: Feb. 25, 2025

(54) NITRIC OXIDE DONOR AND ANTI-OXIDANT COMPOUNDS

(71) Applicant: University of North Texas Health Science Center, Fort Worth, TX (US)

(72) Inventor: Suchismita Acharya, Euless, TX (US)

(73) Assignee: UNIVERSITY OF NORTH TEXAS HEALTH SCIENCE CENTER, Fort Worth, TX (US)

( * ) Notice: Subject to any disclaimer, the term of this patent is extended or adjusted under 35 U.S.C. 154(b) by 855 days.

(21) Appl. No.: 17/416,278

(22) PCT Filed: Dec. 20, 2019

(86) PCT No.: PCT/US2019/067944
§ 371 (c)(1),
(2) Date: Jun. 18, 2021

(87) PCT Pub. No.: WO2020/132496
PCT Pub. Date: Jun. 25, 2020

(65) Prior Publication Data
US 2022/0073503 A1    Mar. 10, 2022

Related U.S. Application Data

(60) Provisional application No. 62/783,333, filed on Dec. 21, 2018.

(51) Int. Cl.
*C07D 413/12* (2006.01)
*A61P 9/10* (2006.01)
*C07D 409/12* (2006.01)

(52) U.S. Cl.
CPC .............. *C07D 413/12* (2013.01); *A61P 9/10* (2018.01); *C07D 409/12* (2013.01)

(58) Field of Classification Search
CPC ........ A61P 9/10; C07D 413/12; C07D 409/12
See application file for complete search history.

(56) References Cited

U.S. PATENT DOCUMENTS

| | | | |
|---|---|---|---|
| 4,405,333 A | 9/1983 | Seemuth | |
| 8,030,440 B1 * | 10/2011 | Willer | C08G 65/22 528/417 |
| 2008/0233163 A1 | 9/2008 | Assaf | |
| 2014/0179936 A1 | 6/2014 | Pienaar et al. | |

OTHER PUBLICATIONS

Ouellette, R. J., Bertsch, R. J., J. Org. Chem., vol. 41, No. 16, 1976. (Year: 1976).*
Morris, G., et al. Journal of Pharmaceutical Sciences. vol. 80, No. 2, 1991. (Year: 1991).*
De Jong, W. H., Borm, P. J. A., Int. J. Nanomedicine. 2008:3(2) 133-149. (Year: 2008).*
Jiang, S., et al. Brain Circulation. 2020, 6(4), 248-253. (Year: 2020).*
Acharya et al., "Design and synthesis of novel hybrid sydnonimine and prodrug useful for glaucomatous optic neuropathy", *Bioorg. Med. Chem. Lett.*, 26:1490-1494, 2016.
Chen et al., "Efficacy of intravenous tissue-type plasminogen activator in central retinal artery occlusion: report from a randomized, controlled trial." *Stroke*, 42(8): 2229-2234, 2011.
Chiueh et al., "Neuroprotective properties of Nitric oxide", *Annals of the New York Academy of Science*, 215:113-116, 1999.
De Jong et al., Drug delivery and nanoparticles: applications and hazards, *International journal of nanomedicine*, 3:133-149, 2008.
De Leur et al., "Treatment for critical lower limb ischemia in elderly patients", *World J. Surg.*, 36(12):2937-2943, 2012.
Dua et al., "Epidemiology of Peripheral Arterial Disease and Critical Limb Ischemia", *Tech Vasc Interv Radiol*, 19:91-95, 2016.

(Continued)

*Primary Examiner* — Eric Olson
*Assistant Examiner* — Samuel L Galster
(74) *Attorney, Agent, or Firm* — Parker Highlander PLLC

(57) ABSTRACT

In some aspects, the present disclosure provides compounds of the formulae: (A), (B), (III), and/or (IV), wherein the variables are as defined herein. Pharmaceutical compositions of the compounds are also provided. In some aspects, the compounds or compositions of the present disclosure may be used for the treatment of diseases or disorders, such as eye diseases and peripheral arterial diseases such as hind limb ischemia.

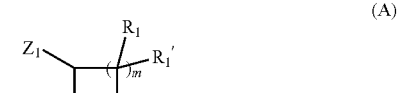

(A)

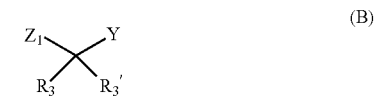

(B)

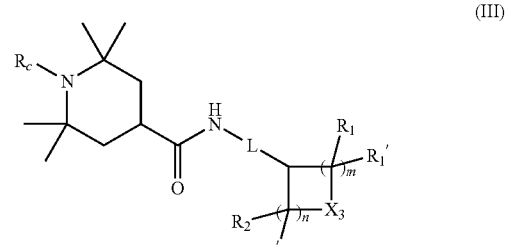

(III)

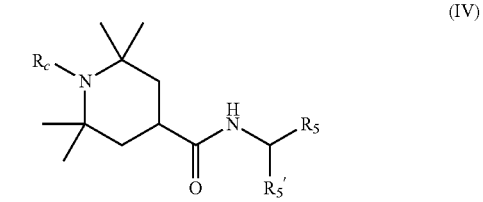

(IV)

78 Claims, 12 Drawing Sheets

(56) References Cited

OTHER PUBLICATIONS

Gasco et al., "Focus on recent approaches for the development of new NO-donors", *Mini-Reviews in Medicinal Chemistry*, 5:217-229, 2005.

Grochot-Przeczek et al., "Therapeutic angiogenesis for revascularization in peripheral artery disease", *Gene*, 525:220-228, 2013.

Inglez et al., J.C.D. in Vascular Diseases for the Non-Specialist. (eds. T.P. Navarro, A. Dardik, D. Junqueira & L. Cisneros) 233-251 (Springer International Publishing, Cham; 2017).

Jude et al., "Peripheral arterial disease in diabetes—a review", *Diabet. Med.*, 27:4-14, 2010.

Kullo et al., "Peripheral Artery Disease", *N. Engl. J. Med.*, 374:861-871, 2016.

LaVan et al., "Small-scale systems for in vivo drug delivery", *Nat. Biotechnol.*, 21:1184, 2003.

Le et al., "Hybrid Nitric Oxide Donor and its Carrier for the Treatment of Peripheral Arterial Diseases." *Sci Rep.*, 7(1): 8692. 2017.

Magee et al., "Cancer Stem Cells: Impact, Heterogeneity, and Uncertainty", *Cancer Cell*, 21:283-296, 2012.

Mayo et al., "Nitrative stress in cerebral endothelium is mediated by mGluR5 in hyperhomocysteinemia." *J Cereb Blood Flow Metab*, 32(5): 825-834. 2012.

Miller et al., "Recent developments in nitric oxide donor drugs", *British Journal of Pharmacology*, 15:, 305-321, 2007.

Nguyen et al., "Arginase Inhibition Restores Peroxynitrite-Induced Endothelial Dysfunction via L-Arginine-Dependent Endothelial Nitric Oxide Synthase Phosphorylation." *Yonsei Med J.*, 57(6): 1329-1338. 2016.

Ouriel et al., "Peripheral arterial disease", *The Lancet*, 358:1257-1264, 2001.

Patel et al., "Dexamethasone-Induced Ocular Hypertension in Mice: Effects of Myocilin and Route of Administration", *The American Journal of Pathology*, 187(4): 713-723, 2017.

Platt et al., "Peroxynitrite increases VEGF expression in vascular endothelial cells via STAT3", *Free Radicals in Biology and Medicine*, 39(10):1353-1361, 2005.

Remessy et al., "Oxidative stress inactives VEGF survival signaling in retinal endothelial cells via PI 3-kinase tyrosine nitration", *Journal of Cell Science*, 118(Pt 1), 243-252, 2005.

Sadowska-Bartosz et al. "Nitroxides protect against peroxynitrite-induced nitration and oxidation." *Free Radic. Biol. Med.*, 89: 1165-1175. 2015.

Steyers et al., "Endothelial dysfunction in chronic inflammatory diseases", *Int. J. Mol. Sci.*, 15:11324-11349, 2014.

Sun et al., "Alterations in photoreceptor-bipolar cell signaling following ischemia/reperfusion in the rat retina", *J. Comparative Neurol.*, 505(1): 131-146, 2007.

Thukkani et al., "Endovascular intervention for peripheral artery disease", *Circ. Res.*, 116:1599-1613, 2015.

Toda et al., "Nitric oxide: Ocular blood flow, glaucoma, and diabetic retinopathy", *Progress in Retinal and Eye Research*, 26:205-238, 2007.

Weiss et al., "Stem Cells, Cell Therapies, and Bioengineering in Lung Biology and Diseases", *Comprehensive Review of the Recent Literature 2010-2012.*, 10:S45-S97, 2013.

Whitehill et al., "Role of revascularization in the treatment of claudication", *Vasc. Med.*, 2(3):252-256, 1997.

Wolfram et al., "Safety of Nanoparticles in Medicine", *Curr. Drug Targets*, 16:1671-1681, 2015.

\* cited by examiner

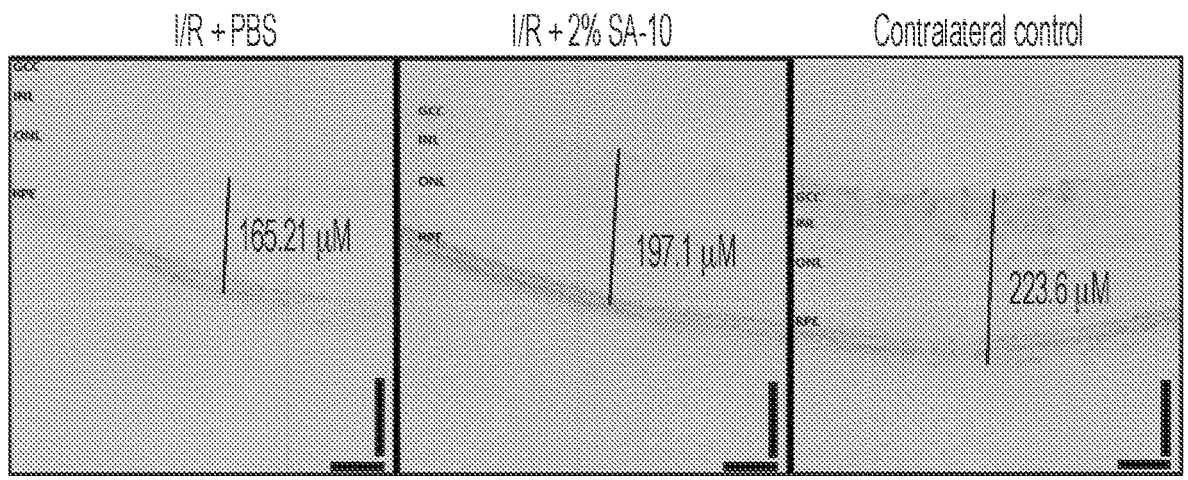
FIG. 9D
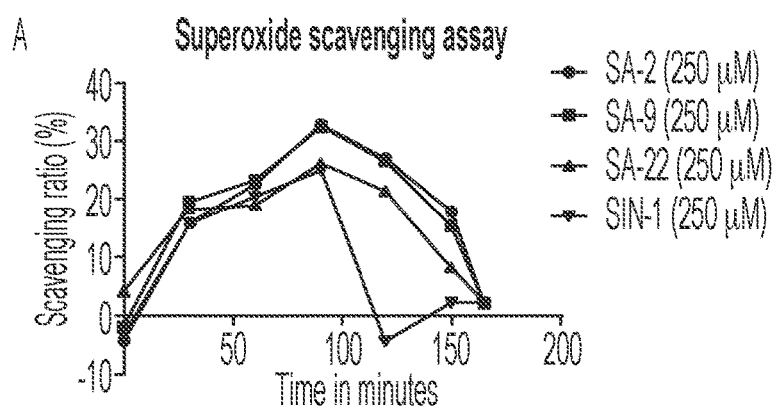
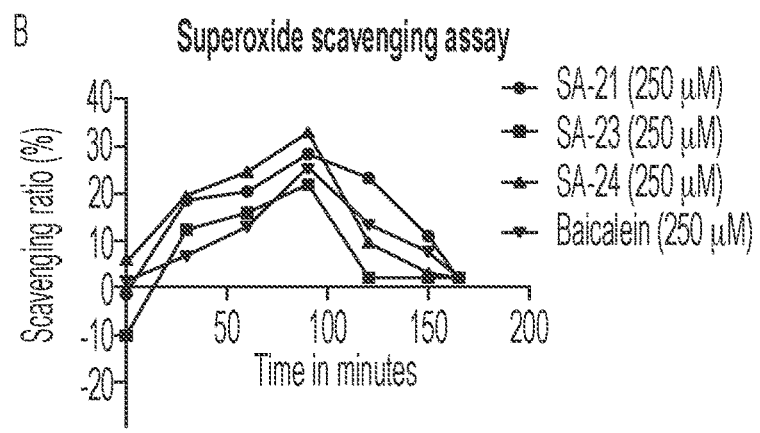
FIGS. 10A - 10B

NITRIC OXIDE DONOR AND ANTI-OXIDANT COMPOUNDS

PRIORITY CLAIM

This application is a national phase application under 35 U.S.C. § 371 of International Application No. PCT/US2019/067944, filed Dec. 20, 2019, which claims benefit of priority to U.S. Provisional Application Ser. No. 62/783,333, filed Dec. 21, 2018, the entire contents of each of which are hereby incorporated by reference.

BACKGROUND OF THE DISCLOSURE

I. Field of the Disclosure

The present disclosure relates generally to the fields of biology, chemistry, and medicine. More particularly, it concerns compounds, compositions and methods for the treatment and prevention of diseases and disorders, such ischemic neuropathy, glaucoma, fibrosis, hindlimb ischemia, ischemic stroke, acute respiratory distress syndrome, and bronchopulmonary dysplasia.

II. Description of Related Art

Nitric oxide (NO) derived from endothelium and efferent nitrergic neurons has been reported to regulate ocular blood flow, with endothelial dysfunction due to increased production of reactive oxygen species (ROS) impairing ocular hemodynamics. In particular, enhanced superoxide production may reduce NO bioavailability by converting it to the toxic ROS peroxynitrite (Toda et al., 2007). Diabetic retinopathy (DR), age related macular degeneration (AMD), and glaucomatous optic neuropathy are all associated with enhanced oxidative stress. Inhibition of oxidative stress-induced nitric oxide destruction was hypothesized to allow preservation of nitric oxide's neuroprotective role (Chiou, 1999).

Early development of nitric oxide tolerance is a major drawback in NO-donor based therapies. Moreover, several recent reports indicate superoxide as having a significant role in mediation of such tolerance (Griendling et al., 1994).

During peripheral arterial disease, ischemic events induce oxidative stress resulting in EC dysfunction via decreased activity of antioxidant enzymes in mitochondria. Such events of mitochondrial dysfunction and production of superoxide diminish the NO bioavailability by reacting with NO and forming toxic ONOO·⁻ that further damages DNA, lipids and proteins (Mayo et al., 2012). ROS and ONOO·⁻ specifically dysfunctionalize ECs and increase the endo-exogenous NO imbalance. Consequently, there may be a loop where excessive NO produces more stress of ROS on ECs. Therefore, besides balancing NO levels, it is also crucial to regulate ROS levels under ischemic conditions. As such, these is a need for compounds that can act as both NO donors as well as neutralize ROS.

SUMMARY

The present disclosure provides thiol-containing antioxidants and nitric oxide donors with therapeutic properties, pharmaceutical compositions thereof, and methods for their use.

In some aspects, the present disclosure provides compounds of the formula:

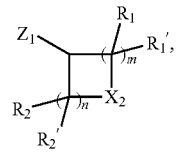

wherein:
n and m are each independently 0, 1, 2, 3, or 4;
$Z_1$ is —$ONO_2$; or
—O-alkanediyl$_{(C \leq 12)}$-$NO_2$, substituted —O-alkanediyl$_{(C \leq 12)}$-$NO_2$, -alkanediyl$_{(C \leq 12)}$-$NO_2$, or substituted -alkanediyl$_{(C \leq 12)}$-$NO_2$; or
a group of the formula:

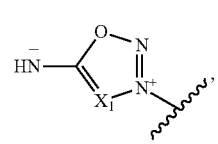

wherein:
$X_1$ is =$CR_{x1}$— or =N— wherein,
$R_{x1}$ is hydrogen, alkyl$_{(C \leq 12)}$, or substituted alkyl$_{(C \leq 12)}$;
$X_2$ is —O—, —S—, —S(O)—, or —S(O)$_2$—;
each instance of $R_1$, $R_1'$, $R_2$, and $R_2'$ is independently hydrogen, hydroxy, amino, nitro, cyano, halo, carboxyl, carbamoyl, mercapto, —S(O)$_2$OH, or —S(O)$_2$NH$_2$; or
alkyl$_{(C \leq 12)}$, acyl$_{(C \leq 12)}$, alkoxy$_{(C \leq 12)}$, alkylamino$_{(C \leq 12)}$, dialkylamino$_{(C \leq 12)}$, amido$_{(C \leq 12)}$, acyloxy$_{(C \leq 12)}$, or a substituted version of any of these groups; or —C(O)$R_b$, wherein:
$R_b$ alkoxy$_{(C \leq 12)}$, alkylamino$_{(C \leq 12)}$, or dialkylamino$_{(C \leq 12)}$; or
provided the sum of n and m is 1, 2, 3, 4, 5, or 6; or
a compound of the formula:

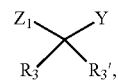

wherein:
$Z_1$ is as defined above;
$R_3$ is alkyl$_{(C2-12)}$, aralkyl$_{(C \leq 12)}$, heteroaralkyl$_{(C \leq 12)}$, -alkanediyl$_{(C \leq 12)}$-NHC(NH)NH$_2$, or a substituted version of any of these groups;
$R_3'$ is hydrogen; or
$R_3$ and $R_3'$ are taken together and are -alkanediyl$_{(C \leq 12)}$-$X_3$—, substituted -alkanediyl$_{(C \leq 12)}$-$X_3$—, -alkanediyl$_{(C \leq 6)}$-$X_3$-alkanediyl$_{(C \leq 6)}$-, or substituted -alkanediyl$_{(C \leq 6)}$-$X_3$-alkanediyl$_{(C \leq 6)}$-, wherein:
$X_3$ is —O—, —$NR_a$—, —S—, —S(O)—, or —S(O)$_2$—, wherein:
$R_a$ is hydrogen, hydroxy, or oxyl radical; or
alkyl$_{(C \leq 12)}$, aralkyl$_{(C \leq 12)}$, acyl$_{(C \leq 12)}$, or a substituted version of any of these groups; or a group of the formula:

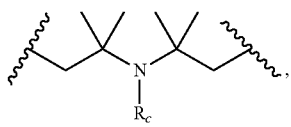
(IIa)

wherein:
$R_c$ is hydroxy or oxyl radical; and
Y is —$CO_2R_d$, or —$C(O)NR_dR_e$, wherein:
$R_d$ is hydrogen; or
alkyl$_{(C\leq12)}$, cycloalkyl$_{(C\leq12)}$, heterocycloalkyl$_{(C\leq12)}$, aralkyl$_{(C\leq12)}$, aryl$_{(C\leq12)}$, heteroaralkyl$_{(C\leq12)}$, heteroaryl$_{(C\leq12)}$, or a substituted version of any of these groups; or
a group of the formula:

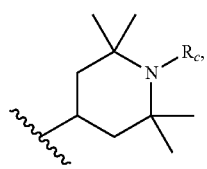
(IIb)

wherein $R_c$ is as defined above; or
a group of the formula:

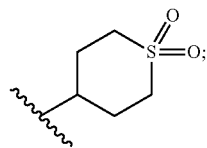
(IIc)

$R_e$ is hydrogen, alkyl$_{(C\leq12)}$, or substituted alkyl$_{(C\leq12)}$; or
a compound of the formula:

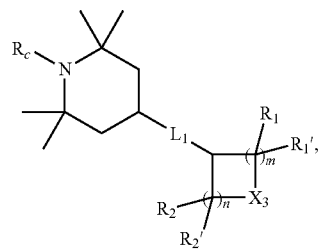
(III)

wherein:
n, m, $X_3$, $R_1$, $R_1'$, $R_2$, $R_2'$, and $R_c$ are as defined above; and
$L_1$ is
a group of the formula:

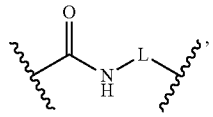
(IIIb)

wherein:
L is a covalent bond; or
a group of the formula:

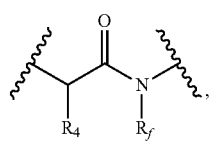
(IIIa)

wherein:
$R_f$ is hydrogen, alkyl$_{(C\leq12)}$, or substituted alkyl$_{(C\leq12)}$;
$R_4$ is hydrogen; or
alkyl$_{(C\leq12)}$, aralkyl$_{(C\leq12)}$, heteroaralkyl$_{(C\leq12)}$, -alkanediyl$_{(C\leq12)}$-$ONO_2$, or a substituted version of any of these groups;
provided the sum of n and m is 1, 2, 3, 4, 5, or 6; or
a compound of the formula:

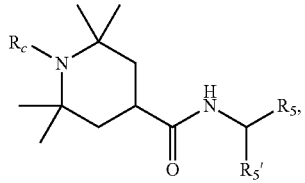
(IV)

wherein:
$R_c$ is as defined above;
$R_5$ is —$CH_2OR_g$, —$CO_2R_g$, or —$C(O)NR_hR_i$, wherein:
$R_g$ is hydrogen; or
alkyl$_{(C\leq12)}$, substituted alkyl$_{(C\leq12)}$, cycloalkyl$_{(C\leq12)}$, or substituted cycloalkyl$_{(C\leq12)}$;
$R_h$ and $R_i$ are each independently hydrogen; or
alkyl$_{(C\leq12)}$, substituted alkyl$_{(C\leq12)}$, cycloalkyl$_{(C\leq12)}$, or substituted cycloalkyl$_{(C\leq12)}$; and
$R_5'$ is hydrogen; or
alkyl$_{(C\leq12)}$, aralkyl$_{(C\leq12)}$, heteroaralkyl$_{(C\leq12)}$, or a substituted version of any of these groups;
or a pharmaceutically acceptable salt of any of these formulae.

In some embodiments, the compounds are further defined as:

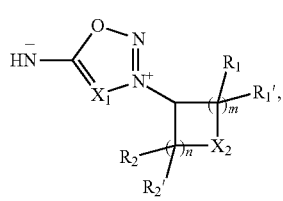
(I)

wherein:
n and m are each independently 0, 1, 2, 3, or 4;
$X_1$ is =CH— or =N—;
$X_2$ is —O—, —S—, —S(O)—, or —S(O)$_2$—;
each instance of $R_1$, $R_1'$, $R_2$, and $R_2'$ is independently hydrogen, hydroxy, amino, nitro, cyano, halo, carboxyl, carbamoyl, mercapto, —S(O)$_2$OH, or —S(O)$_2$NH$_2$; or alkyl$_{(C\leq12)}$, acyl$_{(C\leq12)}$, alkoxy$_{(C\leq12)}$, alkylamino$_{(C\leq12)}$, dialkylamino$_{(C\leq12)}$, amido$_{(C\leq12)}$, acyloxy$_{(C\leq12)}$, or a substituted version of any of these groups; or —C(O)$R_b$, wherein:
$R_b$ alkoxy$_{(C\leq12)}$, alkylamino$_{(C\leq12)}$, or dialkylamino$_{(C\leq12)}$; or
provided the sum of n and m is 1, 2, 3, 4, 5, or 6; or
a compound of the formula:

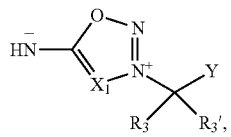

(II)

wherein:
$X_1$ is as defined above;
$R_3$ is alkyl$_{(C2-12)}$, aralkyl$_{(C\leq12)}$, heteroaralkyl$_{(C\leq12)}$, -alkanediyl$_{(C\leq12)}$-NHC(NH)NH$_2$, or a substituted version of any of these groups;
$R_3'$ is hydrogen; or
$R_3$ and $R_3'$ are taken together and are -alkanediyl$_{(C\leq12)}$-$X_3$—, substituted -alkanediyl$_{(C\leq12)}$-$X_3$—, -alkanediyl$_{(C\leq6)}$-$X_3$-alkanediyl$_{(C\leq6)}$-, or substituted -alkanediyl$_{(C\leq6)}$-$X_3$-alkanediyl$_{(C\leq6)}$-, wherein:
$X_3$ is —O—, —NR$_a$—, —S—, —S(O)—, or —S(O)$_2$—, wherein:
$R_a$ is hydrogen, hydroxy, or oxyl radical; or alkyl$_{(C\leq12)}$, aralkyl$_{(C\leq12)}$, acyl$_{(C\leq12)}$, or a substituted version of any of these groups; or
a group of the formula:

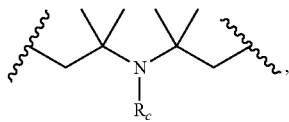

(IIa)

wherein:
$R_c$ is hydroxy or oxyl radical; and
Y is —CO$_2$R$_d$, or —C(O)NR$_d$R$_e$, wherein:
$R_d$ is hydrogen; or
alkyl$_{(C\leq12)}$, cycloalkyl$_{(C\leq12)}$, heterocycloalkyl$_{(C\leq12)}$, aralkyl$_{(C\leq12)}$, aryl$_{(C\leq12)}$, heteroaralkyl$_{(C\leq12)}$, heteroaryl$_{(C\leq12)}$, or a substituted version of any of these groups; or
a group of the formula:

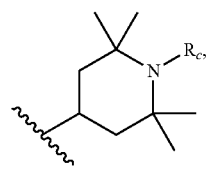

(IIb)

wherein $R_e$ is as defined above; or
a group of the formula:

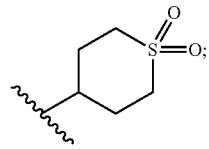

(IIc)

$R_e$ is hydrogen, alkyl$_{(C\leq12)}$, or substituted alkyl$_{(C\leq12)}$; or
a compound of the formula:

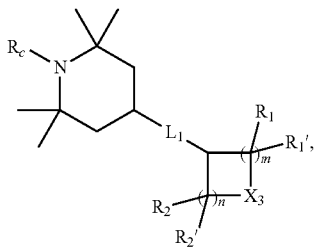

(III)

wherein:
n, m, $X_3$, $R_1$, $R_1'$, $R_2$, $R_2'$, and $R_c$ are as defined above; and
$L_1$ is
a group of the formula:

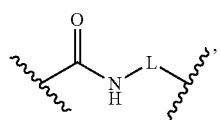

(IIIb)

wherein:
L is a covalent bond; or
a group of the formula:

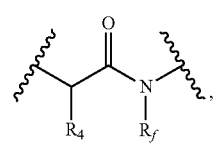

(IIIa)

wherein:
$R_f$ is hydrogen, alkyl$_{(C\leq12)}$, or substituted alkyl$_{(C\leq12)}$;
$R_4$ is hydrogen; or
alkyl$_{(C\leq12)}$, aralkyl$_{(C\leq12)}$, heteroaralkyl$_{(C\leq12)}$, -alkanediyl$_{(C\leq12)}$-ONO$_2$, or a substituted version of any of these groups;
provided the sum of n and m is 1, 2, 3, 4, 5, or 6; or a compound of the formula:

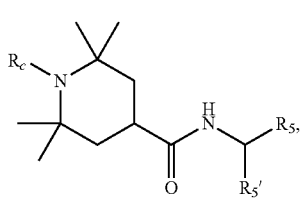
(IV)

wherein:
  $R_c$ is as defined above;
  $R_5$ is —CH$_2$OR$_g$, —CO$_2$R$_g$, or —C(O)NR$_h$R$_i$, wherein:
    $R_g$ is hydrogen; or
      alkyl$_{(C \leq 12)}$, substituted alkyl$_{(C \leq 12)}$, cycloalkyl$_{(C \leq 12)}$, or substituted cycloalkyl$_{(C \leq 12)}$;
    $R_h$ and $R_i$ are each independently hydrogen; or
      alkyl$_{(C \leq 12)}$, substituted alkyl$_{(C \leq 12)}$, cycloalkyl$_{(C \leq 12)}$, or substituted cycloalkyl$_{(C \leq 12)}$; and
  $R_5'$ is hydrogen; or
    alkyl$_{(C \leq 12)}$, aralkyl$_{(C \leq 12)}$, heteroaralkyl$_{(C \leq 12)}$, or a substituted version of any of these groups;
or a pharmaceutically acceptable salt of any of these formulae.

In some embodiments, Y is a group of the formula:

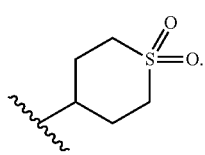
(IIc)

In some embodiments, the compounds are further defined:

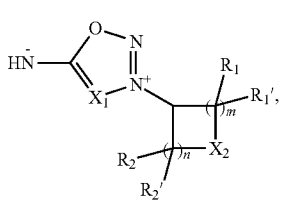
(I)

wherein:
  n and m are each independently 0, 1, 2, 3, or 4;
  $X_1$ is =CH— or =N—;
  $X_2$ is —O—, —S—, —S(O)—, or —S(O)$_2$—;
  each instance of $R_1$, $R_1'$, $R_2$, and $R_2'$ is independently hydrogen, hydroxy, amino, nitro, cyano, halo, carboxyl, carbamoyl, mercapto, —S(O)$_2$OH, —S(O)$_2$NH$_2$, alkyl$_{(C \leq 12)}$, acyl$_{(C \leq 12)}$, alkoxy$_{(C \leq 12)}$, alkylamino$_{(C \leq 12)}$, dialkylamino$_{(C \leq 12)}$, amido$_{(C \leq 12)}$, or acyloxy$_{(C \leq 12)}$, or —C(O)R$_b$, wherein:
    $R_b$ alkoxy$_{(C \leq 12)}$, alkylamino$_{(C \leq 12)}$, or dialkylamino$_{(C \leq 12)}$; or
provided the sum of n and m is 1, 2, 3, 4, 5, or 6; or a compound of the formula:

(II)

wherein:
  $X_1$ is as defined above;
  $R_3$ is alkyl$_{(C2-12)}$, substituted alkyl$_{(C \leq 12)}$, aralkyl$_{(C \leq 12)}$, substituted aralkyl$_{(C \leq 12)}$, heteroaralkyl$_{(C \leq 12)}$, or -alkanediyl$_{(C \leq 12)}$-NHC(NH)NH$_2$;
  $R_3'$ is hydrogen; or
  $R_3$ and $R_3'$ are taken together and are -alkanediyl$_{(C \leq 12)}$-X$_3$—, substituted -alkanediyl$_{(C \leq 12)}$-X$_3$—, -alkanediyl$_{(C \leq 6)}$-X$_3$-alkanediyl$_{(C \leq 6)}$-, or substituted -alkanediyl$_{(C \leq 6)}$-X$_3$-alkanediyl$_{(C \leq 6)}$-, wherein:
    $X_3$ is —O—, —NR$_a$—, —S—, —S(O)—, or —S(O)$_2$—, wherein:
      $R_a$ is hydrogen, hydroxy, or oxyl radical; or
        alkyl$_{(C \leq 12)}$, aralkyl$_{(C \leq 12)}$, acyl$_{(C \leq 12)}$, or a substituted version of any of these groups; or
    a group of the formula:

(IIa)

wherein:
  $R_c$ is hydroxy or oxyl radical; and
  Y is —CO$_2$R$_d$ or —C(O)NR$_d$R$_e$, wherein:
    $R_d$ is hydrogen; or
      alkyl$_{(C \leq 12)}$, cycloalkyl$_{(C \leq 12)}$, heterocycloalkyl$_{(C \leq 12)}$, aralkyl$_{(C \leq 12)}$, aryl$_{(C \leq 12)}$, heteroaralkyl$_{(C \leq 12)}$, heteroaryl$_{(C \leq 12)}$, or a substituted version of any of these groups; or
    a group of the formula:

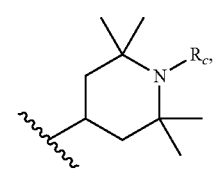
(IIb)

wherein $R_c$ is as defined above;
$R_e$ is hydrogen, alkyl$_{(C \leq 12)}$, or substituted alkyl$_{(C \leq 12)}$; or a compound of the formula:

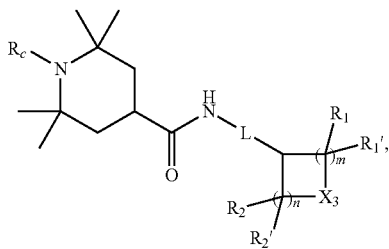
(III)

wherein:
n, m, $X_3$, $R_1$, $R_1'$, $R_2$, $R_2'$, and $R_c$ are as defined above; and
L is a covalent bond; or
a group of the formula:

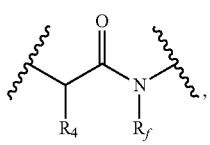
(IIIa)

wherein:
$R_f$ is hydrogen, alkyl$_{(C \leq 12)}$, or substituted alkyl$_{(C \leq 12)}$;
$R_4$ is hydrogen; or
alkyl$_{(C \leq 12)}$, aralkyl$_{(C \leq 12)}$, heteroaralkyl$_{(C \leq 12)}$, or a substituted version of any of these groups;
provided the sum of n and m is 1, 2, 3, 4, 5, or 6; or
a compound of the formula:

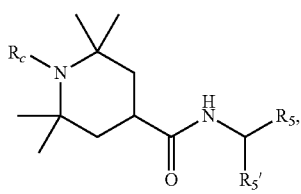
(IV)

wherein:
$R_c$ is as defined above;
$R_5$ is —CH$_2$OR$_g$, —CO$_2$R$_g$, or —C(O)NR$_h$R$_i$, wherein:
$R_g$ is hydrogen; or
alkyl$_{(C \leq 12)}$, substituted alkyl$_{(C \leq 12)}$, cycloalkyl$_{(C \leq 12)}$, or substituted cycloalkyl$_{(C \leq 12)}$;
$R_h$ and $R_i$ are each independently hydrogen; or
alkyl$_{(C \leq 12)}$, substituted alkyl$_{(C \leq 12)}$, cycloalkyl$_{(C \leq 12)}$, or substituted cycloalkyl$_{(C \leq 12)}$; and
$R_5'$ is hydrogen; or
alkyl$_{(C \leq 12)}$, aralkyl$_{(C \leq 12)}$, heteroaralkyl$_{(C \leq 12)}$, or a substituted version of any of these groups;
or a pharmaceutically acceptable salt of any of these formulae.
In some embodiments, the compound is a compound of formula (I).

In some embodiments, the compound is further defined as:

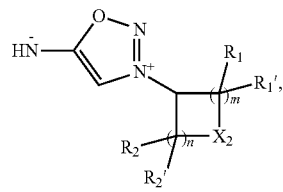
(V)

wherein:
n and m are each independently 0, 1, 2, 3, or 4;
$X_2$ is —O—, —S—, —S(O)—, or —S(O)$_2$—; and
each instance of $R_1$, $R_1'$, $R_2$, and $R_2'$ is independently hydrogen, hydroxy, amino, nitro, cyano, halo, carboxyl, carbamoyl, mercapto, —S(O)$_2$OH, —S(O)$_2$NH$_2$, alkyl$_{(C \leq 12)}$, acyl$_{(C \leq 12)}$, alkoxy$_{(C \leq 12)}$, alkylamino$_{(C \leq 12)}$, dialkylamino$_{(C \leq 12)}$, amido$_{(C \leq 12)}$, or acyloxy$_{(C \leq 12)}$, or —C(O)R$_b$, wherein:
$R_b$ alkoxy$_{(C \leq 12)}$, alkylamino$_{(C \leq 12)}$, or dialkylamino$_{(C \leq 12)}$;
provided the sum of n and m is 1, 2, 3, 4, 5, or 6;
or a pharmaceutically acceptable salt thereof.
In some embodiments, the compound is further defined as:

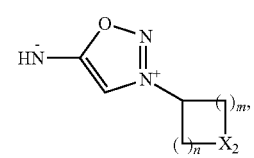
(VI)

wherein:
n and m are each independently 0, 1, 2, 3, or 4; and
$X_2$ is —O—, —S—, —S(O)—, or —S(O)$_2$;
provided the sum of n and m is 1, 2, 3, 4, 5, or 6;
or a pharmaceutically acceptable salt thereof.
In some embodiments, the compound is further defined as:

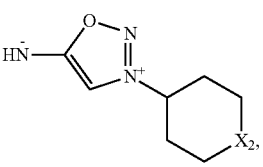
(VII)

wherein:
$X_2$ is —O—, —S—, —S(O)—, or —S(O)$_2$;
or a pharmaceutically acceptable salt thereof.
In some embodiments, $X_2$ is —S—, —S(O)—, or —S(O)$_2$—.
In some embodiments, the compound is a compound of formula (II).

In some embodiments, the compound is further defined as:

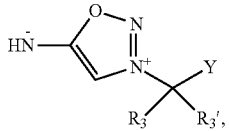
(VIII)

wherein:
R$_3$ is alkyl$_{(C2-12)}$, substituted alkyl$_{(C≤12)}$, aralkyl$_{(C≤12)}$, substituted aralkyl$_{(C≤12)}$, heteroaralkyl$_{(C≤12)}$, or -alkanediyl$_{(C≤12)}$-NHC(NH)NH$_2$;
R$_3$' is hydrogen; or
R$_3$ and R$_3$' are taken together and are -alkanediyl$_{(C≤12)}$-X$_3$—, substituted -alkanediyl$_{(C≤12)}$-X$_3$—, -alkanediyl$_{(C≤6)}$-X$_3$-alkanediyl$_{(C≤6)}$-, or substituted -alkanediyl$_{(C≤6)}$-X$_3$-alkanediyl$_{(C≤6)}$-, wherein:
X$_3$ is —O—, —NR$_a$—, —S—, —S(O)—, or —S(O)$_2$—, wherein:
R$_a$ is hydrogen, hydroxy, or oxyl radical; or alkyl$_{(C≤12)}$, aralkyl$_{(C≤12)}$, acyl$_{(C≤12)}$, or a substituted version of any of these groups; or
a group of the formula:

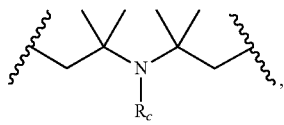
(IIa)

wherein:
R$_c$ is hydroxy or oxyl radical; and
Y is —CO$_2$R$_d$, or —C(O)NR$_d$R$_e$, wherein:
R$_d$ is hydrogen; or
alkyl$_{(C≤12)}$, cycloalkyl$_{(C≤12)}$, heterocycloalkyl$_{(C≤12)}$, aralkyl$_{(C≤12)}$, aryl$_{(C≤12)}$, heteroaralkyl$_{(C≤12)}$, heteroaryl$_{(C≤12)}$, or a substituted version of any of these groups; or
a group of the formula:

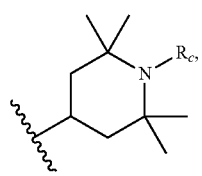
(IIb)

wherein R$_c$ is hydroxy or oxyl radical;
R$_e$ is hydrogen, alkyl$_{(C≤12)}$, or substituted alkyl$_{(C≤12)}$;
or a pharmaceutically acceptable salt thereof.
In some embodiments, the compound is further defined as:

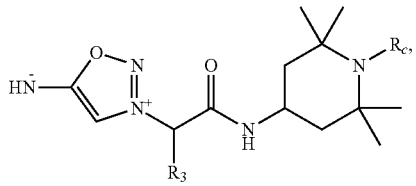
(IX)

wherein:
R$_3$ is alkyl$_{(C2-12)}$, substituted alkyl$_{(C≤12)}$, aralkyl$_{(C≤12)}$, substituted aralkyl$_{(C≤12)}$, heteroaralkyl$_{(C≤12)}$, or -alkanediyl$_{(C≤12)}$-NHC(NH)NH$_2$; and
R$_c$ is hydroxy or oxyl radical;
or a pharmaceutically acceptable salt thereof.

In some embodiments, R$_3$ is alkyl$_{(C2-12)}$ or substituted alkyl$_{(C≤12)}$. In further embodiments, R$_3$ is substituted alkyl$_{(C≤12)}$, such as —CH$_2$CH$_2$SCH$_3$. In other embodiments, R$_3$ is aralkyl$_{(C≤2)}$ substituted aralkyl$_{(C≤12)}$. In further embodiments, R$_3$ is aralkyl$_{(C≤12)}$, such as benzyl. In other embodiments, R$_3$ is substituted aralkyl$_{(C≤12)}$, such asp-hydroxybenzyl. In some embodiments, R$_c$ is hydroxy. In other embodiments, R$_c$ is oxyl radical.

In some embodiments, the compound is a compound of formula (III). In some embodiments, L$_1$ is a group of the formula:

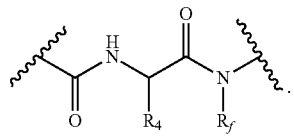

In some embodiments, the compound is further defined as:

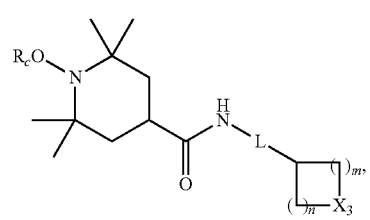
(XII)

wherein:
n and m are each independently 0, 1, 2, 3, or 4;
X$_3$ is —O—, —NR$_a$—, —S—, —S(O)—, or —S(O)$_2$—, wherein:
R$_a$ is hydrogen, hydroxy, or oxyl radical; or alkyl$_{(C≤12)}$, aralkyl$_{(C≤12)}$, acyl$_{(C≤12)}$, or a substituted version of any of these groups;
R$_c$ is hydroxy or oxyl radical; and
R$_4$ is hydrogen; or
alkyl$_{(C≤12)}$, aralkyl$_{(C≤12)}$, heteroaralkyl$_{(C≤12)}$, -alkanediyl$_{(C≤12)}$-ONO$_2$, or a substituted version of any of these groups;
provided the sum of n and m is 1, 2, 3, 4, 5, or 6;
or a pharmaceutically acceptable salt thereof.
In some embodiments, the compound is further defined as:

(X)

wherein:
n and m are each independently 0, 1, 2, 3, or 4;
$X_3$ is —O—, —$NR_a$—, —S—, —S(O)—, or —$S(O)_2$—,
wherein:
$R_a$ is hydrogen, hydroxy, or oxyl radical; or
alkyl$_{(C≤12)}$, aralkyl$_{(C≤12)}$, acyl$_{(C≤12)}$, or a substituted version of any of these groups; $R_c$ is hydroxy or oxyl radical; and
L is a covalent bond; or
a group of the formula:

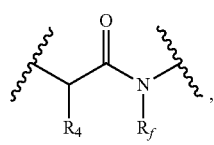

(IIIa)

wherein:
$R_f$ is hydrogen, alkyl$_{(C≤12)}$, or substituted alkyl$_{(C≤12)}$;
$R_4$ is hydrogen; or
alkyl$_{(C≤12)}$, aralkyl$_{(C≤12)}$, heteroaralkyl$_{(C≤12)}$, or a substituted version of any of these groups;
provided the sum of n and m is 1, 2, 3, 4, 5, or 6;
or a pharmaceutically acceptable salt thereof.

In some embodiments, the compound is further defined as:

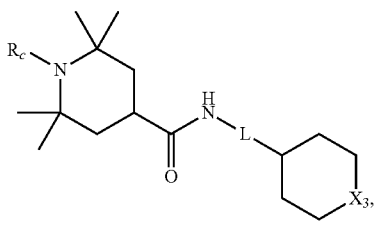

(XI)

wherein:
$X_3$ is —O—, —$NR_a$—, —S—, —S(O)—, or —$S(O)_2$—,
wherein:
$R_a$ is hydrogen, hydroxy, or oxyl radical; or
alkyl$_{(C≤12)}$, aralkyl$_{(C≤12)}$, acyl$_{(C≤12)}$, or a substituted version of any of these groups; $R_c$ is hydroxy or oxyl radical; and
L is a covalent bond; or
a group of the formula:

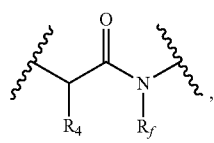

(IIIa)

wherein:
$R_f$ is hydrogen, alkyl$_{(C≤12)}$, or substituted alkyl$_{(C≤12)}$;
$R_4$ is hydrogen; or
alkyl$_{(C≤12)}$, aralkyl$_{(C≤12)}$, heteroaralkyl$_{(C≤12)}$, or a substituted version of any of these groups;
or a pharmaceutically acceptable salt thereof.
In some embodiments, $X_3$ is —S—, —S(O)—, or —$S(O)_2$—. In some embodiments, $R_f$ is hydrogen. In some embodiments, $R_4$ is alkyl$_{(C≤12)}$, substituted alkyl$_{(C≤12)}$, aralkyl$_{(C≤12)}$, or substituted aralkyl$_{(C≤12)}$. In further embodiments, $R_4$ is alkyl$_{(C≤2)}$ or substituted alkyl$_{(C≤12)}$. In still further embodiments, $R_4$ is substituted alkyl$_{(C≤12)}$, such as —$CH_2CH_2SCH_3$. In other embodiments, $R_4$ is aralkyl$_{(C≤12)}$, or substituted aralkyl$_{(C≤12)}$. In further embodiments, $R_4$ is substituted aralkyl$_{(C≤12)}$, such as 4-hydroxybenzyl. In other embodiments, $R_4$ is -alkanediyl$_{(C≤12)}$-$ONO_2$ or substituted -alkanediyl$_{(C≤12)}$-$ONO_2$. In further embodiments, $R_4$ is -alkanediyl$_{(C≤12)}$-$ONO_2$, such as -ethanediyl-$ONO_2$. In some embodiments, L is a covalent bond. In some embodiments, $R_c$ is hydroxy. In other embodiments, $R_c$ is oxyl radical.

In some embodiments, the compound is a compound of formula (IV). In some embodiments, the compound is further defined as:

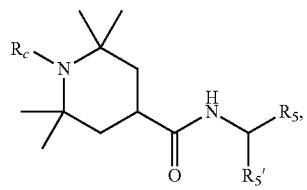

(IV)

wherein:
$R_c$ is hydroxy or oxyl radical;
$R_5$ is —$CO_2R_g$, wherein:
$R_g$ is hydrogen; or
alkyl$_{(C≤12)}$, substituted alkyl$_{(C≤12)}$, cycloalkyl$_{(C≤12)}$, or substituted cycloalkyl$_{(C≤12)}$; and
$R_5'$ is hydrogen; or
alkyl$_{(C≤12)}$, aralkyl$_{(C≤12)}$, heteroaralkyl$_{(C≤12)}$, or a substituted version of any of these groups;
or a pharmaceutically acceptable salt thereof.

In some embodiments, $R_g$ is alkyl$_{(C≤12)}$, such as methyl. In some embodiments, $R_5'$ is alkyl$_{(C≤12)}$ or substituted alkyl$_{(C≤12)}$. In further embodiments, $R_5'$ is substituted alkyl$_{(C≤12)}$, such as —$CH_2CH_2SCH_3$. In some embodiments, $R_c$ is hydroxy. In other embodiments, $R_c$ is oxyl radical.

In some embodiments, the compound is further defined as:

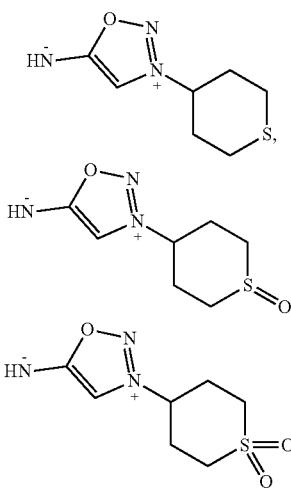

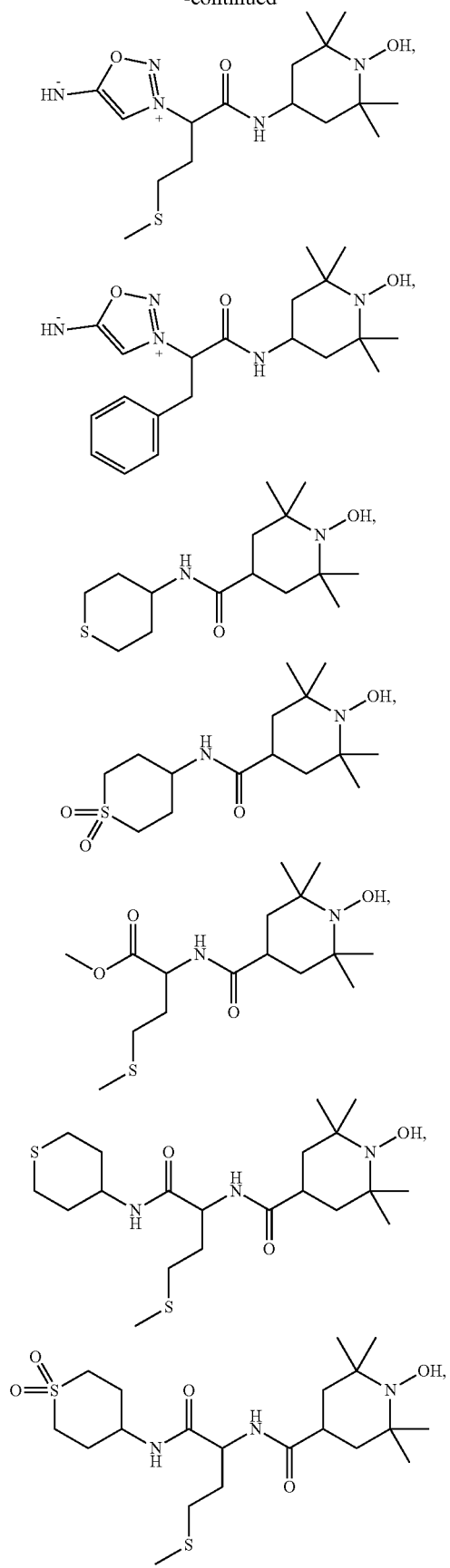
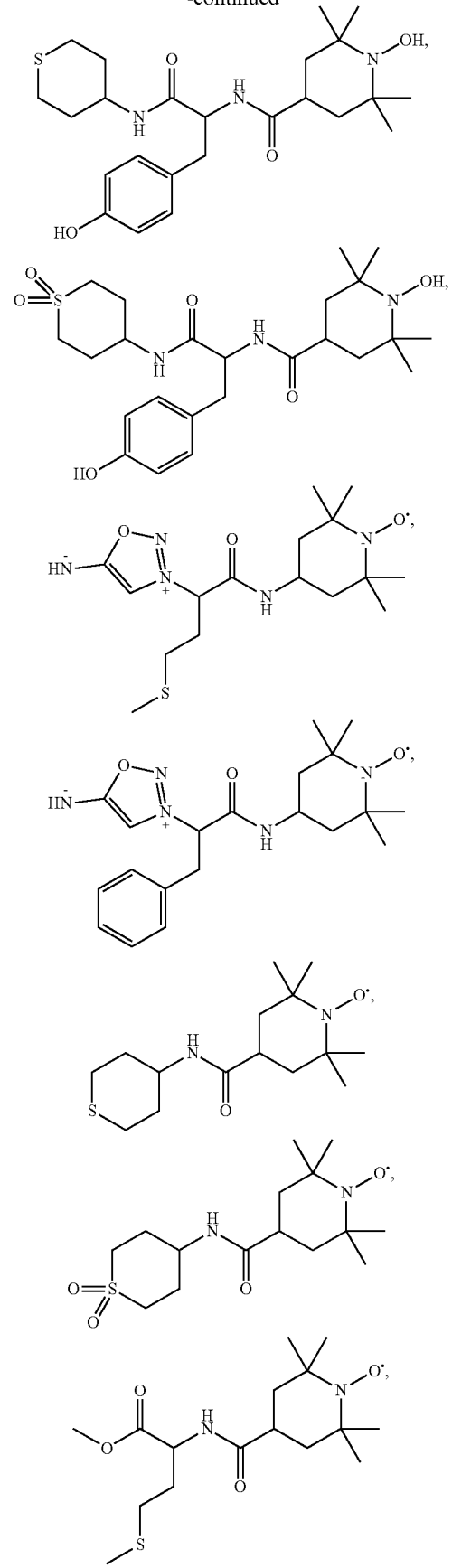

-continued
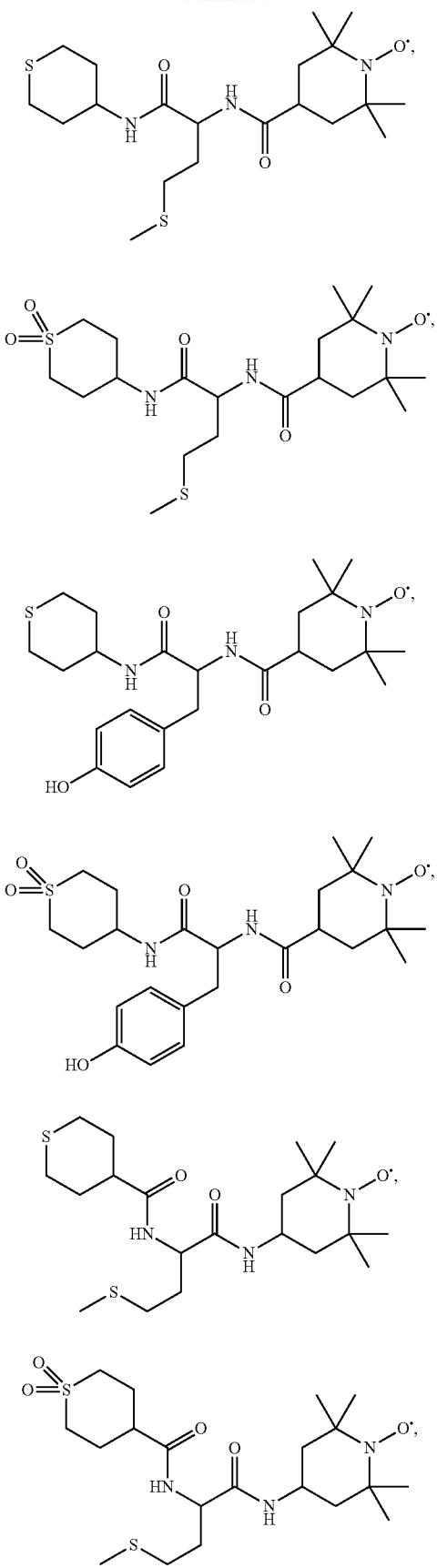
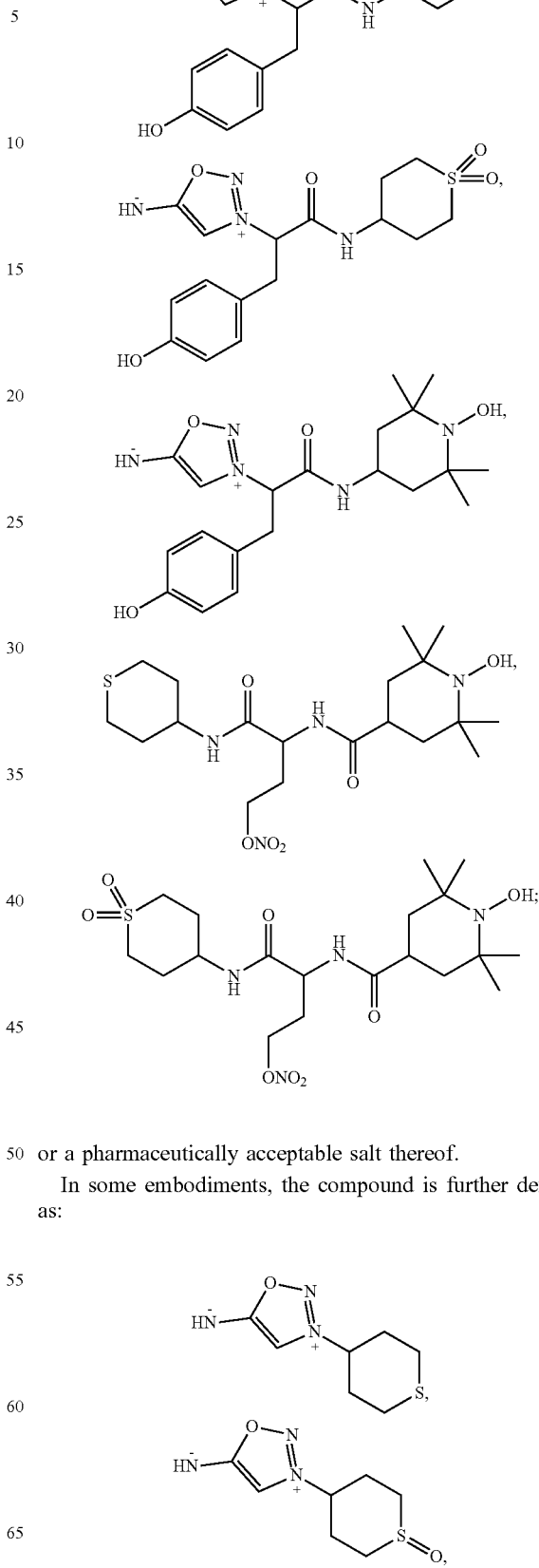
or a pharmaceutically acceptable salt thereof.
In some embodiments, the compound is further defined as:
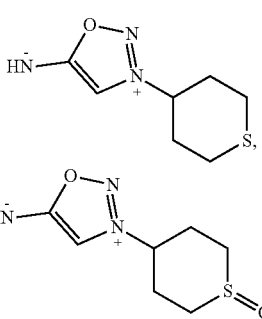

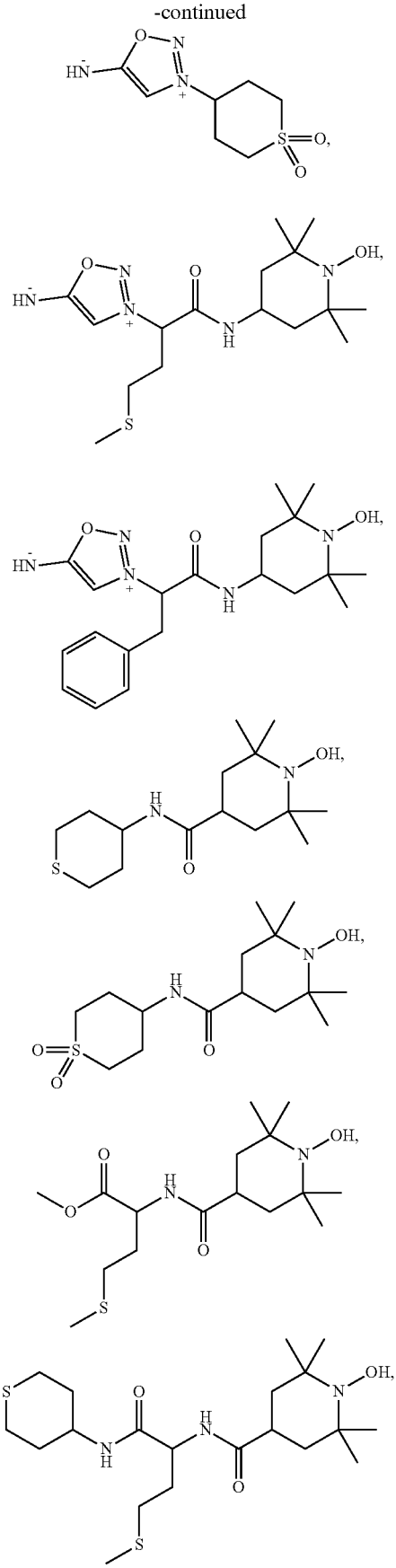

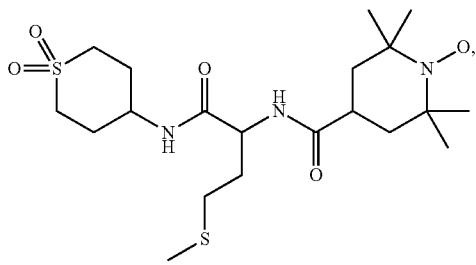

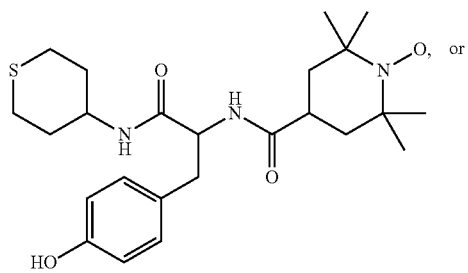

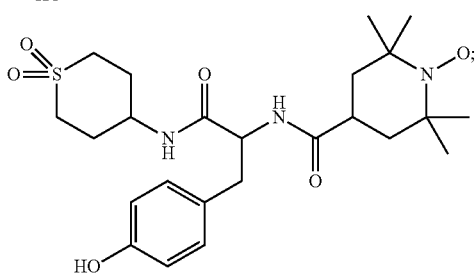

or a pharmaceutically acceptable salt thereof.

In another aspect, the present disclosure provides pharmaceutical composition comprising:

a) a compound disclosed herein; and b) an excipient and/or a pharmaceutically acceptable carrier.

In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the compound is:

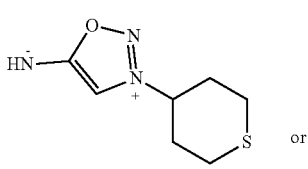

or

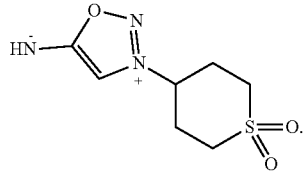

In some embodiments, the compound is formulated as a nanoparticle. In some embodiments, the composition comprises PLGA.

In another aspect, the present disclosure provides conjugates, wherein the conjugates comprise a compound of the present invention and a PPAR δ agonist, such as GW0742. In some embodiments, the conjugates are prepared via amide bond formation between an amine and a carboxylic acid. In some embodiments, the compound of the present disclosure comprises the amine and the PPAR δ agonist comprises the carboxylic acid. In other embodiments, the PPAR δ agonist comprises the amine and the compound of the present disclosure comprises the carboxylic acid.

In still another aspect, the present disclosure provides methods of treating or preventing a disease or disorder in a patient in need thereof comprising administering to the patient a therapeutically effective amount of a compound, a composition, or a conjugate disclosed herein. In some embodiments, the patient is a mammal, such as a human. In some embodiments, the disease is an eye disease. In some embodiments, the disease or disorder is ischemia, ischemia/reperfusion injury, ischemic neuropathy, Bronco pulmonary dysplasia, acute lung injury, acute respiratory distress syndrome, traumatic brain injury, glaucoma, glaucomatous optic neuropathy, age-related macular degeneration, diabetic retinopathy, pulmonary arterial disease, peripheral arterial diseases, atherosclerosis, hind limb ischemia, angina pectoris, or high blood pressure. In some embodiments, the methods comprise administering a second therapeutic agent. In further embodiments, the second therapeutic agent is a PPAR δ agonist, such as GW0742.

In some embodiments, the disease or disorder is the result of an ischemic event. In some embodiments, the ischemic event occurred less than 48 hours before administering. In some embodiments, the ischemic event occurred less than 24 hours before administering. In some embodiments, the ischemic event occurred less than 12 hours before administering. In some embodiments, the ischemic event occurred less than 6 hours before administering. In some embodiments, the compound or composition is formulated as a nanoparticle. In further embodiments, the nanoparticle comprises PLGA.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 9A-9D show PERG analysis of retinas of ischemic I/R-mice (I/R+PBS), and SA-10-treated I/R mice 1 week after injury. FIG. 9A shows amplitude of eyes treated with PBS or with the test compounds. FIG. 9B shows latency of PERG measured in millisecond from mice eyes before and after ischemic reperfusion injury. FIG. 9C shows flash ERG after 28 days post-I/R in mice (n=5). Retinal ischemia/reperfusion resulted significant reduction in the amplitude of both a- and b-wave of the electroretinogram (ERG) as shown in FIG. 9C (I/R+PBS). Compound SA-10 significantly reversed these damages, which is further confirmed from the improved whole retinal layer thickness as measured by SD-OCT (FIG. 9D).

FIGS. 10A & 10B show pyrogallol induced superoxide scavenging activity of SA compounds. FIG. 10A represents compounds with both NO releasing and anti-oxidant functionalities. SIN-1, a standard NO donor was used as control. FIG. 10B represents hybrid antioxidants and compared with a commercial polyphenolic anti-oxidant baicalein, FIGS. 11A & 11B show the superior activity of SA-9 in cell viability assay over SA-2. FIGS. 11C & 11D show the superior cytoprotective activity of SA-9 in human trabecular meshwork cells under TBHP (300 µM) induced oxidative stress condition.

DESCRIPTION OF ILLUSTRATIVE EMBODIMENTS

Figure 1:
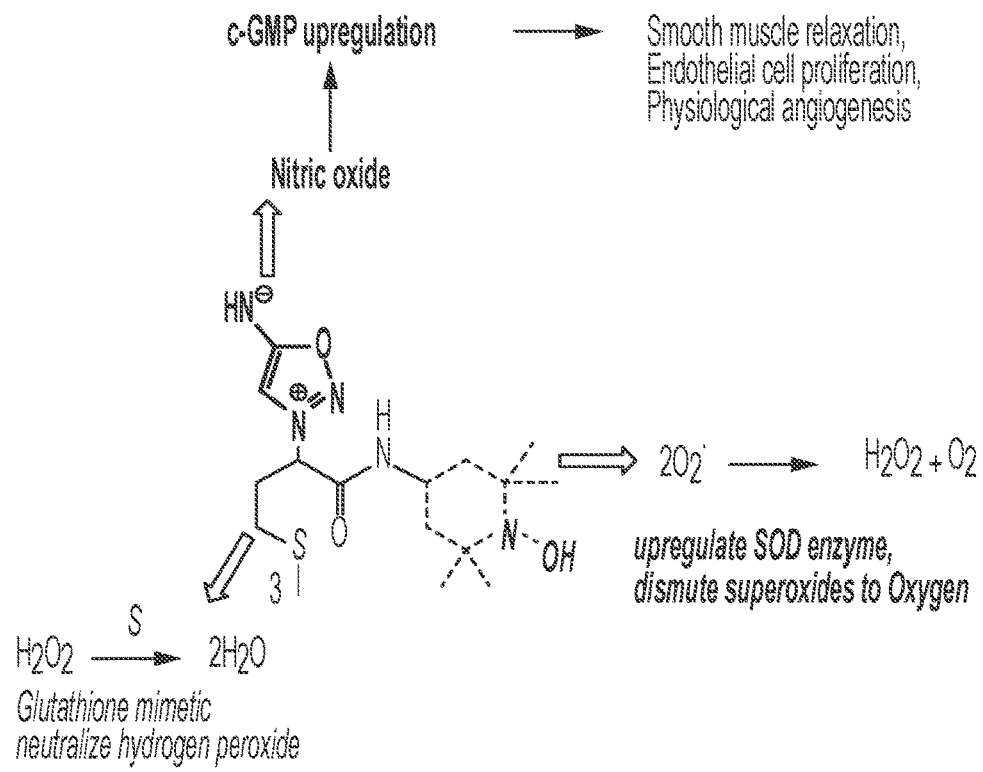
FIG. 1 shows the multiple activity of hybrid compound 3, a representative example of the compounds of the present disclosure.

In some aspects, the present disclosure provides sydnone imines and/or sulfur-containing compounds and derivatives with therapeutic properties that may be used to generate NO and regulate ROS. In some embodiments, the compound may be used to treat or prevent retinal ischemia and hind limb ischemia. Without wishing to be bound by any theory, it is believed that the compounds of the present disclosure act in a multifunctional manner, both generating NO and reducing ROS.

I. COMPOUNDS OF THE PRESENT DISCLOSURE

The compounds of the present disclosure (also referred to as "nitric oxide donors" or "compounds disclosed herein") are shown, for example, above, in the summary section, the Examples below, Table A, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

TABLE A

Compounds of the Present Disclosure

| Compound ID | Structure |
| --- | --- |
| SA-2 (comparison compound) | 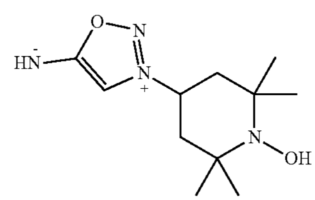 |
| 1 (i.e., SA-9) | 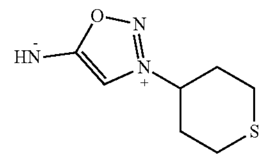 |
| 2 (i.e., SA-10) | 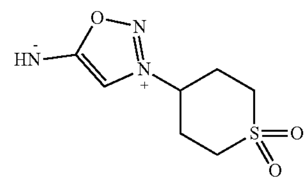 |
| 3 (SA-27) | 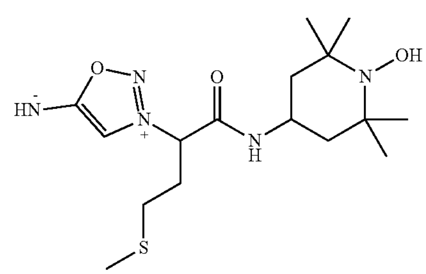 |

TABLE A-continued
Compounds of the Present Disclosure
| Compound ID | Structure |
|---|---|
| 4 | 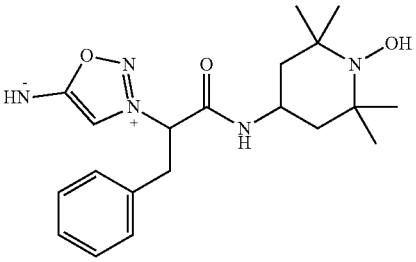 |
| 5 (SA-23) | 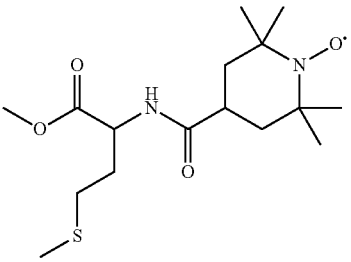 |
| 6 (SA-21) | 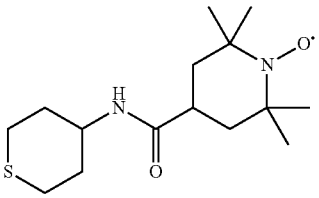 |
| 7 (SA-24) | 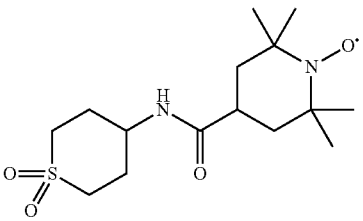 |
| 8 | 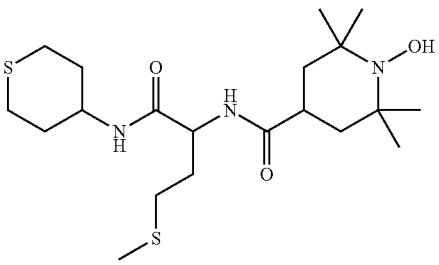 [SMILES: CSCCC(NC(=O)C1CC(C)(C)N(O)C(C)(C)C1)C(=O)NC1CCSCC1] |
| 9 (SA-25) | 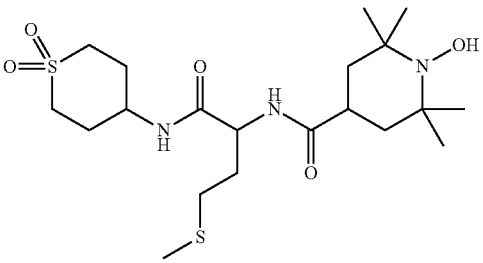 [SMILES: CSCCC(NC(=O)C1CC(C)(C)N(O)C(C)(C)C1)C(=O)NC1CCS(=O)(=O)CC1] |

TABLE A-continued
Compounds of the Present Disclosure
| Compound ID | Structure |
| --- | --- |
| 10 | 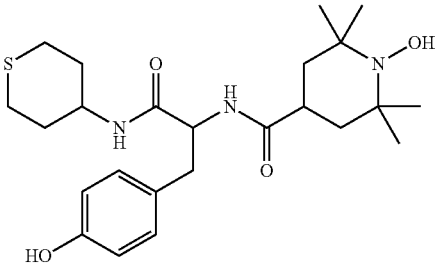 [SMILES: CC1(C)CC(C(=O)NC(Cc2ccc(O)cc2)C(=O)NC2CCSCC2)CC(C)(C)N1O] |
| 11 | 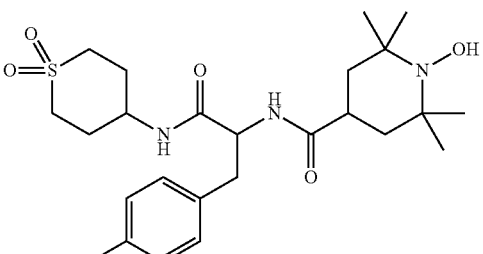 |
| 12 | 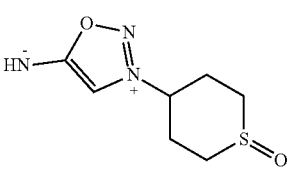 |
| 13 | 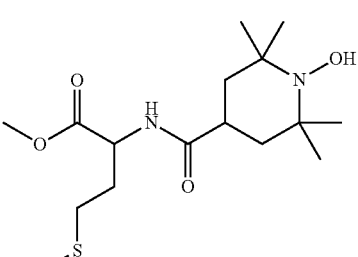 |
| 14 | 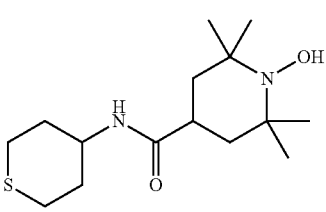 [SMILES: CC1(C)CC(C(=O)NC2CCSCC2)CC(C)(C)N1O] |
| 15 | 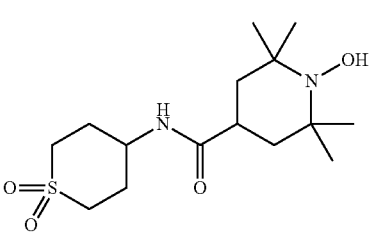 [SMILES: CC1(C)CC(C(=O)NC2CCS(=O)(=O)CC2)CC(C)(C)N1O] |

TABLE A-continued
Compounds of the Present Disclosure
| Compound ID | Structure |
|---|---|
| 16 | 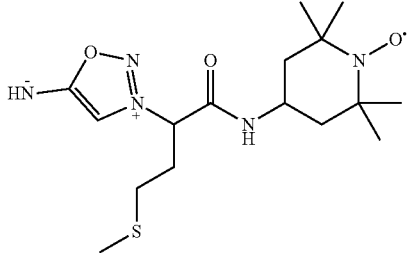 |
| 17 | 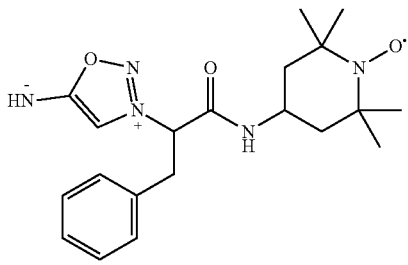 |
| 18 | 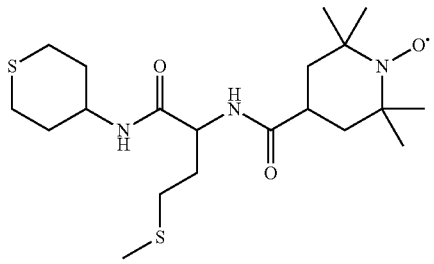 |
| 19 | 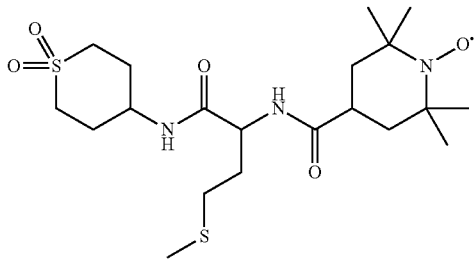 |
| 20 | 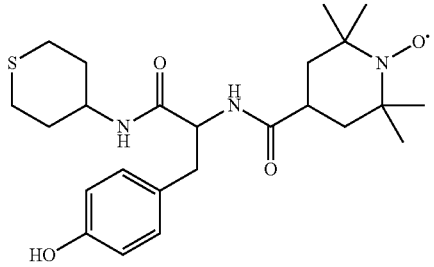 |

TABLE A-continued

Compounds of the Present Disclosure

| Compound ID | Structure |
|---|---|
| 21 | 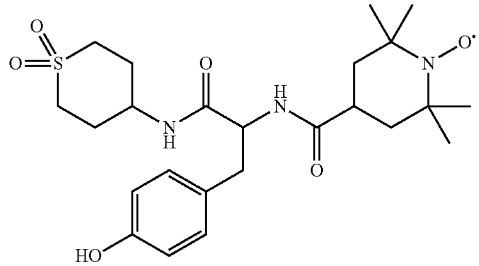 |
| 22 (SA-26) | 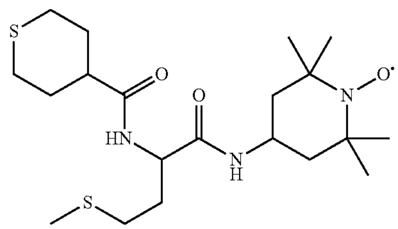 |
| 23 | 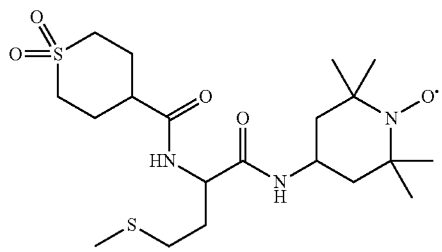 |
| 24 | 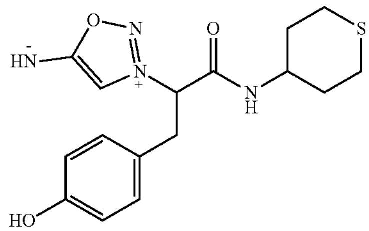 |
| 25 | 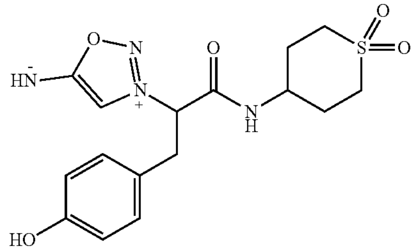 |
| 26 | 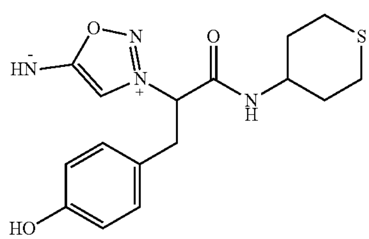 |

TABLE A-continued

Compounds of the Present Disclosure

| Compound ID | Structure |
|---|---|
| 27 | 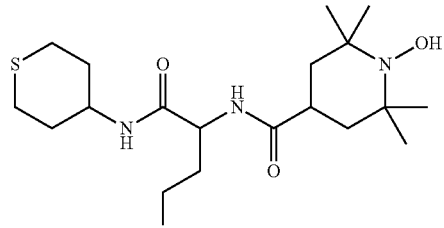 |
| 28 | 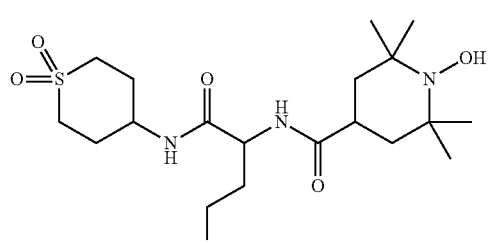 |

TABLE B

Total area under curve (AUC) of SA compounds at different time points in the pyrogallol induced ROS scavenging assay

| Compound ID | Concentration | AUC$_{t=0\ to\ t=3h}$ | Time |
|---|---|---|---|
| SIN-1 | 250 µM | 1856 | 0.5 h |
| SA-2 | 250 µM | 3338 | 0.5 h |
| SA-9 | 250 µM | 3402 | 0.5 h |
| SA-22 | 250 µM | 2821 | 0.5 h |
| SA-21 | 250 µM | 2954 | 0.5 h |
| SA-23 | 250 µM | 1613 | 0.5 h |
| SA-24 | 250 µM | 2786 | 0.5 h |
| Baicalein | 250 µM | 1944 | 0.5 h |

All the compounds of the present disclosure may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present disclosure are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present disclosure have the advantage that they may be more efficacious than, be less toxic than, be longer acting than, be more potent than, produce fewer side effects than, be more easily absorbed than, more metabolically stable, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present disclosure may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

In some embodiments, compounds of the present disclosure exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present disclosure exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. DISEASES AND CONDITIONS TO BE TREATED IN ACCORDANCE WITH THE DISCLOSURE

A. Ischemia and Related Diseases

Ischemic stress followed by reperfusion results in burst of superoxide free radicals that induce oxidative stress in RGCs, resulting in apoptosis of these cells (Yokoyama et al., 2014) and dysfunction of endothelial cells of retina resulting in poor blood circulation. Hence to circumvent the multifaceted pathological demand of ischemic stroke, there exists a need to develop a single pharmacological intervention that may prevent dysfunction of endothelial cells, promote vasodilation, and neutralizes reactive oxygen species (ROS) resulted from oxidative stress, thereby providing robust neuroprotection.

Acute arterial thrombosis subjects the end organ to acute ischemic insult, resulting in myocardial infarction, acute limb ischemia, or stroke depending on the location of thrombosis (Go et al., 2014). According to American Heart Association, about 8.5 million American at age more than 40 (10%) are suffered from PAD, a cutaneous microvascular dysfunction of blood vessels to limbs that are partially or completely blocked by atherosclerosis (Go et al., 2014), and this disease is worst in elderly patients (~20%; Garg et al., 2016). Particularly, patients with critical limb ischemia (CLI) associated with PAD has high rates of deaths and amputations (Go et al., 2014, Reinecke et al., 2015 and Newhall et al., 2016), potentially due to the limited application of endovascular interventions for the patients with higher risks of hypertension and hypercholesterolemia (Camci-Unal et al., 2013, Hackl et al., 2015, and Fokkema et al., 2016). The available adenosine triphosphate (ATP) is normally metabolized to uric acid via xanthine dehydrogenase, but during anaerobic metabolism due to PAD this process is shifted to xanthine oxygenase (Hackl et al., 2015 and Fokkema et al., 2016). The xanthine oxygenase uses available oxygen and convert them to uric acid via production of free radicals, resulting in oxidative cell damage (followed by cell death) and increased inflammatory cytokines. These free radical insults occur not only in the end organ but also remote injury to other organs in body (Reinecke et al., 2015 and Newhall et al., 2016). The endothelial cells (ECs) are damaged as the result of anaerobic metabolism with low ATP, oxidative cell damage, and inflammatory insults. Thus, the damaged endothelial cells are impaired and unable to produce nitric oxide (NO), an important regulator of EC functions. Although traditional treatments such as endovascular and percutaneous interventions can improve blood flow and restore blood vessel functions, many of these elderly PAD patients cannot undergo surgical options (Whitehill, 1997, de Leur et al., 2012, and Grochot-Przeczek et al., 2013). The facts on PAD indicate that it is important to develop an alternative therapy to treat PAD and the facts on ischemic reperfusion injury indicate that, it is critical to treat ischemic reperfusion injury via producing NO and reducing free radicals.

B. Peripheral Artery Disease

Peripheral arterial disease (PAD) is a disease where one or several peripheral arteries not directly connected to heart (so-called noncardiac, nonintracranial arteries) are narrowed or blocked. PAD commonly happens on lower extremities of the body. According to The American Heart Association (AHA) statistics, at least 200 million people worldwide suffer from PAD. Numbers for the U.S. are 8.5 million patients (12% of American adults) at ages of 40 or greater, with about 20% of PAD patients over 70 years of age. Atherosclerosis, where arteries have deposition of substances such as cholesterol, fatty substances, cellular waste products, calcium and fibrin, is the main cause of PAD. Less common causes include inflammatory disorders of the arterial wall (vasculitis) and noninflammatory arteriopathies such as fibromuscular dysplasia. Hypertension, obesity, dyslipidemia, smoking, diabetes, coronary artery disease, chronic heart failure and chronic kidney disease are other causes of PAD. It is also noted that PAD currently presents in almost 40% of cardiovascular disease (CVD)-related diabetic cases.

Traditional therapy approaches such as changing lifestyle, bypass grafting, and endovascular interventions have been used to treat PAD. Lifestyle changes start with routine exercise that subsequently helps bring lipids, blood pressure, and blood sugar under control. Since smoking stands as an important contributor to PAD, it is crucial that patients should cease tobacco use. Pharmacotherapy, including but not limited to antiplatelet and statin agents, antihypertensive agents, cilostazol and influenza vaccination, is used under medical supervision.

CLI requires either surgical or endovascular revascularization to provide in-line blood flow to the foot. Initially, autologous vein bypass transplantation is considered as the first line therapy in PAD. Endovascular revascularization for claudication includes balloon dilation (angioplasty), cutting balloons, drug-coated balloons, covered stents, drug-eluting stents, and atherectomy. The therapeutic efficacy of endovascular intervention, however, is limited due to late restenosis. Another effective approach is surgical intervention called surgical bypass. The surgical bypass is usually performed on femoral and proximal popliteal arteries where stenosis and occlusion commonly happen among individuals with claudication. The preferred type of conduit is autogenous vein over prosthetic graft materials. Recently, however, the "Bypass versus Angioplasty in Severe Ischemia of the Leg" (BASIL) study suggested that endovascular revascularization is more effective than open surgery for patients with CLI. A 3-fold increase in endovascular revascularization for PAD patients with CLI has been reported over 1996-2006, which was doubled (from 13.4% to 27.4%) for the period 2001-2011. Clinically, endovascular revascularization is recommended for patients with ischemic rest pain, non-healing wounds, or gangrene. Meanwhile, surgical intervention is still associated with greater risk of adverse perioperative events. Surgical bypass is recommended when endovascular revascularization has failed for patients with CLI. The bypass to the popliteal or infrapopliteal arteries is recommended with suitable autogenous veins. The saphenous vein is the preferred conduit for infrainguinal bypass, while a prosthetic conduit can be used for femoral-popliteal bypass. Femoral-tibial artery bypasses with prosthetic graft materials are accepted under AHA/ACC guidelines once autologous veins are not available.

Nevertheless, these interventions often cause thrombosis and restenosis and require response availability of patients to surgery or intervention. Overall, as many as 20-30% of PAD patients with CLI are not suitable candidates to undergo either surgery or endovascular revascularization. Recently, new approaches to treat PAD that avoid such intervention and/or operation have garnered more attention from scientists. The non-surgical treatments include i) introduction of living stem cells (SCs) to cure lesions, and ii) investigation of small drugs (e.g., antiplatelet reagents, fibrinogen inhibitors, nitric oxide donors and antioxidants) and growth factors (e.g., vascular endothelial growth factor (VEGF), basic fibroblast growth factor (bFGF), hepatocyte growth factor (HGF) and nerve growth factor (NGF)) that participate in the formation new blood vessels. While living SCs have attracted attention due to their potential of homeostasis, pro-angiogenesis and differentiation into other cell types, including endothelial cells (ECs), SCs have very poor retention time as they are easily attacked and cleared out by the immune system. More importantly, it has been proven that some cancers have been originated from either undifferentiated or overactivated self-renewal SCs.

It has been reported that particulates that either supply nitric oxide (NO) or scavenge reactive oxygen species (ROS) play important roles in inducing angiogenesis. At the ischemic area, lack of oxygen supply causes dysfunction in ECs, leading to a decrease in nitric oxide synthase (NOS), with ECs failing to synthesize NO. Meanwhile, EC dysfunctions attract immune cells and produces more ROS, leading to poor endothelial progenitor cell (EPCs) viability, more EC dysfunction and smooth muscle cell (SMC) recruitment that consequently result in atherosclerosis and/or chronic inflammatory conditions. There has been discussion elsewhere in literature about the organic relation between NO and ROS. Specifically, excessive NO supply reacts with ROS that not only diminishes NO but also forms toxic peroxynitrite ($ONOO^{.-}$). Thus, it is crucial to supplement NO donors with antioxidants to maintain NO and ROS at physiological levels.

III. PHARMACEUTICAL FORMULATIONS AND ROUTES OF ADMINISTRATION

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m / \text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may be taken orally and that the timing of which is or is not dependent upon food intake. Thus, for example, the agent can be taken every morning and/or every evening, regardless of when the patient has eaten or will eat.

IV. COMBINATION THERAPY

In addition to being used as a monotherapy, the compounds of the present disclosure may also find use in combination therapies. Effective combination therapy may be achieved with a single composition or pharmacological formulation that includes both agents, or with two distinct compositions or formulations, administered at the same time, wherein one composition includes a compound of this disclosure, and the other includes the second agent(s). Alternatively, the therapy may precede or follow the other agent treatment by intervals ranging from minutes to months.

Non-limiting examples of such combination therapy include combination of one or more compounds of the disclosure with another anti-inflammatory agent, a vasodilator, a ROS neutralizing agent, an antihypertensive agent, an antithrombotic agent, an agent for treating or preventing cardiovascular events such as myocardial infarction or stroke, or an analgesic agent.

V. DEFINITIONS

The definitions below supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

A. Chemical Groups

When used in the context of a chemical group: "hydrogen" means —H; "hydroxy" means —OH; "oxo" means =O; "oxyl radical" means —O·, wherein the oxygen atom has a single unpaired valence electron, and may be depicted as —O without explicit depiction of the single unpaired electron; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⇌" represents a single bond or a double bond. Thus, the formula

covers, for example,

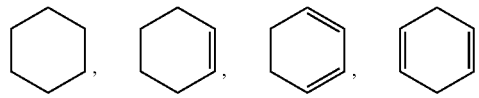

and

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "〰", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "▮▮▮▮" means a single bond where the group attached to the thick end of the wedge is "into the page". The symbol "〰" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parentheses, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen.

If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

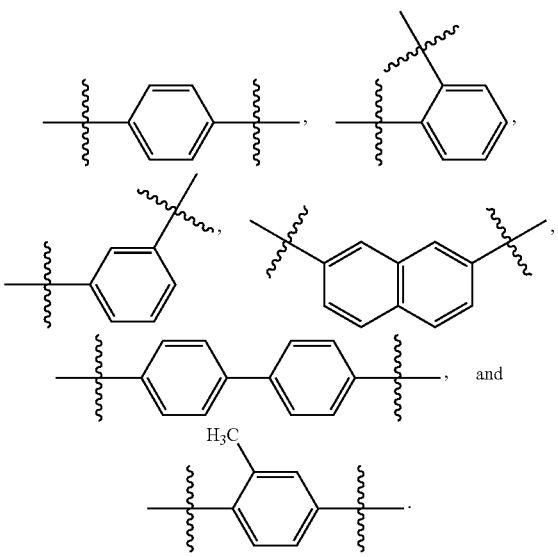

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaralkyl" refers to the monovalent group -alkanediyl-heteroaryl, in which the terms alkanediyl and heteroaryl are each used in a manner consistent with the definitions provided above. Non-limiting examples are: pyridinylmethyl and 2-quinolinyl-ethyl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —SCH$_3$, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC (O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

B. Other Definitions

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active.

The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a compound or composition used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-p-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

As used herein, one or more of the following abbreviations may be used in the application: NO, nitric oxide; ROS, reactive oxygen species; I/R, ischemia/reperfusion; EDCI, 3-(ethyliminomethyleneamino)-N,N-dimethylpropan-1-amine, HOBt, benzotriazol-1-ol; TFA, trifluoracetic acid; DIPEA, N,N-diisopropylethylamine; and DCFDA, 2',7'-dichlorofluorescin diacetate.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Compounds and Synthesis

Compounds 1 (i.e., SA-9) and 2 (i.e., SA-10) were prepared from the corresponding amine following the protocol as described in the literature (Acharya et al., 2016). $^1$H NMR (CD$_3$OD, 300 MHz) of compound 1: δ 2.31-2.42 (m, 2H), 2.58-2.63 (m, 2H), 2.74-3.02 (m, 4H), 4.90-4.95 (m, 1H), 7.98 (s, 1H). ¹H NMR (CD₃OD, 300 MHz) of compound 2: δ 2.74-3.02 (m, 4H), 3.42-3.51 (m, 4H), 5.32-5.43 (m, 1H), 8.01 (s, 1H).

The synthesis of compound 3 was achieved according to route outlined in Scheme 1, below.

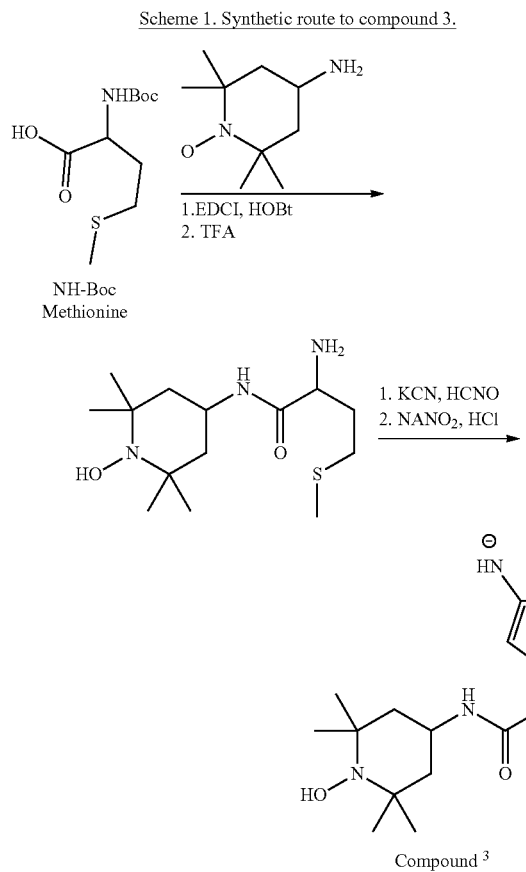

¹H NMR (CD₃OD, 300 MHz) of compound 3: δ 1.42-1.68 (m, 12H), 1.96-2.20 (m, 2H), 2.27-2.41 (m, 4H), 2.72-2.74 (m, 1H), 3.02 (s, 3H), 3.45 (s, 2H), 4.02-4.-5 (m, 1H).

Compound 4 was prepared following the same procedure as described for compound 3. ¹H NMR (CD₃OD, 300 MHz) of compound 4: δ 1.42-1.68 (m, 12H), 1.96-2.20 (m, 2H), 2.27-2.41 (m, 2H), 2.72-2.74 (m, 1H), 3.02-3.12 (m, 2H), 7.19-7.23 (m, 5H), 7.81 (s, 1H).

The synthesis of compounds 5-7 was achieved according to route outlined in Scheme 2, below.

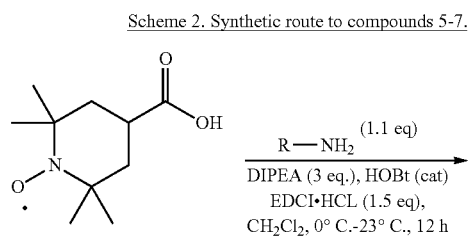

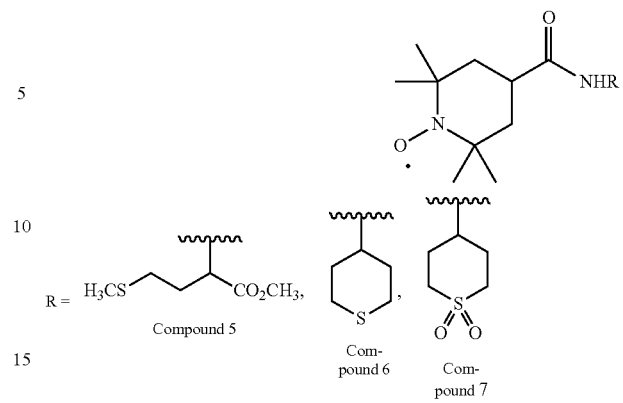

To the acid, in 10 mL of dichloromethane (CH₂Cl₂), amine was added, cooled to ° C., DIPEA, HOBt, were added sequentially and stirred for 5 min. Then EDCI·HCl was added and the reaction mixture was stirred overnight at room temperature. TLC was checked for completion of the reaction. 15 mL water was added to quench the reaction, the organic material extracted with ethyl acetate (2×20 mL). The combined organic layers were washed with water, brine, dried over Na₂SO₄, evaporated in rotavapor. The crude mixture was purified by column chromatography using LC and characterized by ¹H NMR.

¹H NMR (CDCl₃, 300 MHz) of compound 5: δ 1.61-1.82 (m, 12H), 1.75-1.95 (m, 1H), 2.01-2.62 (m, 4H). 2.75 (m, 1H), 3.25 (s, 3H), 3.40-3.620 (m, 4H), 3.90 (s, 3H), 4.51-4.53 (m, 1H).

¹H NMR (CDCl₃, 300 MHz) of compound 6: δ 1.02-1.94 (m, 16H), 2.04-2.48 (m, 2H), 2.52-2.90 (m, 7H), 3.85 (t, 1H).

¹H NMR (CD₃OD, 300 MHz) of compound 7: δ 1.6-1.8 (m, 16H), 2.04-2.48 (m, 5H), 3.60-3.80 (m, 4H), 4.15 (t, 1H).

-continued

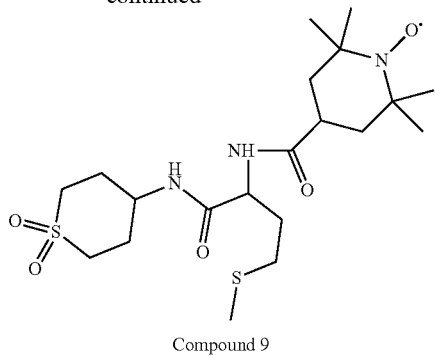

Compound 9

N-Boc methionine was coupled with the sulfone carboxylic acid (commercial) using EDCI, HOBt method as described for synthesizing compound 5. The NHBoc deprotection was achieved by using 25% trifluroacetic acid (TFA) in $CH_2Cl_2$ stirring overnight and the resulted amine was coupled with the corresponding nitrone acid using similar amide coupling procedure. The product was purified using chromatography to provide compound 9 in 35% yield. $^1$H NMR ($CD_3OD$, 300 MHz): δ 2.28-2.35 (m, 4H), 2.81-2.93 (m, 2H), 2.95 (s, 3H), 2.98-3.12 (m, 12H), 3.41-3.46 (m, 1H), 3.58-3.65 (m, 4H), 4.52-5.81 (m, 6H), 4.95 (t, 1H), 5.21-5.35 (m, 2H).

Example 2: Biological Results and Discussion

A. In Vitro Assay

Figures 2A, 2B:
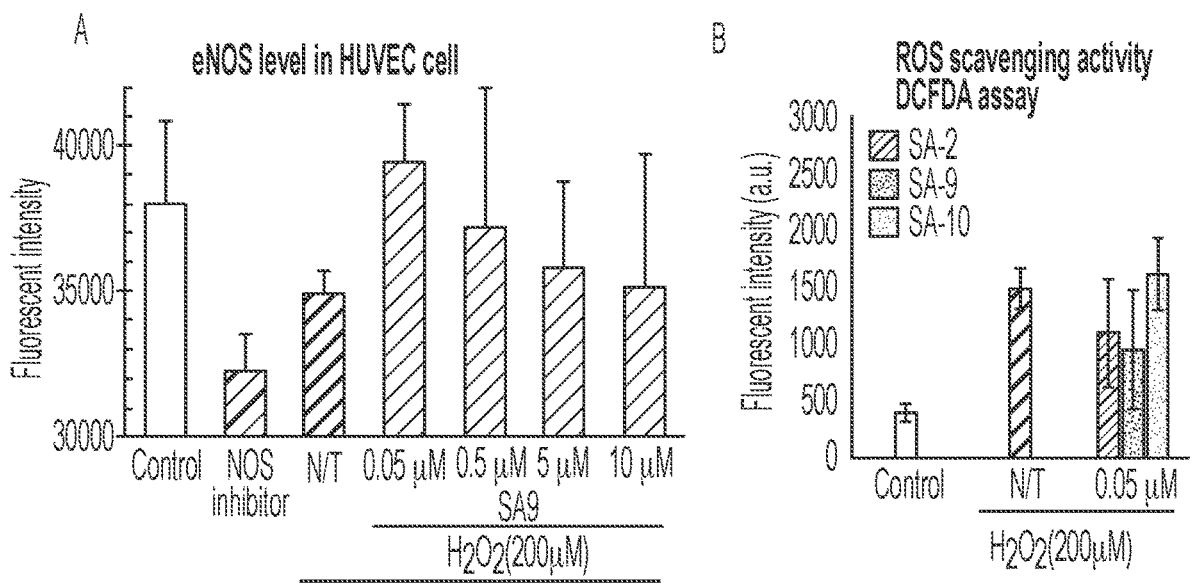
FIGS. 2A & 2B show the hybrid compound SA-9 releases NO (FIG. 2A) and scavenges ROS in HUVEC cells undergoing oxidative stress (FIG. 2B). Treatment with $H_2O_2$ reduces the NOS level (N/T group) where at both doses (0.05 µM and 0.5 µM) of SA-2 and SA-9 increased the level of NOS significantly. NOS inhibitor L-NNA used as negative control. Stars (*), phi (ϕ), double-colon (::) and hashtag (#) indicate significant difference (P<0.01; n=4). ***p<0.001. ANOVA, Tukey's multiple test.

The compounds described herein may maintain a therapeutic level of NO, neutralize excess superoxide ($O2^{1-}$) as well as excess of hydrogen peroxide ($H_2O_2$) generated during Fenton reaction (FIG. 1) whereas the comparison compound SA-2 may only dismute/neutralize the superoxide and not able to destroy the pathological level of $H_2O_2$ that needed to be destroyed by catalase or glutathione. The compounds were shown to protect endothelial cells against oxidative stress. In Human Umbilical Vascular Endothelial Cells (HUVECs), under $H_2O_2$ induced oxidative stress conditions, the hybrid compound SA-9 demonstrated an increase in eNOS activity (FIG. 2A) and scavenged ROS (FIG. 2B) at lower concentration (0.05 μM) where compound SA-10 didn't show any significant ROS scavenging activity in DCFDA assay. The hybrid compounds SA-9 and SA-10 demonstrated potent cytoprotective activity at different concentrations (FIG. 3) and superior to comparison compound SA-2. Compound SA-9 and SA-10 demonstrated the cytoprotective activity from doses ranging from 0.5-100 μM where the efficacy of SA-2 decreased as the dose increased.

Figure 4:
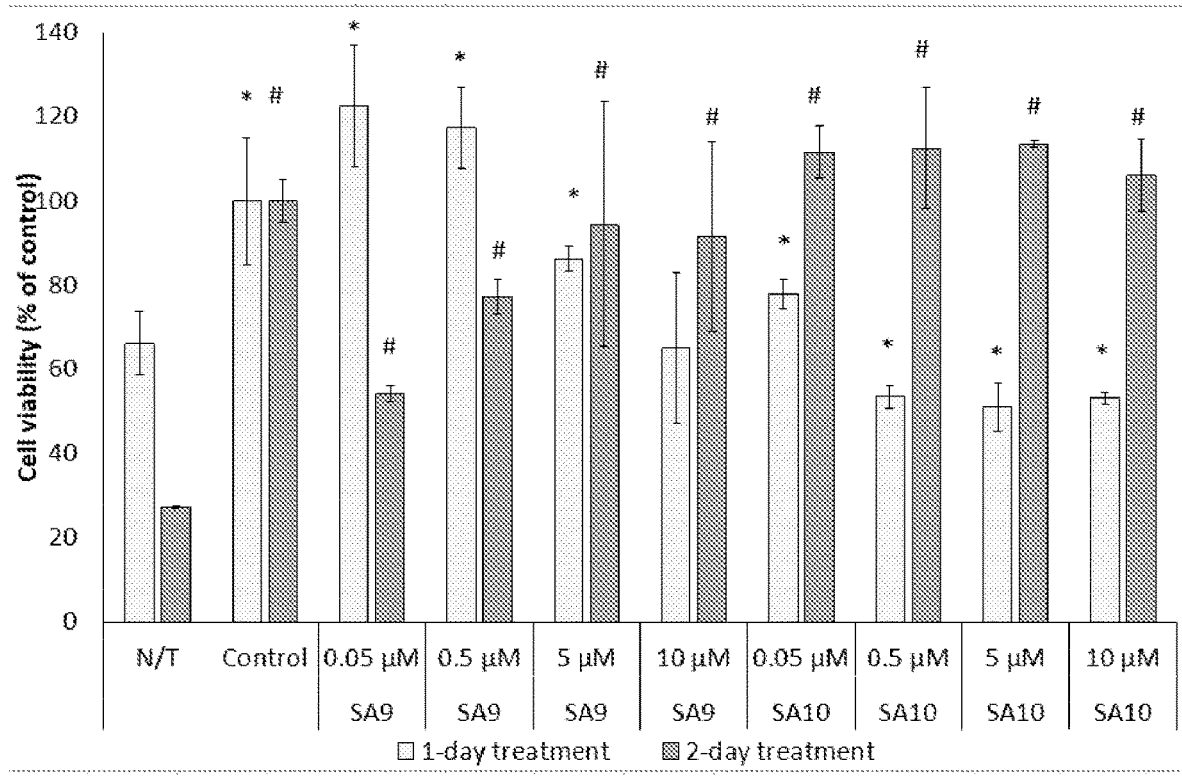
FIG. 4 shows cell viability after 1 day and 2-day treatment. Control: Cells in complete media (2% supplement) and no stress; N/T: Cells in low serum with stress. No drug was treated; Treatment groups: Drug dissolved in low serum media and under stress; Stress: $H_2O_2$ 200 µM; Low serum: EC media with 0.5% supplement; n=4 (each repeat); N=2 (repeat); Significant difference (p<0.05)* and # vs N/T in 1-day and 2-day of treatment, respectively.
Figure 5:
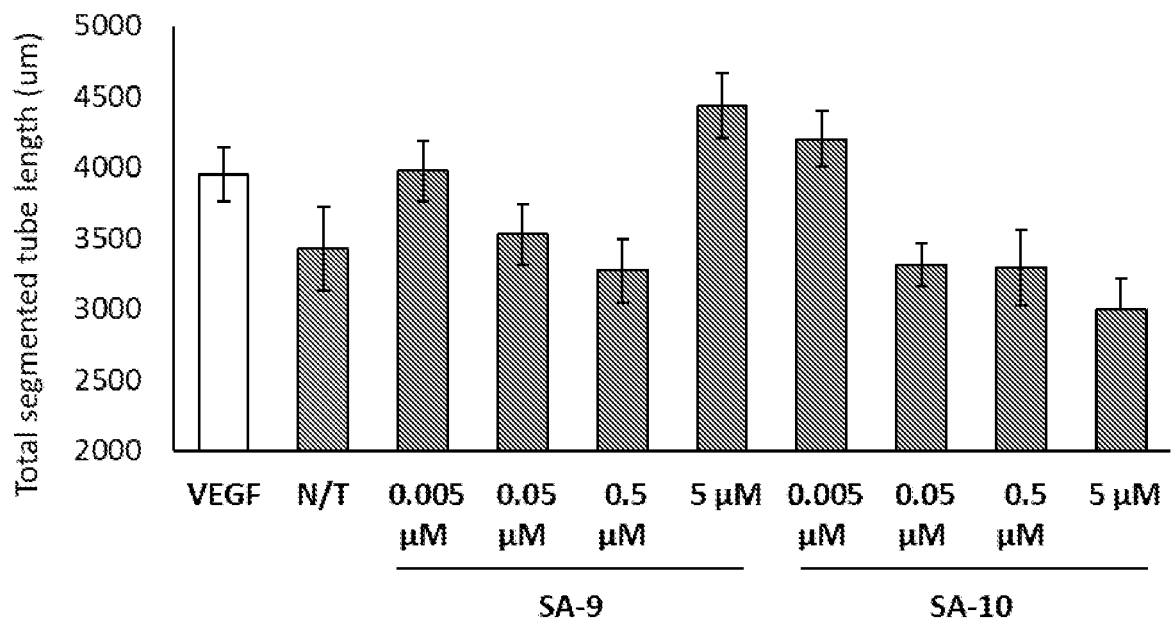
FIG. 5 shows compounds SA-9 (0.5 µM) and SA-10 (0.005 µM) induce angiogenesis and new tube formation in HUVEC under oxidative stress. Cells were seeded 25,000 cells/cm$^2$. All groups are treated with $H_2O_2$ (200 µM) to induce oxidative stress. Media: Low serum media for all groups; n=3 per group; N=2 replicate; # indicates significant vs VEGF (10 ng/mL).
Figure 6:
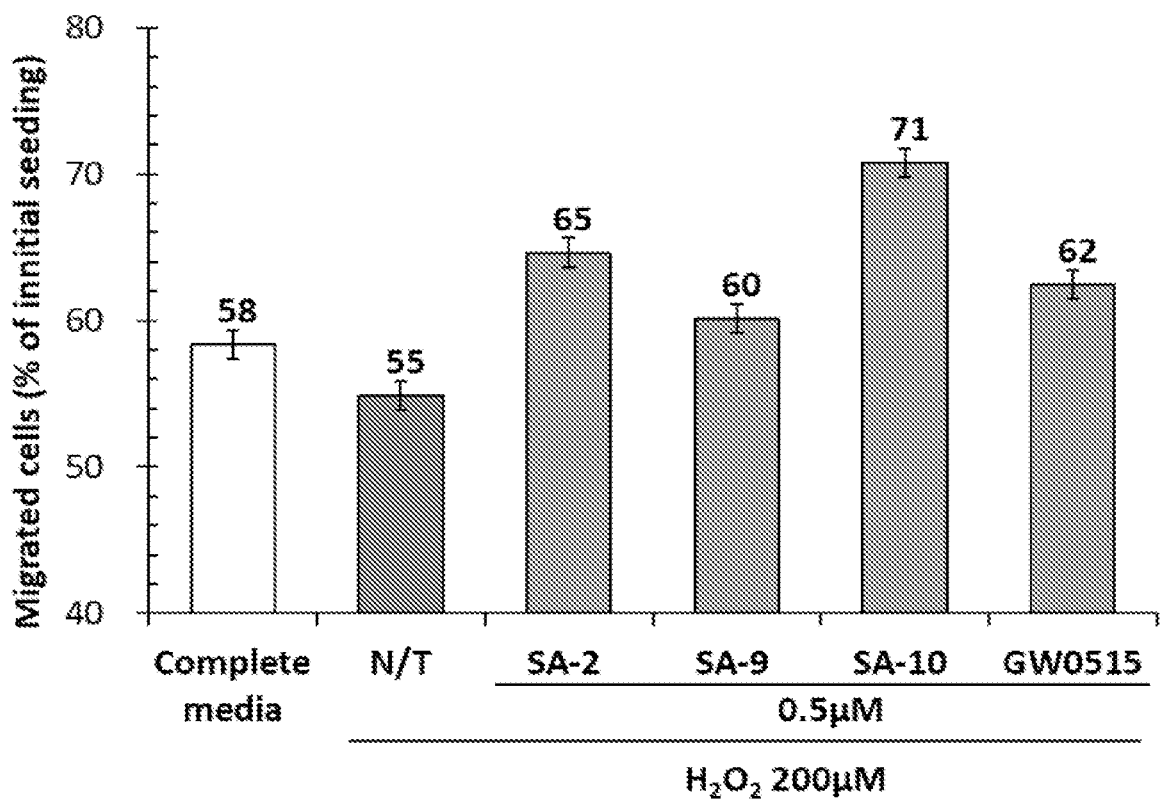
FIG. 6 shows compounds SA-9 (0.5 µM) and SA-10 (0.5 µM) induce EC migration under oxidative stress. Method: Transwell 6-well with 4 m pore sizes; Initial seeding: 100,000 cells/cm$^2$; Insert chamber: cells in low serum media; Chemotactic chamber: Controls & treatments; Control: Cells in complete media (2% supplement) and no stress; N/T: Cells in low serum with stress, no drug was treated; Treatment groups: Drug dissolved in low serum media and under stress; Low serum: EC media with 0.2% supplement; n=15; Cells counted automatically by ImageJ.
Figure 7:
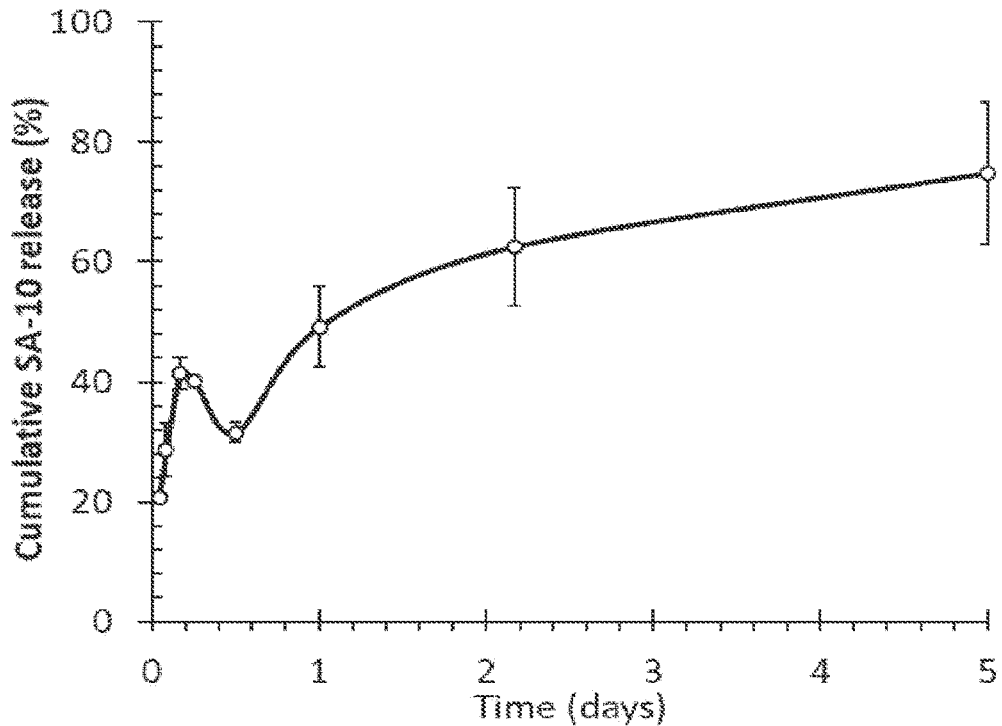
FIG. 7 shows drug release kinetic experiment with PLGA nanoparticles comprising SA-10. The drug release kinetic experiment was performed similarly to the protocol previously described (Lee et al., 2017).

To further understand the duration of action, cell viability was analyzed after 1 day and 2 days. Previously, it was found that SA-2 has short half-life and in order to maintain the cellular activity, it was necessary to refresh the media and redose SA-2 every 12 hours. However, it was found that both compounds SA-9 and SA-10 have longer duration of action and are highly cytoprotective (FIG. 4). Compounds SA-9 and SA-10 induce angiogenesis and new tube formation in HUVEC under oxidative stress (FIGS. 5A & 5B). Compounds SA-9 and SA-10 also induce EC migration under oxidative stress (FIG. 6). PLGA encapsulated nanoparticles of compound SA-10 release compound SA-10 in saline over a period of days (FIG. 7).

Compound SA-9, SA-10, and SA-24 of the present disclosure has demonstrated no cytotoxicity to human trabecular meshwork cells up to 1 mM concentration and SA-9 provided cytoprotection at lower concentration (8 μM) as compared to SA-2 (16 μM) in an oxidative stress induced cell death model.

Figure 15:
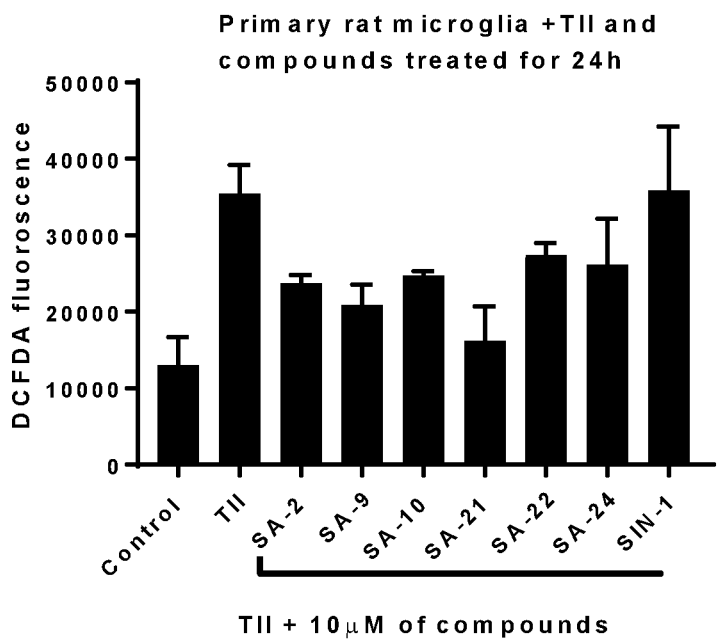
FIG. 15 shows, upon treatment with a cocktail of inflammatory cytokines (TII, TNF-α, IL-1β and IFN-γ) to primary microglia isolated from rat retina for 1 h, there is substantial production of ROS as measured by DCFDA assay. Treatment with 10 µM of SA compounds for 24 h reduced significantly the ROS production where a known NO donor SIN-1 did not.

Compounds SA-10 of the present disclosure showed inhibition of plasminogen activating inhibitor-1 (PAI-1) enzyme induced by dexamethasone (DEX) in human trabecular meshwork cells where SA-2 didn't show such activity (FIG. 15). Briefly, cells were plated at a density of 2×10$^5$ cells per well and were treated with DEX (100 nM) or vehicle (ethanol) in the presence of 100 μM of SA-1, SA-2, SA-9, SA-10 and PBA (positive control) for 48 hr. Conditioned medium was collected for western blot. Experiments were performed in triplicates.

Figure 14:
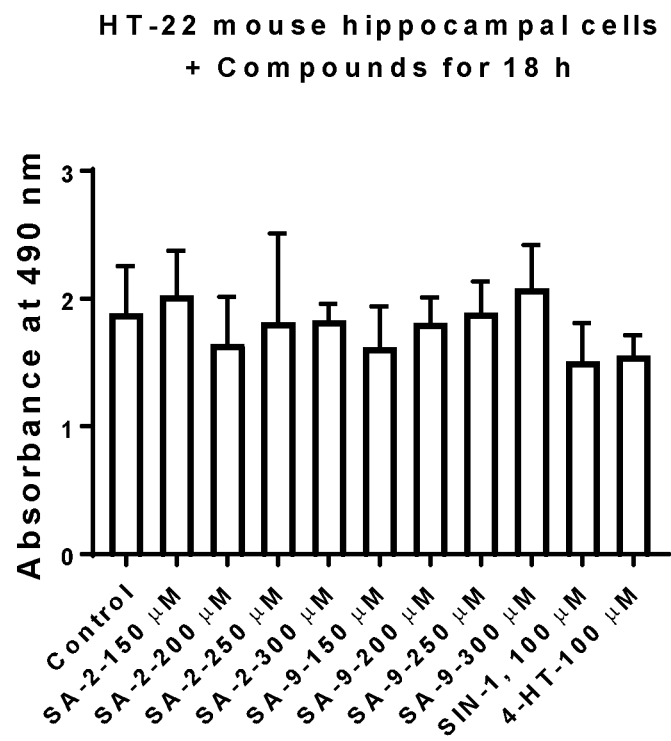
FIG. 14 shows the assessment of cytotoxicity of SA-2 and SA-9 in mouse hippocampal neural cells (HT-22) at different concentrations. SA-9 is not toxic to neural cells.

In hippocampal neural cells, the inventor sees a dose dependent increase in cell proliferation with different doses of SA-9 (FIG. 14) treatment where SA-2 didn't show such trend.

Figure 16:
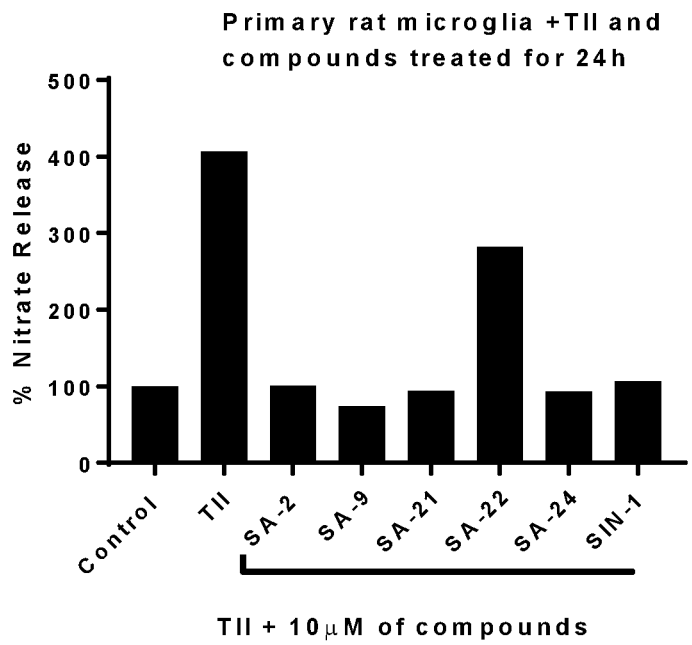
FIG. 16 shows upon treatment with a cocktail of inflammatory cytokines TII (TNF-α, IL-1β and IFN-γ) to primary microglia isolated from rat retina for 1 h, there is substantial production of nitric oxide as measured by Greiss assay. Treatment with 10 µM of SA compounds for 24 h reduced significantly the nitrite production indicating decrease in nitrosative stress.
Figure 17:
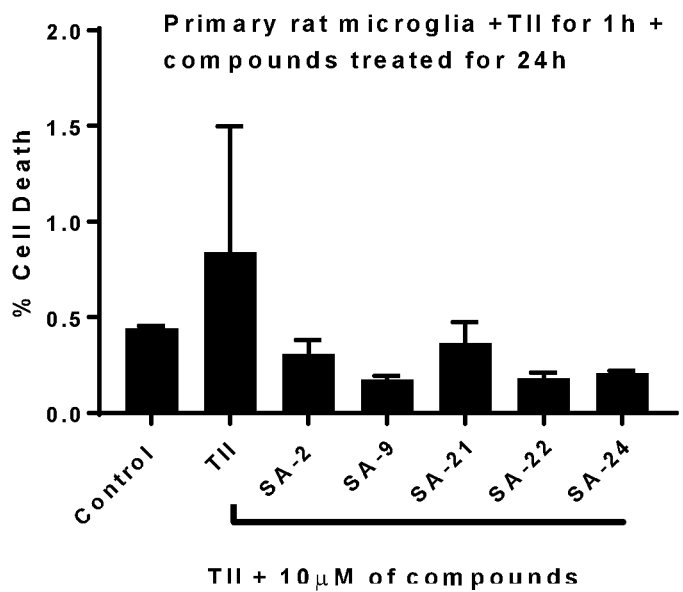
FIG. 17 shows upon treatment with a cocktail of inflammatory cytokines TII (TNF-α, IL-1β and IFN-γ) to primary microglia isolated from rat retina for 1 h, there is substantial amount of cell death followed by release of LDH. Treatment with 10 µM of SA compounds for 24 h reduced significantly the LDH production indicating neuroprotective activity.

The compounds of current invention SA-9, SA-10, SA-21, SA-22, and SA-24 did not activate rat primary microglia by themselves, and able to decrease the TII (a cocktail of inflammatory cytokines TNF-α, IL-1β, IFN-γ used to activate microglia) induced ROS and nitric oxide production and decrease the cell death as shown by DCFDA, Greiss and LDH assays respectively (FIGS. 15-17).

B. In Vivo Assay

Free compound SA-10 as well as PLGA nanoparticle encapsulated SA-10-NP increase new blood vessel formation and blood circulation in mouse leg after artery occlusion assessed by physical exercise in treadmill. Study groups and dosing paradigm evaluated by mouse treadmill are shown in Table 1.

TABLE 1

Study groups and doses

| Groups | | mg/kg | In vitro concentration | In vitro (μg/mL) | ratio w/w | final ratio | Animal dose (mg/kg) | Animal weight (g) | Treatment (μg) | Injection vol (mL) |
|---|---|---|---|---|---|---|---|---|---|---|
| Positive | VEGF | 0.025 | 0.025 μg/mL | 0.025 | 1 | 1 | 0.025 | 30 | 0.750 | 0.1 |
| Negative | Saline | 0 | | | | | | 30 | — | 0.1 |
| free drug | SA-10 | no data | 0.05 + 0.5 μM | 0.0125 + 0.125 | 0.5 + 5 | 5 | 0.125 | 30 | 3.750 | 0.1 |
| NPs | SA-10 NPs | no data | | | | | 10.000 | 30 | 300 | 0.1 |

Parameters: Incline 30 degrees; max endurance test at 50 cm/s or 30 m/min; stimulation: 1.5 mA. Stimulation and distance count were stopped when a mouse met one of the following conditions: 1) total stimulation time 30 seconds; or 2) single stimulation time is more than 10 seconds.

Figures 8A, 8B:
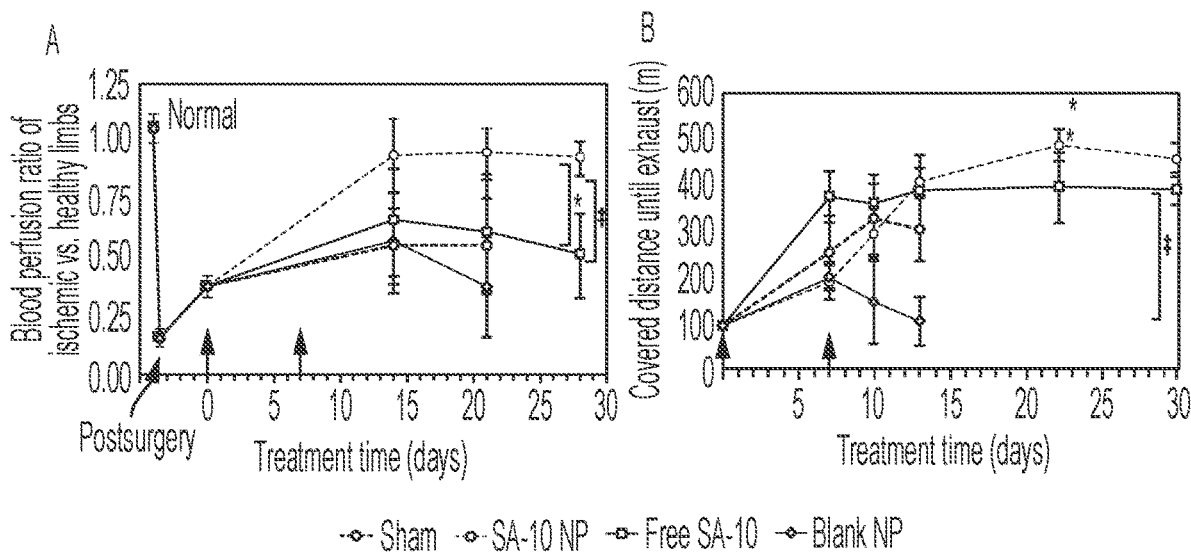
FIGS. 8A & 8B show physiological (FIG. 8A) and physical (FIG. 8B) recovery of PAD models under treatment of free SA-10 and SA-10 NPs. Animals were ligated to be hind limb (HL) ischemic, rested for three days before randomly assigned into treatment groups. Free drug and NPs were dosed to have the same amount drug of 0.125 mg/kg. Blank vehicles were injected at the same amount to that of SA-10 NPs (16 mg/kg). Sham group was treated with saline only (Table 1). All treatments were administered via intramuscular (IM) injection. The treatments were applied on day 0 and day 7 (Vertical black arrows). Blood perfusion was measured on Laser Speckle Contrast Imaging and quantified as ratio of blood indexes on ischemic versus normal limbs of the same animal. Exhaustion test was quantified as ability of animal to walk (in distance length) on treadmill until the animals exhausted (Table 2). * and ‡ indicated significant difference (P<0.05; n=5) versus Sham and blank vehicles, respectively.

The results of the mouse treadmill experiments are shown in FIG. 8B. Sham and blank NPs has no recovery effects.

Free SA-10 exhibited good recovery effects vs. sham and VEGF. SA-10 NP exhibited slow recovery, which, without wishing to be bound by any particular theory, may be due to slow release of compound at initial time points.

Figures 9A, 9B:
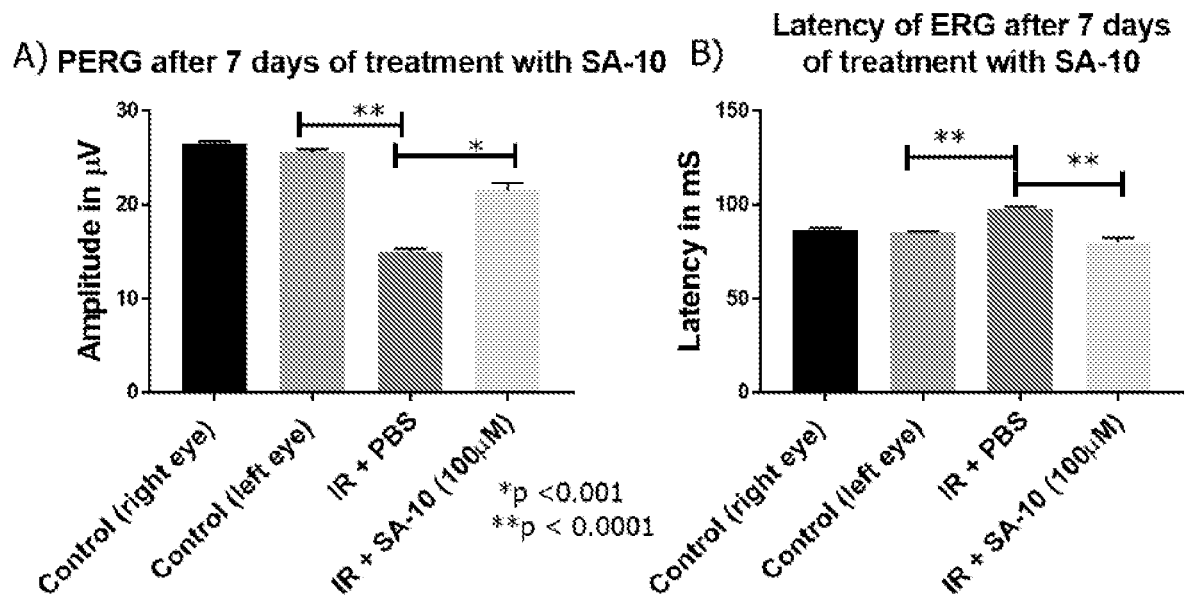

Compound SA-10 was also shown to be protective to retina after ischemia reperfusion injury in mice eyes. The function of retinal ganglion cells (RGCs) can be non-invasively assessed by pattern electroretinogram (PERG) a technique that emphasizes the activity of inner retina neurons. The amplitude of PERG reflects the degree of apparent damage by RGCs. A murine model of ocular stroke was employed to evaluate the function of RSCs upon administration of SA-10. After a single intravitreal injection of 100 µM of SA-10 to the left eye of mice (C57BL/6J, 12 weeks old, female) having undergone ischemia reperfusion (I/R) procedure, standard PERG was analyzed 1 week post I/R to determine whether compound SA-10 could prevent PERG deficits (FIGS. 9A & 9B). Analysis of mice exposed to I/R and co-treated with SA-10 (100 µM) showed significant difference compared to PERG amplitudes from I/R+PBS treated mice. Control mice not exposed to cannulation of anterior chamber did not display any evidence of functional RGC deficits at 1 week (26.7±0.7 µV, n=5) after operation. However, there was a significant decrease in PBS treated mice compared to PERG amplitudes from sham mice (14.8±1.4 µV, n=5). As expected, compound SA-10 injection increased PERG amplitude compared to PBS-treated I/R mice (21±1.4 µV, n=5, p<0.05 vs. I/R+PBS treated mice; values signify mean±SEM).

Figure 9C:
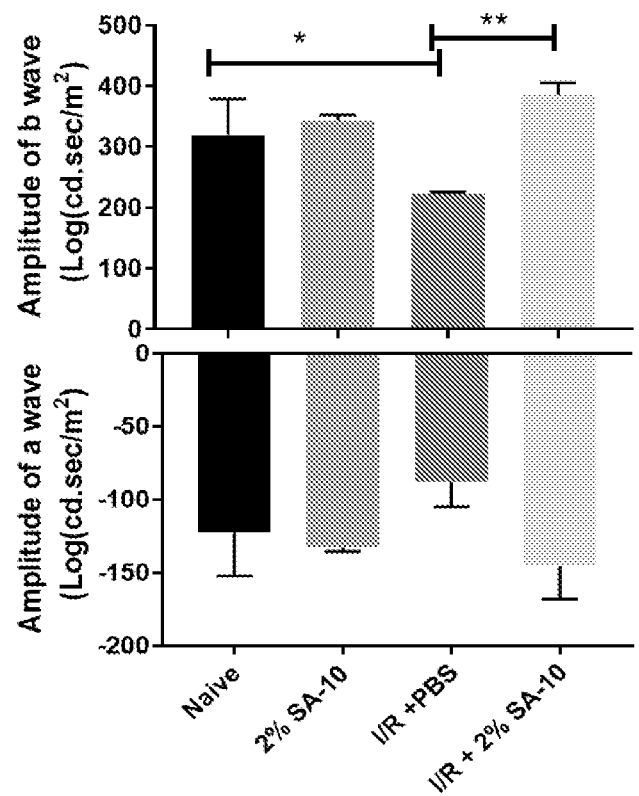
Figures 11A, 11B, 11C, 11D:
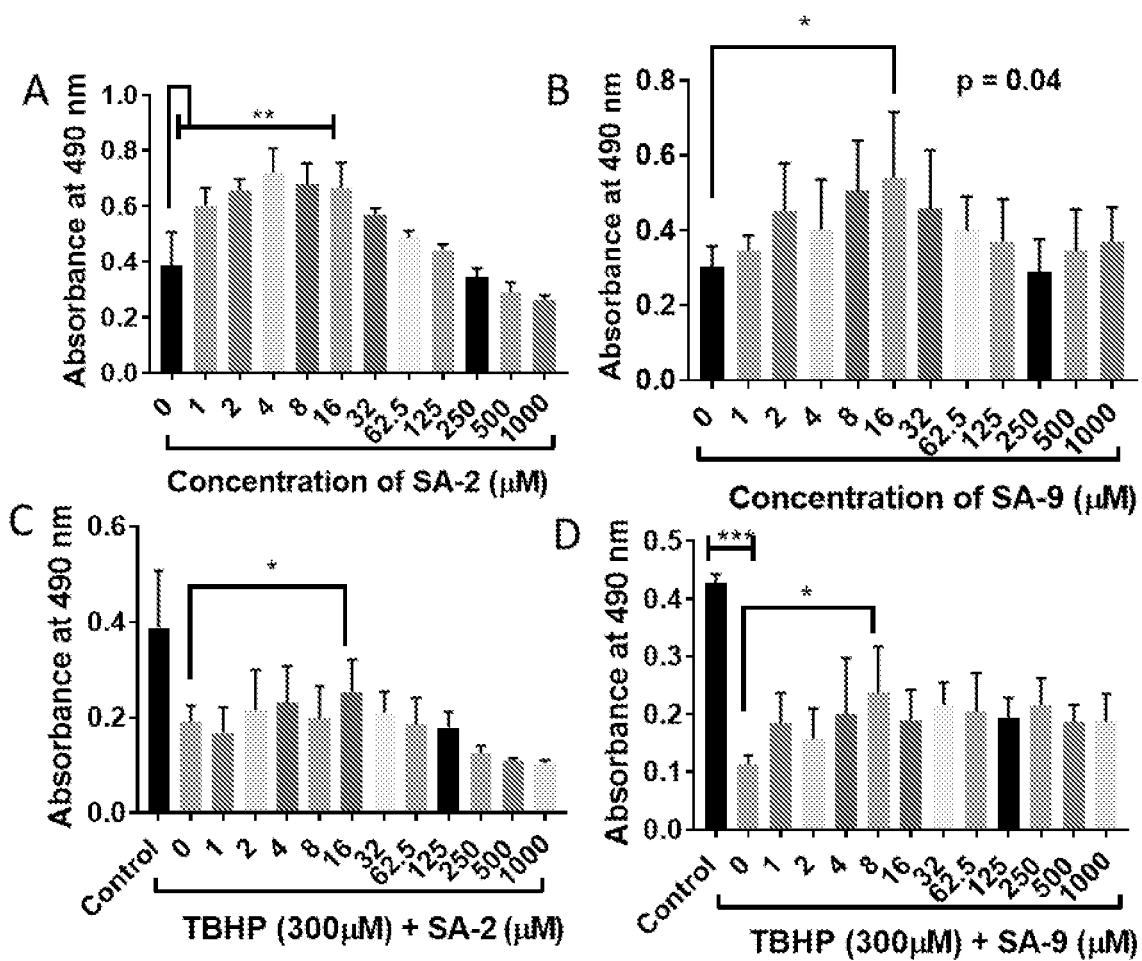
FIGS. 11A-11D show enhanced biological properties of SA-9.
Figure 12:
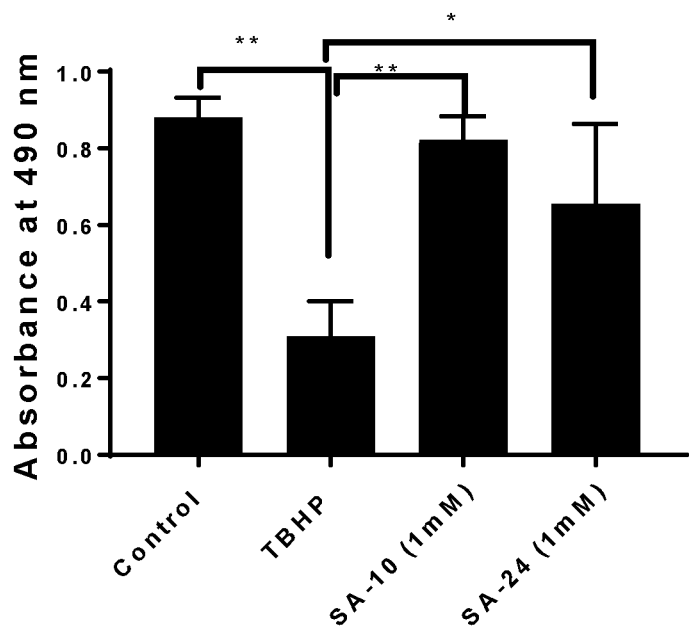
FIG. 12 shows the cytoprotective activity of SA-10 and SA-24 in human trabecular meshwork cells under TBHP (300 µM) induced oxidative stress condition.
Figure 13:
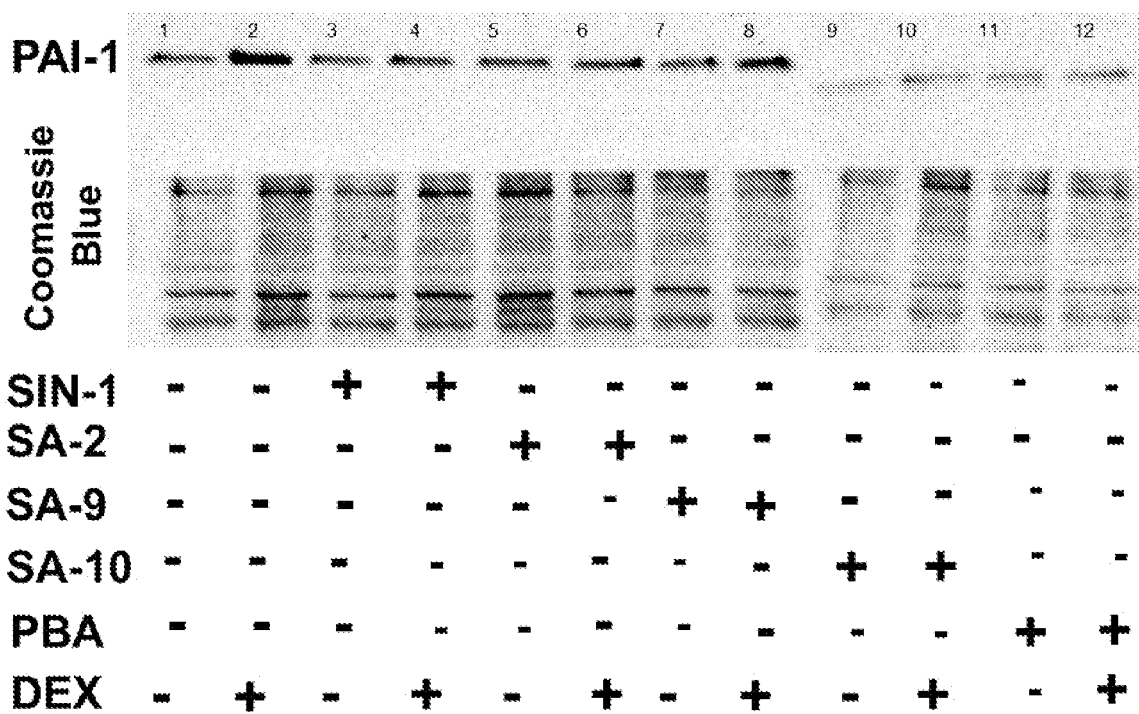
FIG. 13 shows that compound SA-10 decrease dexamethasone (DEX) induced increase in plasminogen activating inhibiting (PAI-1) enzyme in human trabecular meshwork cells. SIN-1 is a standard NO donor and phenyl butyric acid (PBA) is positive control.

Studies of retinal ischemia/reperfusion indicate a significant reduction in the amplitude of the scotopic b-wave of the electroretinogram (ERG) as shown in FIG. 9C (I/R+PBS) which is due to loss of photoreceptor as well as bipolar cells (Sun et al., 2007). Compound SA-10 significantly reversed these damages which is further confirmed from the maintenance of retinal layer thickness as measurement by SD-OCT (FIG. 9D).

Figure 18:
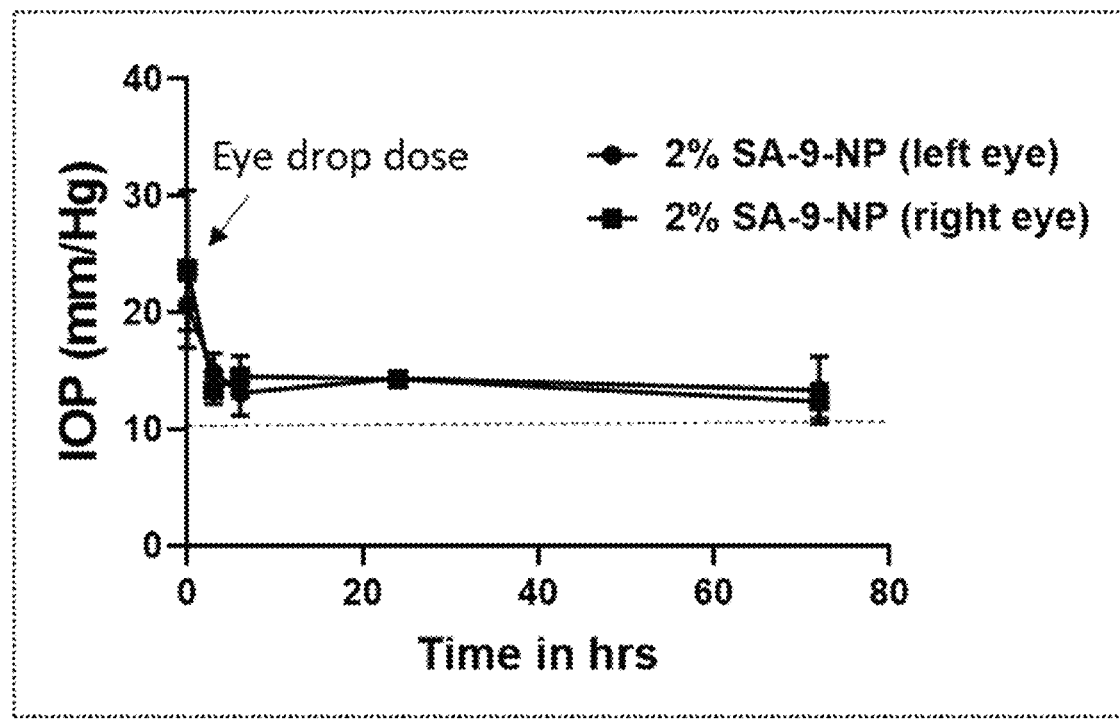
FIG. 18 demonstrated the intraocular pressure lowering ability of SA-9 NP in DEX induced mouse model of ocular hypertension modelling glaucoma. N=5.

In a dexamethasone induced ocular hypertension mouse model previously published by Zode et al. (2017) mimicking glaucoma, the inventor sees significant drop in intraocular pressure in both of the mouse eyes (FIG. 18). Briefly, after periocular injection of DEX acetate once a week for four weeks, the inventor observes increase in IOP (FIG. 18) as compared to the baseline. For this study, anesthetized IOPs were measured during day (dim light) and night, respectively using a TonoLab rebound tonometer (Colonial Medical Supply, Franconia, NH) every week. SA-9 NP (2% w/v saline suspension) was administered as single eye drop (30 µl) in both eyes and IOP was measured at different time points. The inventor sees significant IOP reduction at 3 h post dose and effect lasting >72 h. N=5, C57BL6 mouse (12 weeks old) were used for this study.

Example 3: Use of SA-10 to Treat Ocular Stroke

In vitro Nitric oxide synthetase (NOS) activating activity. Human Umbilical Vascular Endothelial Cells (HUVECs) were plated at a density of $2\times10^5$ cells per well and were treated with or without $H_2O_2$ (200 µM) and compounds at different concentrations. NOS knock-down samples (NOSi) were cells exposed to a competitive NOS inhibitor L-NNA at 50 µM. After 24-hour-treatment, total NOS activity from treated cells was quantified using OxiSelect™ Intracellular Nitric Oxide (NO) Assay Kit where NOS activity correlates to fluorescent intensity[5].

In vitro cytoprotective activity. HUVEC Cells were co-treated with or without $H_2O_2$ (200 µM)[5] and the test compounds (0.05 µM-100 µM). After 24 hours of treatment, cell proliferation was measured using MTT assay. All the experiments are done in duplicate with four experimental replicates.

In vitro plasminogen activating inhibitor-1 (PAI-1) activity. Human primary trabecular meshwork (hTM) cells were plated in 6-well plates at a density of $2\times10^5$ cells per well and were treated with dexamethasone (DEX, 100 nM) or vehicle (ethanol) in the presence of test compounds (100 µM) for 48 hr. Conditioned medium was collected for Western Blot. Experiments were performed in triplicates (n=5).

Ischemic/reperfusion injury model in mouse eyes. Mice (C57Bl6/J, 12 weeks, n=5) were anesthetized and the ischemic/reperfusion (I/R) injury was performed on left eye after it was numbed with proparacaine followed by intravitreal injection of 2 µl of 2% of compound SA-10 formulated in PBS (I/R+SA-10 group) or only 2 µl PBS to left eye (I/R+PBS group) at days 0. At day 7, pattern ERG was performed with the JORVEC System. SD-OCT was done to measure the change in overall thickness of retina layers and flash ERG was done to measure the function of bipolar cells (b-wave) as well as photoreceptor cells (a-wave) after 28 days. Pattern ERG was performed to measure the function of RGCs. Right eye was served as contralateral control.

Results:

Compound SA-10 decreased DEX induced increase in PAI-I level in hTM cells and are cytoprotective to HUVEC from oxidative stress. Compound SA-10 after single intravitreal injection was protective to retina against ischemic stroke followed by reperfusion induced chronic neural cell death. Intravitreal dosing of 2% of SA-10 doesn't cause any significant protein nitrosylation in retina indicating a safety dose. Data shown in FIGS. 9A-9D.

1. Materials & Methods

Chemicals and reagents. Compound SA-10 and SA-2 were synthesized by the inventor.

Fabrication of SA-10 NPs. SA-10 loaded PLGA NPs were prepared using the standard single emulsion technique developed in the inventors' laboratory. In brief, 10 mg of SA-10 was dissolved 10 µl DMSO and then transferred to 3 ml of chloroform containing 90 mg of PLGA to form an oil phase. This solution was then added dropwise into 20 ml of 5% PVA solution (water phase) followed by sonication at 40 W for 10 minutes to form the SA-10 loaded NPs. The emulsion was stirred overnight to completely evaporate the organic solvent. Next, the NPs were pelleted by ultracentrifugation at 25000 rpm for 30 minutes followed by washing twice with DI water. Finally, NP pellet was dissolved in DI water and lyophilized to obtain a powder form.

Characterization of SA-10 NPs. Standard solutions of SA-10 were prepared, scanned and obtained absorbance values at 240 nm. From these, a linear fit was obtained to calculate loading efficiency, drug content and drug release profile of SA-10 NPs following reported protocol (Le et al., 2017).

For the drug release study, four separate solutions at 5 mg/mL of SA-10 NPs in PBS (pH 7.4) were placed in a dialysis bag with MWCO 3.5-5 kDa (Spectrum, Catalog 131192), submerged in 20 mL PBS 1×pH 7.4 (so-called dialysate) and incubated at 37° C. over a time range. At each time point, 1 mL of dialysate solution was pooled and replaced with the same volume of fresh PBS. Each sampling solution was then read for its absorbance value and the amount of released SA-10 was quantified against the SA-10 standard curve. Consequently, a cumulative release profile of SA-10 over time was plotted.

Doses and groups of study. For comparison, the same concentrations of SA-10 (0.05 µM, 0.5 µM and 5 µM) were used in these studies. For all studies unless otherwise mentioned, the no treatment group (N/T) was cells exposed to $H_2O_2$ only, while cells grown in complete media without exposure to anything served as a control group.

Cellular stress conditions. Except cell protection study where 400 µM $H_2O_2$ was applied in 24 hours, all other in vitro studies 200 µM $H_2O_2$ was used to avoid biased results due to the cell death. All treatments were dissolved in low serum media (basal media with growth factors and 0.2% FBS) except positive control that used complete media (basal media with growth factors and 2% FBS). No treatment groups had cells exposed to stress without any treatment added.

Cell migration studies. Transwell chemotaxis migration studies were conducted to study effects of SA-2 and SA-10 drugs on the migration of endothelial cells under stress conditions. To this, ECs were seeded at 50,000 cells/cm² on upper compartment (low serum media with 200 µM $H_2O_2$) and attracted to migrate through 8 µm-pore membrane by chemotaxis (SA compounds dissolved in low serum media with 200 µM $H_2O_2$) added in lower compartment. At 12 hours, migrated cells were fixed with 4% paraformaldehyde and stained with crystal violet prior to imaging and counting by Cell counter on ImageJ.

Cell proliferation studies. Cells were seeded at 10,000 cells/cm² and allowed to grow in several days. Stresses (200 µM $H_2O_2$) and test compound at concentration of 0.05 µM, 0.5 µM and 5 µM were refreshed every 24 hours. Cell number were quantified at day 4 using DNA assays and calculated against standard curve of DNA, which is converted to the correlated cell number.

In vitro angiogenesis studies. Cultrex reduced growth factor basement membrane extracted gel (Cat. 3433-005-01, R&D Systems, Inc.) was coated on bottom of µ-Slide angiogenesis wells (Cat. 81506, iBidi GmbH Co.). ECs at early passages (passage $6^{th}$ or earlier) were then seeded on gel at a seeding density of 25,000 cells/cm². Next, cells were treated with treatment groups (SA-2, SA-10, SA-10 NPs, VEGF) under stress condition (200 µM $H_2O_2$). After 12 hours of incubation, formation of new microtubes were visualized and captured on phase contrast microscopes. Images were then stacked and processed with Angiogenesis analyzer on ImageJ.

Animal model. Since PAD happens commonly in old people, the inventor used old mice for ischemic hindlimb animal models. To this, male and female Balb/c mice at age of 30-40 weeks old were chosen for these in vivo studies. Animals were housed in individual cage at normal diet before performing ligation. In brief, animals were anesthetized with 2% isoflurane, and prior to incision, analgesic SR Buprenorphine was injected subcutaneously (at dose of 1 mg/kg for mice). Upon opening the incision on animals left legs, the membrane covering the inguinal fat tissue was carefully separated to expose the neurovascular bundle underneath and veins and nerves were then carefully separated from arteries. Next, three pair of 1 mm-distal ties (using 6-0 or 7-0 nonabsorbable suture) followed by transection (by spring scissor) were made on femoral artery, proximal caudal femoral artery and superficial caudal epigastric artery. Finally, the incision was closed by absorbable 5-0 or 6-0 sutures. The animal model appeared limping similar to literature report[37] from the time post-treatment until endpoint study.

Therapeutic groups of study and sample size. After 3 days of ligation, mice were randomly assigned into 4 groups: Sham, free SA-10, SA-10 NPs and blank PLGA NPs. Sham groups were injected with saline without any therapeutic treatment. Based on study of biodistribution, the route of administration was intramuscular (IM) injection. To determine sample size, a power of analysis was processed on SigmaPlot v.13 software. Significant difference would be considered when P<0.05. Based on the inventor's own experience and literature reports, the inventor selected power with α<0.05 as 0.8. Calculation yielded sample size as n=5.

In vivo blood perfusion and physical test. Animals under treatments were measured for their recovery physiologically and physically. In the former study, animals were anesthetized with 1.5-2% isoflurane, and blood perfusion was measured with Laser Speckle Contrast Imaging (PeriCam PSI NR, Perimed AB). Briefly, hemoglobin in shallow vessels and capillaries responded to exciting lasers in term of color pigments. The relative blood perfusion was calculated by device software (PIMSoft), and it correlated to typical pigments. To obtain consistent and precise comparison among animals, blood perfusion indexes of each animal were obtained from ratio of relative blood perfusion of ischemic limb to that of healthy limb on the same animal. In the later study, animals after treatment were placed in individual lanes of a mice treadmill (Cat. LE8710MTS-5 lanes. Harvard Apparatus). The treadmill was set at 30-degree inclination. Next, the animals were then stimulated with 1.5 mA electrical shocks to keep running while the treadmill speeded up as shown below:

TABLE 2

Maximal endurance protocol to test ability to walk of animals on treadmill.

| Start speed (cm/s) | End speed (cm/s) | Duration (mm:ss) | Stimulation (mA) | Period name |
|---|---|---|---|---|
| 5 | 10 | 0:30 | 1.5 | Initial speed |
| 10 | 10 | 0:30 | 1.5 | Stable warm up speed |
| 10 | 15 | 0:30 | 1.5 | Speed up 1 |
| 15 | 15 | 0:30 | 1.5 | Stable low speed |
| 15 | 20 | 1:00 | 1.5 | Speed up 2 |
| 20 | 20 | 1:30 | 1.5 | Stable high speed |
| 20 | 25 | 1:30 | 1.5 | Start challenge |
| 25 | 25 | 2:00 | 1.5 | Sign of tiredness |
| 25 | 30 | 2:00 | 1.5 | Challenging endurance |
| 30 | 30 | 5:00 | 1.5 | Endurance phase 1 |
| 30 | 40 | 2:30 | 1.5 | Challenging |
| 40 | 40 | 5:00 | 1.5 | Endurance phase 2 |
| 40 | 50 | 2:30 | 1.5 | Reaching limits |
| 50 | 50 | 5:00 | 1.5 | Physically endure |

When the animal was not running for total of 30 seconds under stimulation, the run of animals was terminated from recording. Physical recovery of animals was then quantified as covered distance until exhaustion, which was obtained from the treadmill software.

Statistical analysis. All the experiments were performed with n=3÷6. Data were expressed as mean±SEM. The statistical analysis was assessed using ANOVA followed by post hoc Pairwise Multiple Comparisons using Holm-Sidak method on SigmaPlot version 13.0. A significant difference was considered where P values appeared ≤0.05.

2. Results

Figure 19:
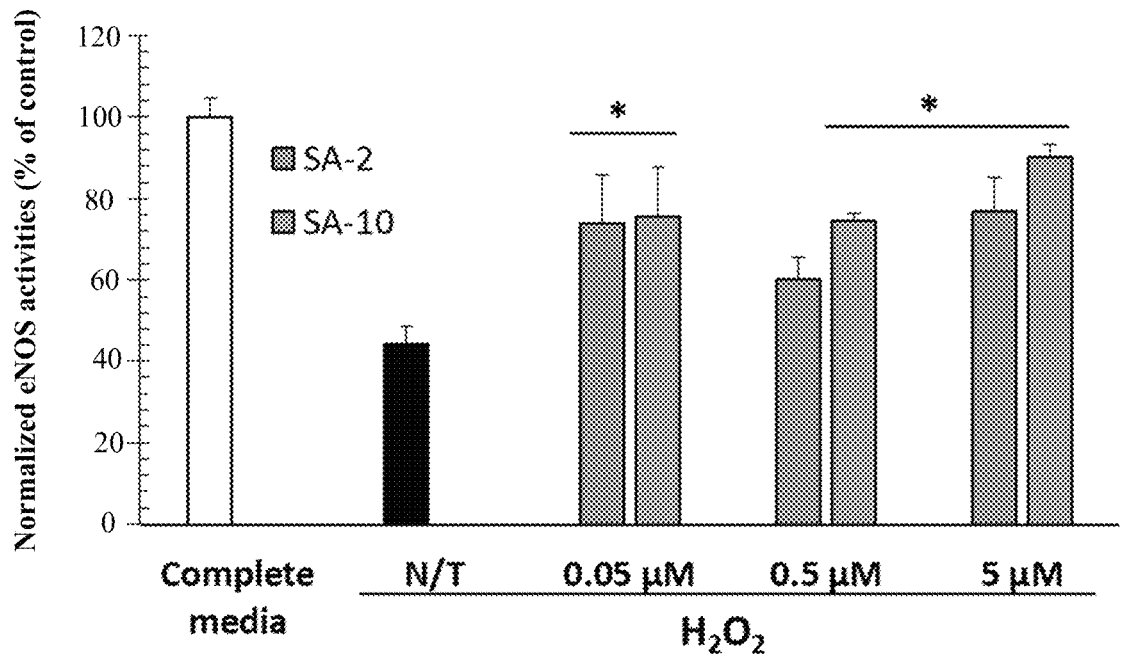
FIG. 19 demonstrated the eNOS activating activity of SA-10 at different concentrations under $H_2O_2$ induced oxidative stress condition and compared with a control compound SA-2.

Effects of SA-10 free drug to EC functions in comparison to SA-2. The new drug SA-10 was tested for its abilities to protect ECs. Unlike SA-2 that had a narrow effective range of concentration up to 1 µM, SA-10 provided a wider range up to 100 µM (FIG. 3), exhibiting that this new hybrid compound was more potent than the previous published drug SA-2. The EC functions on regulating eNOS were also studied by SA-2 and SA-10, and it showed that both drugs were successfully maintained EC viability and induced eNOS signals under stress conditions (FIG. 19).

Figure 3:
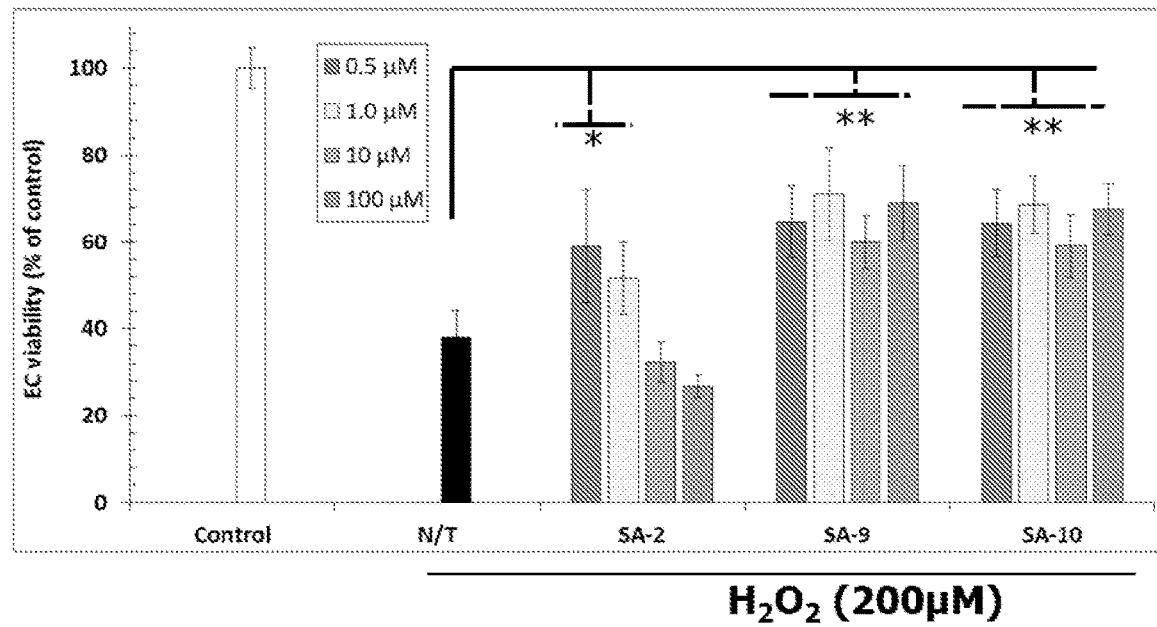
FIG. 3 shows the effects of SA-9 and SA-10 on HUVEC viability under $H_2O_2$ induced oxidative stress conditions after 12 h of treatment. n=4, *p<0.05; **p<0.001 by two-way ANOVA.

Effects of SA-10 loaded NPs on EC functions. SA-10 was further tested on ECs to evaluate if it enhanced the responses of EC under stress conditions. First, a longer protection study was performed (FIG. 4) and it showed that ECs were protected over the course of 2-day stress with 400 µM $H_2O_2$. SA-10 also performed comparably to SA-2 in term of induce EC migration at a concentration equal to the optimal concentration of SA-2 (FIG. 3). As ECs were found to be induced their viability, migration and proliferation, it was important to study if ECs were able to form new blood vessels. This process was investigated using a 2D culture in angiogenesis study, quantifying for the formation of new microtubes. Interestingly, SA-10 significantly induced tube formation by ECs under stress conditions. This was significantly higher than that of no treatment group and comparable to free VEGF under stress and healthy cells under no stress (FIG. 5).

Figures 20A, 20B:
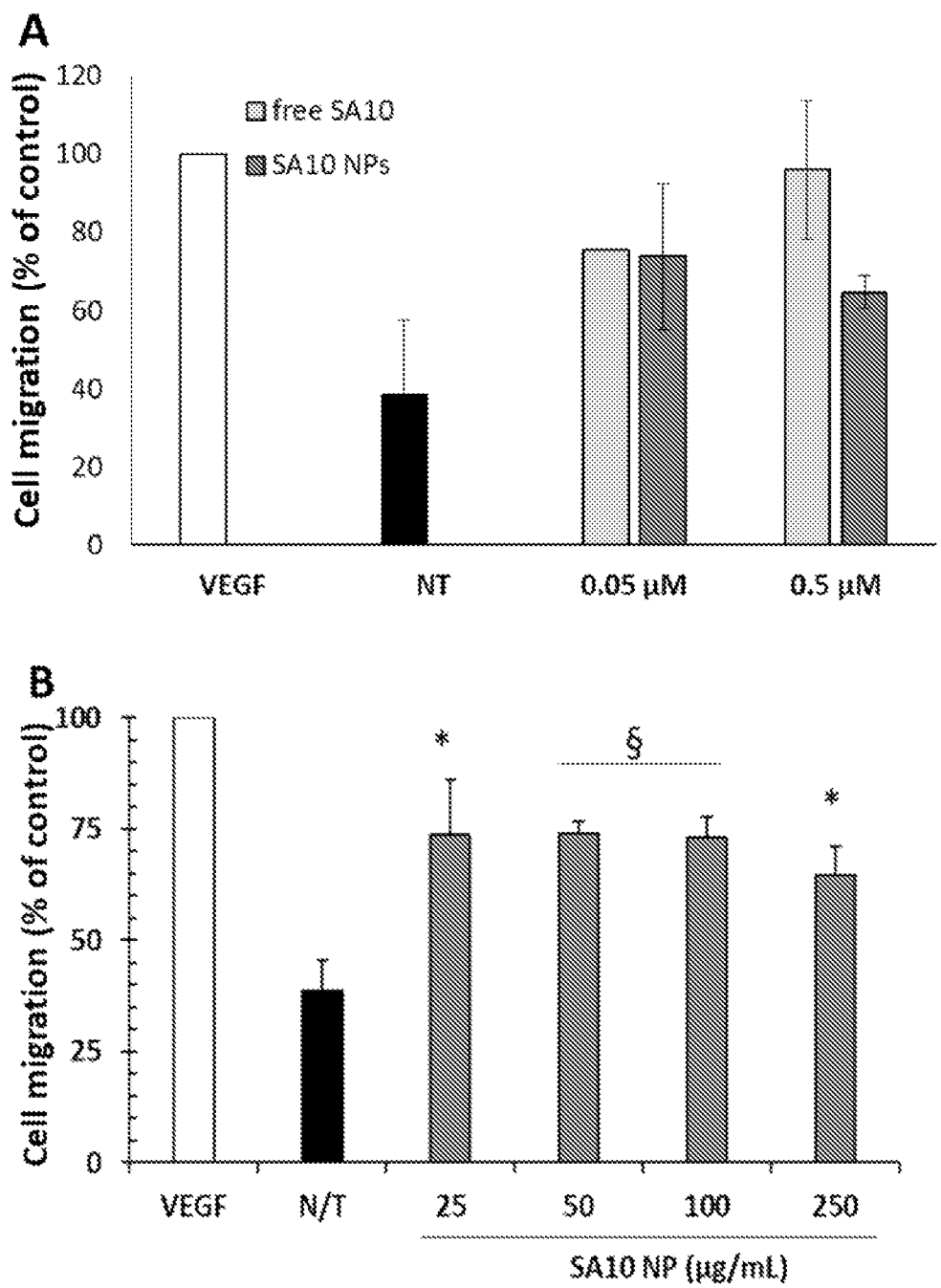
FIGS. 20A & 20B demonstrated the migration of endothelial cells after stress in a transwell chemotaxis migration

SA-10 has proved its potency in protecting endothelial cells, inducing proliferation and forming of new blood vessels in vitro, it was needed to package in nanoparticles to provide longer therapeutic efficacy and a controlled delivery lately. SA-10 was loaded in PLGA NPs. The PLGA NPs had the drug content of 25 µg SA-10 per mg of NPs. A drug release profile was plotted, giving a biphasic release where 30% of drugs was released in the burst phase while a sustained release of drugs was observed up to 80% at 5 days (FIG. 7). Migration study also showed that SA-10 loaded PLGA NPs facilitated EC migration. The highest effect was obtained at a concentration of 25 µg/mL (FIG. 20B).

A biodistribution study was conducted to determine the best route for administration. It was determined that IM administration was the best route for study of therapeutic efficacy of SA-10 loaded NPs.

Dose dependent therapeutic effects in vivo. Several doses of SA-10 loaded NPs were used to test for recovery of animals in PAD events.

The NPs at doses 0.125 mg/kg and 0.25 mg/kg consistently improved the treatment over the time. It might be possible that higher doses (>2 mg/kg) may not be effective. Therefore, a lower but effective dose of 0.125 mg/kg was chosen for more comprehensive investigation in later studies.

Physiological and physical recovery. As shown in FIGS. 8A & 8B, the SA-10 NPs performed better than sham and blank vehicles either in term of blood perfusion indexes or endurance run. Free drug performed better than sham and blank vehicle at the beginning when animals were repeated the doses; however, as animals were not given another dose, the recovery was decreased. Meanwhile, the NPs, given by biodistribution study that they stayed long in the muscles, sustained release SA-10 and provided therapeutic effects to the animals.

All of the compounds, formulations, and methods disclosed and claimed herein can be made and executed without undue experimentation in light of the present disclosure. While the compounds, formulations, and methods of this disclosure have been described in terms of preferred embodiments, it will be apparent to those of skill in the art that variations may be applied to the compounds, formulations, and methods, as well as in the steps or in the sequence of steps of the method described herein without departing from the concept, spirit, and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references to the extent that they provide exemplary procedural or other details supplementary to those set forth herein, are specifically incorporated herein by reference.

Anderson, *Practical Process Research & Development—A Guide for Organic Chemists*, $2^{nd}$ ed., Academic Press, New York, 2012.
*Handbook of Pharmaceutical Salts: Properties, and Use*, Stahl and Wermuth Eds., Verlag Helvetica Chimica Acta, 2002.
Reagan-Shaw et al., *FASEB J.*, 22(3):659-661, 2008.
Smith, *March's Advanced Organic Chemistry: Reactions, Mechanisms, and Structure*, $7^{th}$ Ed., Wiley, 2013.
Acharya et al., *Bioorg Med Chem Lett*, 26(5): 1490-1494, 2016.
Camci-Unal et al., *Polym Int*, 62(6):843-848, 2013.
Chen et al., *Stroke*, 42(8):2229-2234, 2011.
Chiou, *Annals N.Y. Acad. Sci.*, 215:113-116, 1999.
Cugati el al., *Curr. Treatment Options Neurol.*, 15:63-77, 2013.
de Leur et al., *World J. Surg.*, 36(12):2937-2943, 2012.
Feltgen et al., *Graefe's Arch. Clin. Exper. Ophthalmol.*, 244(8):950-956, 2006.
Fokkema et al., *J. Vasc. Surg.*, 64(1):104-108.e101, 2016.
Fraser and Adams, *Cochrane Database Systematic Rev.*, 1:CD001989, 2009.
Garg et al., *Arterioscler. Thromb. Vasc. Biol.*, 36(4):750-756, 2016.
Go et al., *Circulation*, 129(3):e28-e292, 2013.
Griendling et al., *Circulation Research*, 1994, 74, 1141-1148.
Grochot-Przeczek et al., *Gene*, 525(2):220-228, 2013.
Hackl et al., *Vasc. Endovasc. Surg.*, 49(7): 160-165, 2015.
Kernt et al., *J Glaucoma*, 22(5):404-412, 2013.
Le et al, *Nat. Sci. Rep.*, 7(1):8692, 2017.
Mayo et al., *J. Cereb. Blood Flow Metab.*, 32(5):825-834, 2012.
Moreno et al., *Free Rad. Biol. Med.*, 37(6):803-812, 2004.
Munemasa et al., *Gene Ther.* 16(1):17-25, 2009.
Newhall et al., *Ann. Vasc. Surg.*, 30:292-298.e291, 2016.
Reinecke et al., *Eur. Heart J.*, 36(15):932-938, 2015.
Sun et al., *J. Comparative Neurol.*, 505(1): 131-146, 2007.
Toda et al., *Prog. Retinal Eye Res.*, 26:205-238, 2007.
Whitehill, *Vasc. Med.*, 2(3):252-256, 1997.
Yokoyama et al., *Biochem. Biophys. Res. Commun.*, 451(4): 510-515, 2014.

What is claimed is:

1. A compound of the formula:

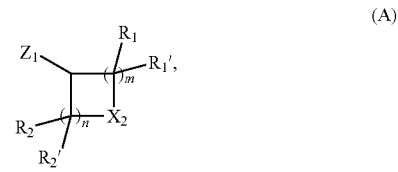

(A)

wherein:
n and m are each independently 0, 1, 2, 3, or 4;
$Z_1$ is
a group of the formula:

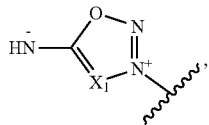
(A1)

wherein:
$X_1$ is $=CR_{x1}-$ or $=N-$ wherein,
$R_{x1}$ is hydrogen, alkyl$_{(C \leq 12)}$, or substituted alkyl$_{(C \leq 12)}$;
$X_2$ is $-O-$, $-S-$, $-S(O)-$, or $-S(O)_2-$;
each instance of $R_1$, $R_1'$, $R_2$, and $R_2'$ is independently hydrogen, hydroxy, amino, nitro, cyano, halo, carboxyl, carbamoyl, mercapto, $-S(O)_2OH$, or $-S(O)_2NH_2$; or alkyl$_{(C \leq 12)}$, acyl$_{(C \leq 12)}$, alkoxy$_{(C \leq 12)}$, alkylamino$_{(C \leq 12)}$, dialkylamino$_{(C \leq 12)}$, amido$_{(C \leq 12)}$, acyloxy$_{(C \leq 12)}$, or a substituted version of any of these groups; or $-C(O)R_b$, wherein:
$R_b$ alkoxy$_{(C \leq 12)}$, alkylamino$_{(C \leq 12)}$, or dialkylamino$_{(C \leq 12)}$; or
provided the sum of n and m is 1, 2, 3, 4, 5, or 6; or
a compound of the formula:

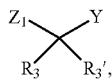
(B)

wherein:
$Z_1$ is as defined above;
$R_3$ is alkyl$_{(C2-12)}$, aralkyl$_{(C \leq 12)}$, heteroaralkyl$_{(C \leq 12)}$, -alkanediyl$_{(C \leq 12)}$-NHC(NH)NH$_2$, or a substituted version of any of these groups;
$R_3'$ is hydrogen; or
$R_3$ and $R_3'$ are taken together and are -alkanediyl$_{(C \leq 12)}$-$X_3-$, substituted -alkanediyl$_{(C \leq 12)}$-$X_3-$, -alkanediyl$_{(C \leq 6)}$-$X_3$-alkanediyl$_{(C \leq 6)}-$, or substituted-alkanediyl$_{(C \leq 6)}$-$X_3$-alkanediyl$_{(C \leq 6)}-$, wherein:
$X_3$ is $-O-$, $-NR_a-$, $-S-$, $-S(O)-$, or $-S(O)_2-$, wherein:
$R_a$ is hydrogen, hydroxy, or oxyl radical; or alkyl$_{(C \leq 12)}$, aralkyl$_{(C \leq 12)}$, acyl$_{(C \leq 12)}$, or a substituted version of any of these groups; or
a group of the formula:

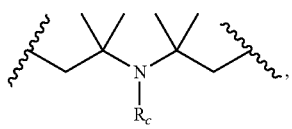
(IIa)

wherein:
$R_c$ is hydroxy or oxyl radical; and
Y is $-CO_2R_d$, or $-C(O)NR_dR_e$, wherein:
$R_d$ is hydrogen; or
alkyl$_{(C \leq 12)}$, cycloalkyl$_{(C \leq 12)}$, heterocycloalkyl$_{(C \leq 12)}$, aralkyl$_{(C \leq 12)}$, aryl$_{(C \leq 12)}$, heteroaralkyl$_{(C \leq 12)}$, heteroaryl$_{(C \leq 12)}$, or a substituted version of any of these groups; or a group of the formula:

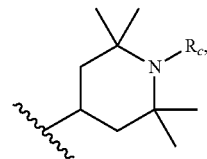
(IIb)

wherein $R_c$ is as defined above; or
a group of the formula:

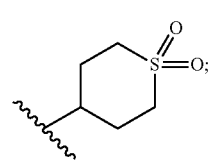
(IIc)

$R_c$ is hydrogen, alkyl$_{(C \leq 12)}$, or substituted alkyl$_{(C \leq 12)}$; or
a compound of the formula:

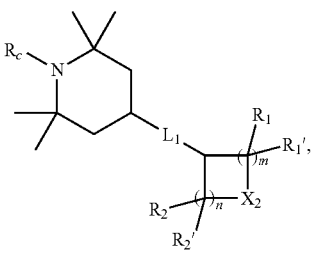
(III)

wherein:
n, m, $X_3$, $R_1$, $R_1'$, $R_2$, $R_2'$, and $R_c$ are as defined above; and
$L_1$ is
a group of the formula:

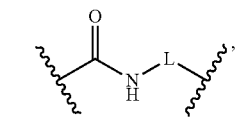
(IIIb)

wherein:
L is a covalent bond; or
a group of the formula:

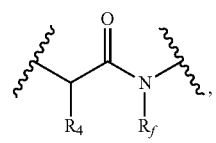
(IIIa)

wherein:
$R_f$ is hydrogen, alkyl$_{(C \leq 12)}$, or substituted alkyl$_{(C \leq 12)}$;

R$_4$ is hydrogen; or
alkyl$_{(C\leq 12)}$, aralkyl$_{(C\leq 12)}$, heteroaralkyl$_{(C\leq 12)}$, -alkanediyl$_{(C\leq 12)}$-ONO$_2$, or a substituted version of any of these groups;
provided the sum of n and m is 1, 2, 3, 4, 5, or 6; or
a compound of the formula:

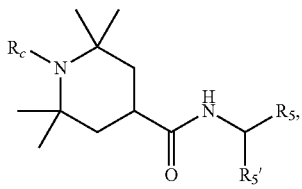

(IV)

wherein:
R$_c$ is as defined above;
R$_5$ is —CO$_2$R$_g$ or —C(O)NR$_h$R$_i$, wherein:
R$_g$ is hydrogen; or
alkyl$_{(C\leq 12)}$, substituted alkyl$_{(C\leq 12)}$, cycloalkyl$_{(C\leq 12)}$, or substituted cycloalkyl$_{(C\leq 12)}$;
R$_h$ and R$_i$ are each independently hydrogen; or
alkyl$_{(C\leq 12)}$, substituted alkyl$_{(C\leq 12)}$, cycloalkyl$_{(C\leq 12)}$, or substituted cycloalkyl$_{(C\leq 12)}$; and
R$_5$' is hydrogen; or
alkyl$_{(C\leq 12)}$, aralkyl$_{(C\leq 12)}$, heteroaralkyl$_{(C\leq 12)}$, or a substituted version of any of these groups;
or a pharmaceutically acceptable salt of any of these formulae.

2. The compound of claim 1 further defined as:

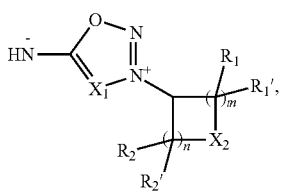

(I)

wherein:
n and m are each independently 0, 1, 2, 3, or 4;
X$_1$ is =CH— or =N—;
X$_2$ is —O—, —S—, —S(O)—, or —S(O)$_2$—;
each instance of R$_1$, R$_1$', R$_2$, and R$_2$' is independently hydrogen, hydroxy, amino, nitro, cyano, halo, carboxyl, carbamoyl, mercapto, —S(O)$_2$OH, or —S(O)$_2$NH$_2$; or
alkyl$_{(C\leq 12)}$, acyl$_{(C\leq 12)}$, alkoxy$_{(C\leq 12)}$, alkylamino$_{(C\leq 12)}$, dialkylamino$_{(C\leq 12)}$, amido$_{(C\leq 12)}$, acyloxy$_{(C\leq 12)}$, or a substituted version of any of these groups; or —C(O)R$_b$, wherein:
R$_b$ alkoxy$_{(C\leq 12)}$, alkylamino$_{(C\leq 12)}$, or dialkylamino$_{(C\leq 12)}$; or
provided the sum of n and m is 1, 2, 3, 4, 5, or 6; or
a compound of the formula:

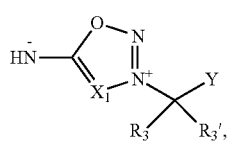

(II)

wherein:
X$_1$ is as defined above;
R$_3$ is alkyl$_{(C2-12)}$, aralkyl$_{(C\leq 12)}$, heteroaralkyl$_{(C\leq 12)}$, -alkanediyl$_{(C\leq 12)}$-NHC(NH)NH$_2$, or a substituted version of any of these groups;
R$_3$' is hydrogen; or
R$_3$ and R$_3$' are taken together and are -alkanediyl$_{(C\leq 12)}$-X$_3$—, substituted -alkanediyl$_{(C\leq 12)}$-X$_3$—, -alkanediyl$_{(C\leq 6)}$-X$_3$-alkanediyl$_{(C\leq 6)}$—, or substituted-alkanediyl$_{(C\leq 6)}$-X$_3$-alkanediyl$_{(C\leq 6)}$—, wherein:
X$_3$ is —O—, —NR$_a$—, —S—, —S(O)—, or —S(O)$_2$—, wherein:
R$_a$ is hydrogen, hydroxy, or oxyl radical; or
alkyl$_{(C\leq 12)}$, aralkyl$_{(C\leq 12)}$, acyl$_{(C\leq 12)}$, or a substituted version of any of these groups; or
a group of the formula:

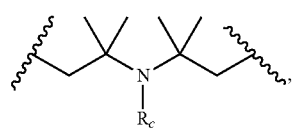

(IIa)

wherein:
R$_c$ is hydroxy or oxyl radical; and
Y is —CO$_2$R$_d$, or —C(O)NR$_d$R$_e$, wherein:
R$_d$ is hydrogen; or
alkyl$_{(C\leq 12)}$, cycloalkyl$_{(C\leq 12)}$, heterocycloalkyl$_{(C\leq 12)}$, aralkyl$_{(C\leq 12)}$, aryl$_{(C\leq 12)}$, heteroaralkyl$_{(C\leq 12)}$, heteroaryl$_{(C\leq 12)}$, or a substituted version of any of these groups; or
a group of the formula:

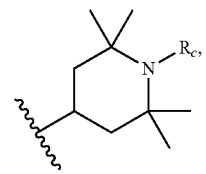

(IIb)

wherein R$_c$ is as defined above; or
a group of the formula:

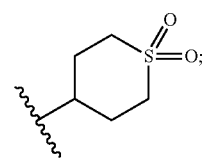

(IIc)

$R_e$ is hydrogen, alkyl$_{(C≤12)}$, or substituted alkyl$_{(C≤12)}$; or a compound of the formula:

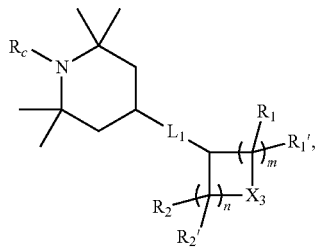
(III)

wherein:
n, m, $X_3$, $R_1$, $R_1'$, $R_2$, $R_2'$, and $R_e$ are as defined above; and
$L_1$ is
a group of the formula:

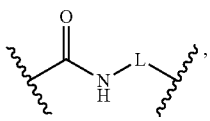
(IIIb)

wherein:
L is a covalent bond; or
a group of the formula:

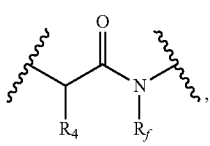
(IIIa)

wherein:
$R_f$ is hydrogen, alkyl$_{(C≤12)}$, or substituted alkyl$_{(C≤12)}$;
$R_4$ is hydrogen; or
alkyl$_{(C≤12)}$, aralkyl$_{(C≤12)}$, heteroaralkyl$_{(C≤12)}$, -alkanediyl$_{(C≤12)}$-ONO$_2$, or a substituted version of any of these groups;
provided the sum of n and m is 1, 2, 3, 4, 5, or 6; or
a compound of the formula:

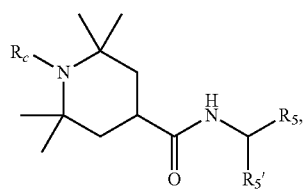
(IV)

wherein:
$R_c$ is as defined above;
$R_5$ is —CO$_2R_g$ or —C(O)NR$_h$R$_i$, wherein:
$R_g$ is hydrogen; or
alkyl$_{(C≤12)}$, substituted alkyl$_{(C≤12)}$, cycloalkyl$_{(C≤12)}$, or substituted cycloalkyl$_{(C≤12)}$;

$R_h$ and $R_i$ are each independently hydrogen; or
alkyl$_{(C≤12)}$, substituted alkyl$_{(C≤12)}$, cycloalkyl$_{(C≤12)}$, or substituted cycloalkyl$_{(C≤12)}$; and
$R_5'$ is hydrogen; or
alkyl$_{(C≤12)}$, aralkyl$_{(C≤12)}$, heteroaralkyl$_{(C≤12)}$, or a substituted version of any of these groups;
or a pharmaceutically acceptable salt of any of these formulae.

3. The compound of claim 1 further defined as:

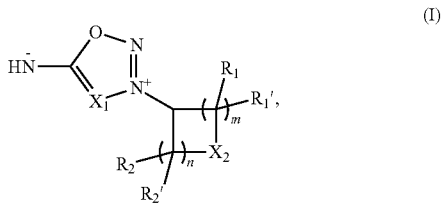
(I)

wherein:
n and m are each independently 0, 1, 2, 3, or 4;
$X_1$ is =CH— or =N—;
$X_2$ is —O—, —S—, —S(O)—, or —S(O)$_2$—;
each instance of $R_1$, $R_1'$, $R_2$, and $R_2'$ is independently hydrogen, hydroxy, amino, nitro, cyano, halo, carboxyl, carbamoyl, mercapto, —S(O)$_2$OH, —S(O)$_2$NH$_2$, alkyl$_{(C≤12)}$, acyl$_{(C≤12)}$, alkoxy$_{(C≤12)}$, alkylamino$_{(C≤12)}$, dialkylamino$_{(C≤12)}$, amido$_{(C≤12)}$, or acyloxy$_{(C≤12)}$, or —C(O)R$_b$, wherein:
$R_b$ alkoxy$_{(C≤12)}$, alkylamino$_{(C≤12)}$, or dialkylamino$_{(C≤12)}$; or
provided the sum of n and m is 1, 2, 3, 4, 5, or 6; or
a compound of the formula:

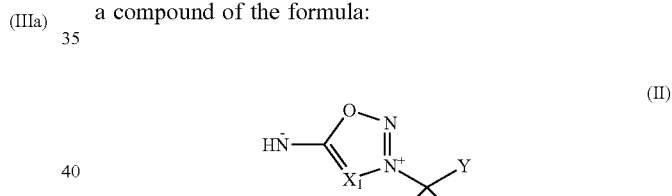
(II)

wherein:
$X_1$ is as defined above;
$R_3$ is alkyl$_{(C2-12)}$, substituted alkyl$_{(C≤12)}$, aralkyl$_{(C≤12)}$, substituted aralkyl$_{(C≤12)}$, heteroaralkyl$_{(C≤12)}$, or -alkanediyl$_{(C≤12)}$-NHC(NH)NH$_2$;
$R_3'$ is hydrogen; or
$R_3$ and $R_3'$ are taken together and are -alkanediyl$_{(C≤12)}$-$X_3$—, substituted -alkanediyl$_{(C≤12)}$-$X_3$—, -alkanediyl$_{(C≤6)}$-$X_3$-alkanediyl$_{(C≤6)}$—, or substituted-alkanediyl$_{(C≤6)}$-$X_3$-alkanediyl$_{(C≤6)}$—, wherein:
$X_3$ is —O—, —NR$_a$—, —S—, —S(O)—, or —S(O)$_2$—, wherein:
$R_a$ is hydrogen, hydroxy, or oxyl radical; or
alkyl$_{(C≤12)}$, aralkyl$_{(C≤12)}$, acyl$_{(C≤12)}$, or a substituted version of any of these groups; or
a group of the formula:

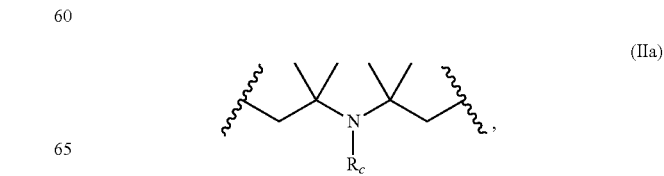
(IIa)

wherein:
R$_c$ is hydroxy or oxyl radical; and
Y is —CO$_2$R$_d$, or —C(O)NR$_d$R$_e$, wherein:
R$_d$ is hydrogen; or
alkyl$_{(C\le12)}$, cycloalkyl$_{(C\le12)}$, heterocycloalkyl$_{(C\le12)}$, aralkyl$_{(C\le12)}$, aryl$_{(C\le12)}$, heteroaralkyl$_{(C\le12)}$, heteroaryl$_{(C\le12)}$, or a substituted version of any of these groups; or
a group of the formula:

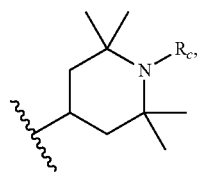
(IIb)

wherein R$_c$ is as defined above;
R$_e$ is hydrogen, alkyl$_{(C\le12)}$, or substituted alkyl$_{(C\le12)}$; or
a compound of the formula:

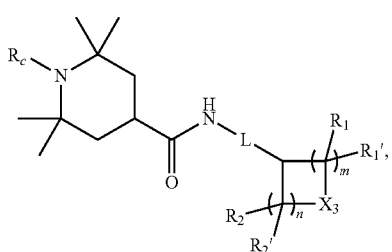
(III)

wherein:
n, m, X$_3$, R$_1$, R$_1$', R$_2$, R$_2$', and R$_c$ are as defined above; and
L is a covalent bond; or
a group of the formula:

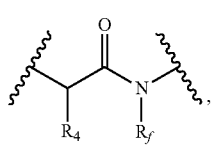
(IIIa)

wherein:
R$_f$ is hydrogen, alkyl$_{(C\le12)}$, or substituted alkyl$_{(C\le12)}$;
R$_4$ is hydrogen; or
alkyl$_{(C\le12)}$, aralkyl$_{(C\le12)}$, heteroaralkyl$_{(C\le12)}$, or a substituted version of any of these groups;
provided the sum of n and m is 1, 2, 3, 4, 5, or 6; or
a compound of the formula:

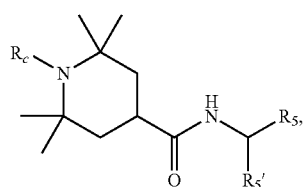
(IV)

wherein:
R$_c$ is as defined above;
R$_5$ is —CO$_2$R$_g$ or —C(O)NR$_h$R$_i$, wherein:
R$_g$ is hydrogen; or
alkyl$_{(C\le12)}$, substituted alkyl$_{(C\le12)}$, cycloalkyl$_{(C\le12)}$, or substituted cycloalkyl$_{(C\le12)}$;
R$_h$ and R$_i$ are each independently hydrogen; or
alkyl$_{(C\le12)}$, substituted alkyl$_{(C\le12)}$, cycloalkyl$_{(C\le12)}$, or substituted cycloalkyl$_{(C\le12)}$; and
R$_5$' is hydrogen; or
alkyl$_{(C\le12)}$, aralkyl$_{(C\le12)}$, heteroaralkyl$_{(C\le12)}$, or a substituted version of any of these groups;
or a pharmaceutically acceptable salt of any of these formulae.

4. The compound of claim 2, wherein the compound is a compound of formula (I).

5. The compound of claim 1, wherein the compound is further defined as:

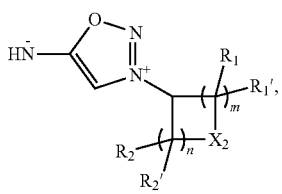
(V)

wherein:
n and m are each independently 0, 1, 2, 3, or 4;
X$_2$ is —O—, —S—, —S(O)—, or —S(O)$_2$—; and
each instance of R$_1$, R$_1$', R$_2$, and R$_2$' is independently hydrogen, hydroxy, amino, nitro, cyano, halo, carboxyl, carbamoyl, mercapto, —S(O)$_2$OH, —S(O)$_2$NH$_2$, alkyl$_{(C\le12)}$, acyl$_{(C\le12)}$, alkoxy$_{(C\le12)}$, alkylamino$_{(C\le12)}$, dialkylamino$_{(C\le12)}$, amido$_{(C\le12)}$, or acyloxy$_{(C\le12)}$, or —C(O)R$_b$, wherein:
R$_b$ alkoxy$_{(C\le12)}$, alkylamino$_{(C\le12)}$, or dialkylamino$_{(C\le12)}$;
provided the sum of n and m is 1, 2, 3, 4, 5, or 6;
or a pharmaceutically acceptable salt thereof.

6. The compound of claim 1, wherein the compound is further defined as:

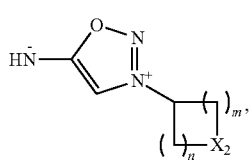
(VI)

wherein:
n and m are each independently 0, 1, 2, 3, or 4; and
X$_2$ is —O—, —S—, —S(O)—, or —S(O)$_2$;
provided the sum of n and m is 1, 2, 3, 4, 5, or 6;
or a pharmaceutically acceptable salt thereof.

7. The compound of claim 1, wherein the compound is further defined as:

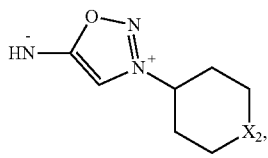

(VII)

wherein:
X₂ is —O—, —S—, —S(O)—, or —S(O)₂—; or a pharmaceutically acceptable salt thereof.

8. The compound of claim 1, wherein X₂ is —S—, —S(O)—, or —S(O)₂—.
9. The compound of claim 1, wherein X₂ is —S— or —S(O)₂—.
10. The compound of claim 1, wherein X₂ is —S—.
11. The compound of claim 1, wherein X₂ is —S(O)₂—.
12. The compound of claim 1, wherein Y is a group of the formula:

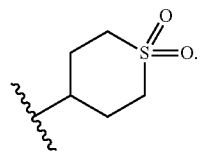

(IIc)

13. The compound of claim 2, wherein the compound is a compound of formula (II).
14. The compound of claim 1, wherein the compound is further defined as:

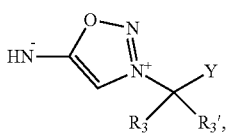

(VIII)

wherein:
$R_3$ is alkyl$_{(C2-12)}$, substituted alkyl$_{(C\le12)}$, aralkyl$_{(C\le12)}$, substituted aralkyl$_{(C\le12)}$, heteroaralkyl$_{(C\le12)}$, or -alkanediyl$_{(C\le12)}$-NHC(NH)NH₂;
$R_3'$ is hydrogen; or
$R_3$ and $R_3'$ are taken together and are -alkanediyl$_{(C\le12)}$-X₃—, substituted -alkanediyl$_{(C\le12)}$-X₃—, -alkanediyl$_{(C\le6)}$-X₃-alkanediyl$_{(C\le6)}$—, or substituted-alkanediyl$_{(C\le6)}$-X₃-alkanediyl$_{(C\le6)}$—, wherein:
X₃ is —O—, —NR$_a$—, —S—, —S(O)—, or —S(O)₂—, wherein:
$R_a$ is hydrogen, hydroxy, or oxyl radical; or alkyl$_{(C\le12)}$, aralkyl$_{(C\le12)}$, acyl$_{(C\le12)}$, or a substituted version of any of these groups; or
a group of the formula:

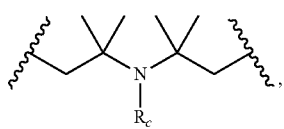

(IIa)

wherein:
$R_c$ is hydroxy or oxyl radical; and
Y is —CO₂R$_d$, or —C(O)NR$_d$R$_e$, wherein:
$R_d$ is hydrogen; or
alkyl$_{(C\le12)}$, cycloalkyl$_{(C\le12)}$, heterocycloalkyl$_{(C\le12)}$, aralkyl$_{(C\le12)}$, aryl$_{(C\le12)}$, heteroaralkyl$_{(C\le12)}$, heteroaryl$_{(C\le12)}$, or a substituted version of any of these groups; or
a group of the formula:

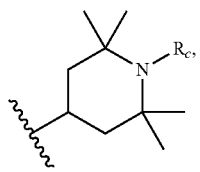

(IIb)

wherein $R_c$ is hydroxy or oxyl radical;
$R_e$ is hydrogen, alkyl$_{(C\le12)}$, or substituted alkyl$_{(C\le12)}$;
or a pharmaceutically acceptable salt thereof.

15. The compound of claim 1, wherein the compound is further defined as:

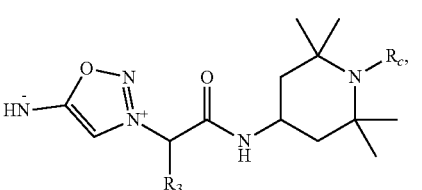

(IX)

wherein:
$R_3$ is alkyl$_{(C2-12)}$, substituted alkyl$_{(C\le12)}$, aralkyl$_{(C\le12)}$, substituted aralkyl$_{(C\le12)}$, heteroaralkyl$_{(C\le12)}$, or -alkanediyl$_{(C\le12)}$-NHC(NH)NH₂; and
$R_c$ is hydroxy or oxyl radical;
or a pharmaceutically acceptable salt thereof.

16. The compound of claim 1, wherein $R_3$ is alkyl$_{(C2-12)}$ or substituted alkyl$_{(C\le12)}$.
17. The compound of claim 1, wherein $R_3$ is substituted alkyl$_{(C\le12)}$.
18. The compound of claim 1, wherein $R_3$ is —CH₂CH₂SCH₃.
19. The compound of claim 1, wherein $R_3$ is aralkyl$_{(C\le12)}$ or substituted aralkyl$_{(C\le12)}$.
20. The compound of claim 1, wherein $R_3$ is aralkyl$_{(C\le12)}$.
21. The compound of claim 1, wherein $R_3$ is benzyl.
22. The compound of claim 1, wherein $R_3$ is substituted aralkyl$_{(C\le12)}$.
23. The compound of claim 1, wherein $R_3$ is p-hydroxybenzyl.
24. The compound of claim 1, wherein $R_c$ is hydroxy.
25. The compound of claim 1, wherein $R_c$ is oxyl radical.
26. The compound of claim 1, wherein the compound is a compound of formula (III).

27. The compound of claim 1, wherein $L_1$ is a group of the formula:

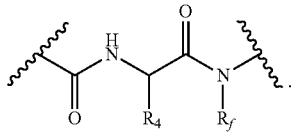

28. The compound of claim 1, wherein the compound is further defined as:

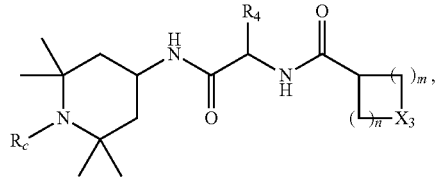

(XII)

wherein:
n and m are each independently 0, 1, 2, 3, or 4;
$X_3$ is —O—, —NR$_a$—, —S—, —S(O)—, or —S(O)$_2$—, wherein:
$R_a$ is hydrogen, hydroxy, or oxyl radical; or
alkyl$_{(C≤12)}$, aralkyl$_{(C≤12)}$, acyl$_{(C≤12)}$, or a substituted version of any of these groups;
$R_c$ is hydroxy or oxyl radical; and
$R_4$ is hydrogen; or
alkyl$_{(C≤12)}$, aralkyl$_{(C≤12)}$, heteroaralkyl$_{(C≤12)}$, -alkanediyl$_{(C≤12)}$-ONO$_2$, or a substituted version of any of these groups;
provided the sum of n and m is 1, 2, 3, 4, 5, or 6;
or a pharmaceutically acceptable salt thereof.

29. The compound of claim 1, wherein the compound is further defined as:

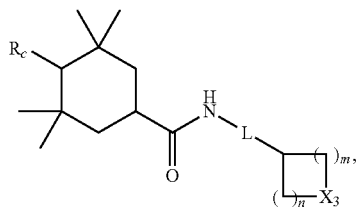

(X)

wherein:
n and m are each independently 0, 1, 2, 3, or 4;
$X_3$ is —O—, —NR$_2$—, —S—, —S(O)—, or —S(O)$_2$—, wherein:
$R_a$ is hydrogen, hydroxy, or oxyl radical; or
alkyl$_{(C≤12)}$, aralkyl$_{(C≤12)}$, acyl$_{(C≤12)}$, or a substituted version of any of these groups;
$R_c$ is hydroxy or oxyl radical; and
L is a covalent bond; or
a group of the formula:

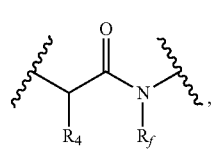

(IIIa)

wherein:
$R_f$ is hydrogen, alkyl$_{(C≤12)}$, or substituted alkyl$_{(C≤12)}$;
$R_4$ is hydrogen; or
alkyl$_{(C≤12)}$, aralkyl$_{(C≤12)}$, heteroaralkyl$_{(C≤12)}$, or a substituted version of any of these groups;
provided the sum of n and m is 1, 2, 3, 4, 5, or 6;
or a pharmaceutically acceptable salt thereof.

30. The compound of claim 1, wherein the compound is further defined as:

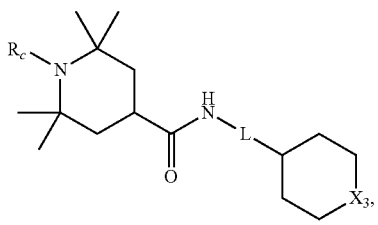

(XI)

wherein:
$X_3$ is —O—, —NR$_a$—, —S—, —S(O)—, or —S(O)$_2$—, wherein:
$R_a$ is hydrogen, hydroxy, or oxyl radical; or
alkyl$_{(C≤12)}$, aralkyl$_{(C≤12)}$, acyl$_{(C≤12)}$, or a substituted version of any of these groups; $R_c$ is hydroxy or oxyl radical; and
L is a covalent bond; or
a group of the formula:

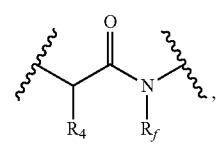

(IIIa)

wherein:
$R_f$ is hydrogen, alkyl$_{(C≤12)}$, or substituted alkyl$_{(C≤12)}$;
$R_4$ is hydrogen; or
alkyl$_{(C≤12)}$, aralkyl$_{(C≤12)}$, heteroaralkyl$_{(C≤12)}$, or a substituted version of any of these groups;
or a pharmaceutically acceptable salt thereof.

31. The compound of claim 1, wherein $X_3$ is —S—, —S(O)—, or —S(O)$_2$—.

32. The compound of claim 1, wherein $X_3$ is —S— or —S(O)$_2$—.

33. The compound of claim 1, wherein $X_3$ is —S—.

34. The compound of claim 1, wherein $X_3$ is —S(O)$_2$—.

35. The compound of claim 1, wherein $R_f$ is hydrogen.

36. The compound of claim 1, wherein $R_4$ is alkyl$_{(C≤12)}$, substituted alkyl$_{(C≤12)}$, aralkyl$_{(C≤12)}$, or substituted aralkyl$_{(C≤12)}$.

37. The compound of claim 1, wherein $R_4$ is alkyl$_{(C≤12)}$ or substituted alkyl$_{(C≤12)}$.

38. The compound of claim 1, wherein $R_4$ is substituted alkyl$_{(C≤12)}$.

39. The compound of claim 1, wherein $R_4$ is —CH$_2$CH$_2$SCH$_3$.

40. The compound of claim 1, wherein $R_4$ is aralkyl$_{(C≤12)}$, or substituted aralkyl$_{(C≤12)}$.

41. The compound of claim 1, wherein $R_4$ is substituted aralkyl$_{(C≤12)}$.

42. The compound of claim 1, wherein $R_4$ is 4-hydroxybenzyl.

43. The compound of claim 1, wherein $R_4$ is -alkanediyl$_{(C \leq 12)}$-ONO$_2$ or substituted-alkanediyl$_{(C \leq 12)}$-ONO$_2$.

44. The compound of claim 43, wherein $R_4$ is -alkanediyl$_{(C \leq 12)}$-ONO$_2$.

45. The compound of claim 44, wherein $R_4$ is -ethanediyl-ONO$_2$.

46. The compound of claim 1, wherein L is a covalent bond.

47. The compound of claim 28, wherein $R_c$ is hydroxy.

48. The compound of claim 28, wherein $R_c$ is oxyl radical.

49. The compound of claim 1, wherein the compound is a compound of formula (IV).

50. The compound of claim 1, wherein the compound is further defined as:

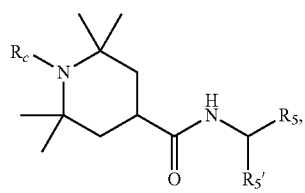

(IV)

wherein:
  $R_c$ is hydroxy or oxyl radical;
  $R_5$ is —CO$_2$R$_g$, wherein:
    $R_g$ is hydrogen; or
      alkyl$_{(C \leq 12)}$, substituted alkyl$_{(C \leq 12)}$, cycloalkyl$_{(C \leq 12)}$, or substituted cycloalkyl$_{(C \leq 12)}$; and
  $R_5'$ is hydrogen; or
    alkyl$_{(C \leq 12)}$, aralkyl$_{(C \leq 12)}$, heteroaralkyl$_{(C \leq 12)}$, or a substituted version of any of these groups;
or a pharmaceutically acceptable salt thereof.

51. The compound of claim 1, wherein $R_g$ is alkyl$_{(C \leq 12)}$.

52. The compound of claim 1, wherein $R_g$ is methyl.

53. The compound of claim 1, wherein $R_5'$ is alkyl$_{(C \leq 12)}$ or substituted alkyl$_{(C \leq 12)}$.

54. The compound of claim 1, wherein $R_5'$ is substituted alkyl$_{(C \leq 12)}$.

55. The compound of claim 1, wherein $R_5'$ is —CH$_2$CH$_2$SCH$_3$.

56. The compound of claim 50, wherein $R_c$ is hydroxy.

57. The compound of claim 50, wherein $R_c$ is oxyl radical.

58. The compound of claim 1, wherein the compound is further defined as:

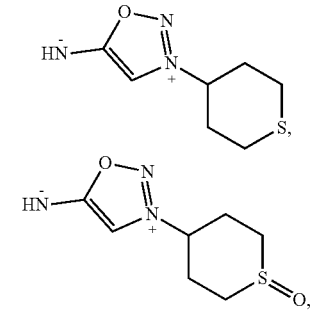

-continued

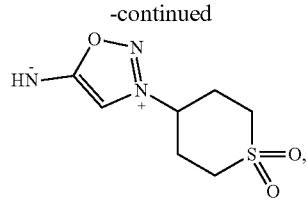

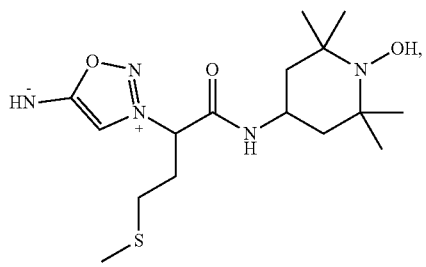

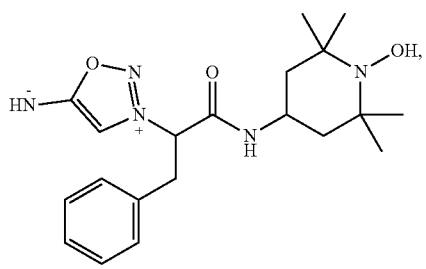

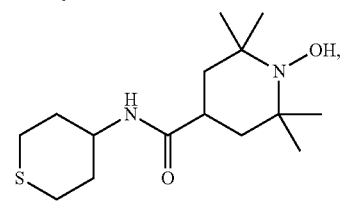

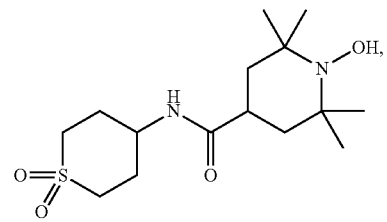

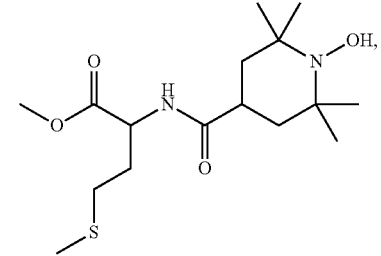

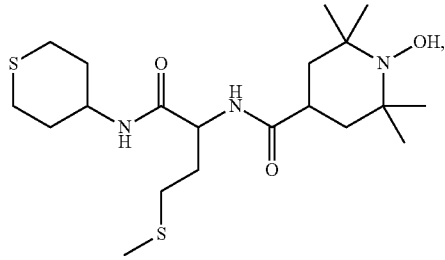

79
-continued
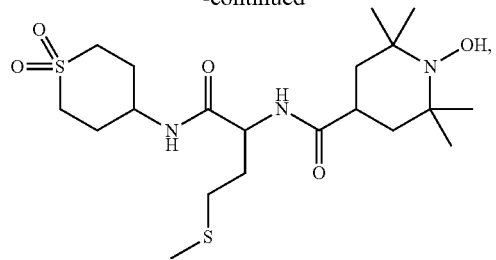
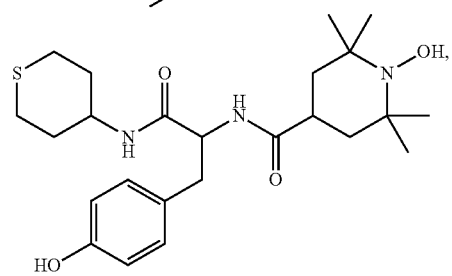
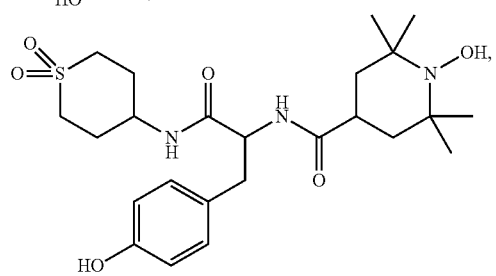
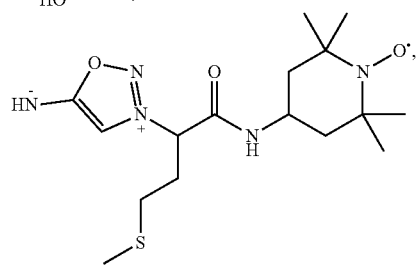
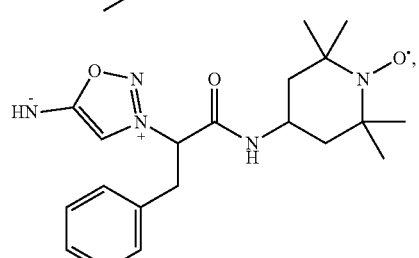
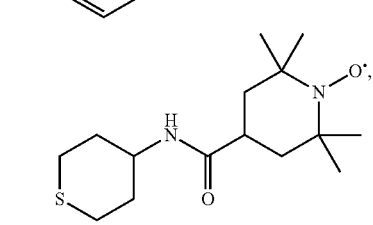
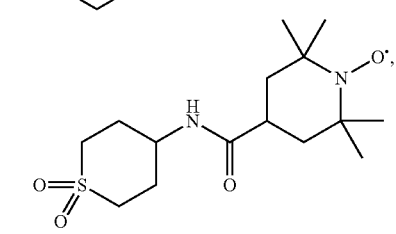
80
-continued
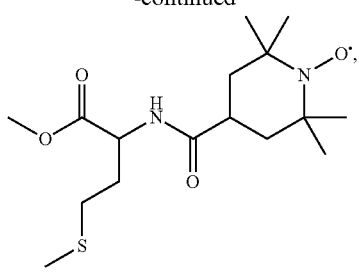
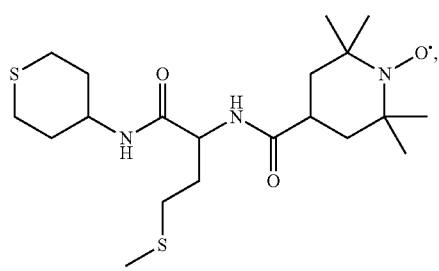
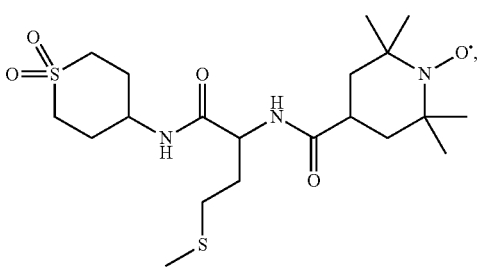
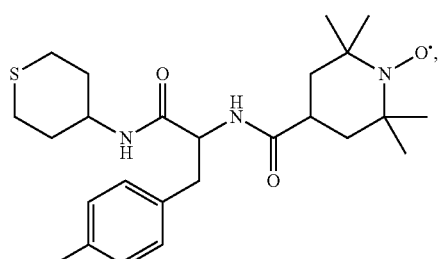
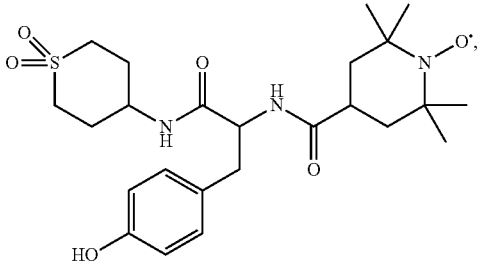
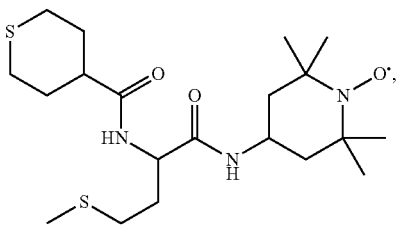

-continued
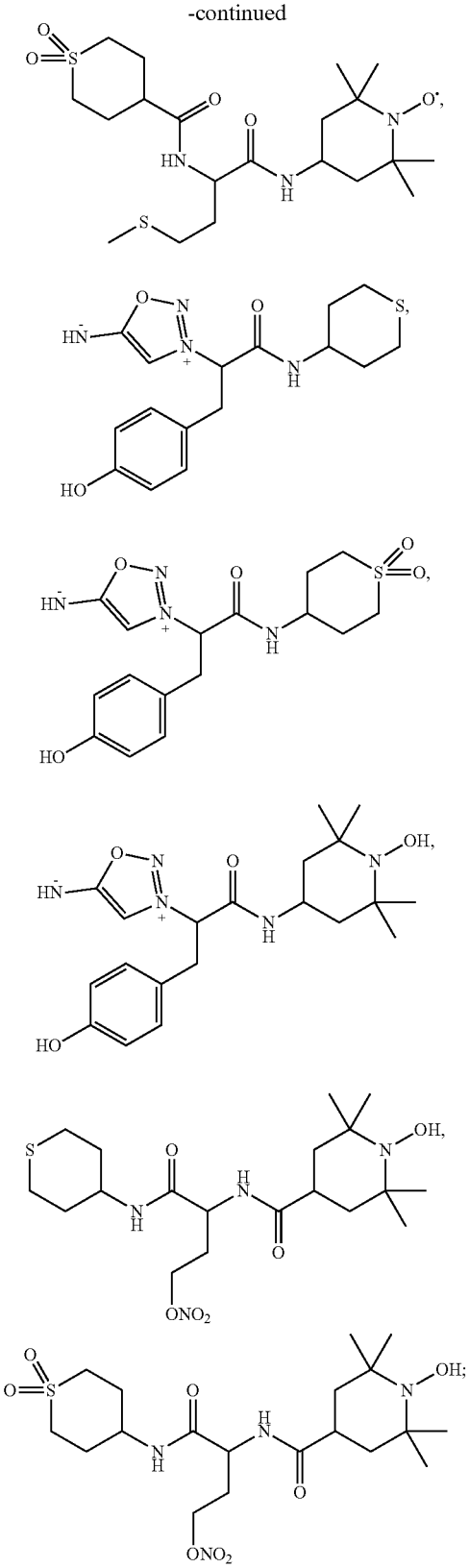
or a pharmaceutically acceptable salt thereof.
59. The compound of claim 1, wherein the compound is further defined as:
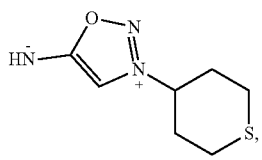
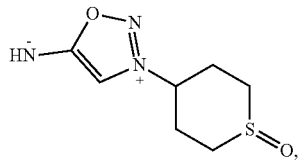
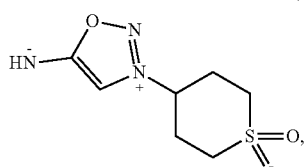
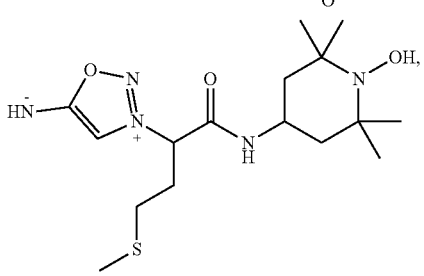
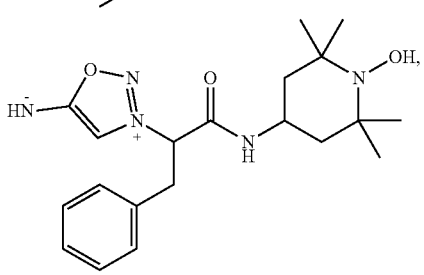
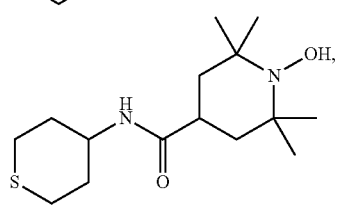
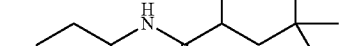
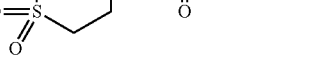
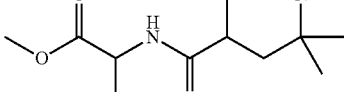
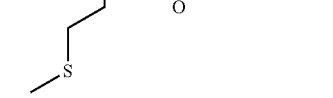

83
-continued
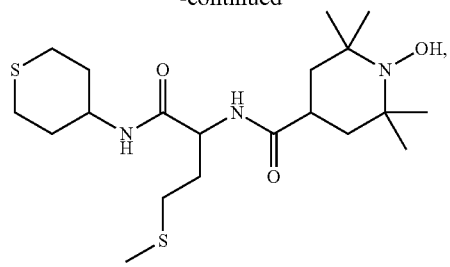
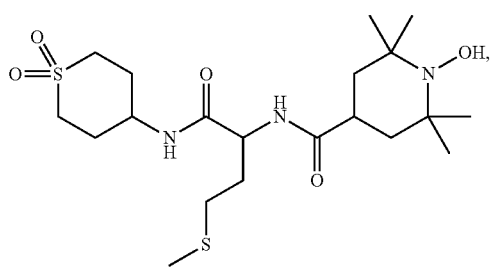
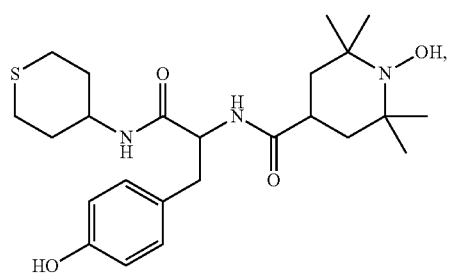
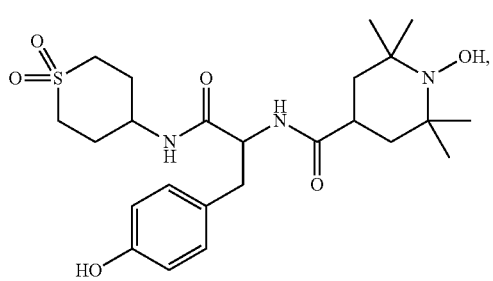
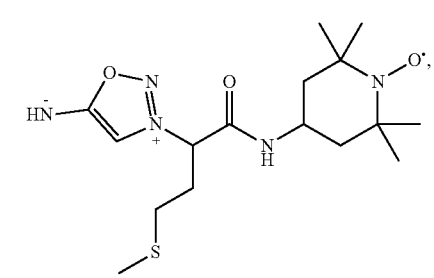
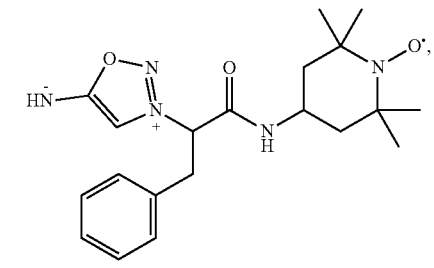
84
-continued
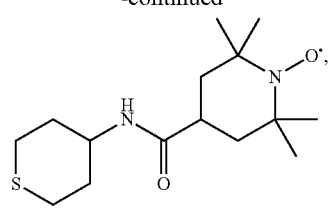
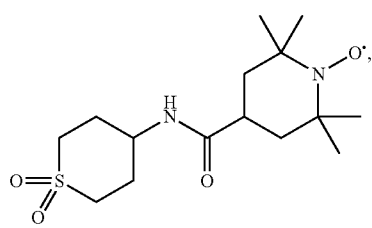
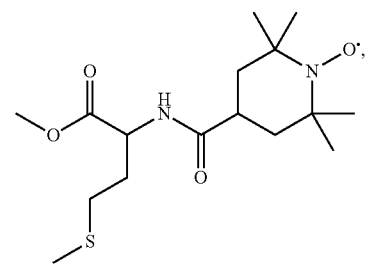
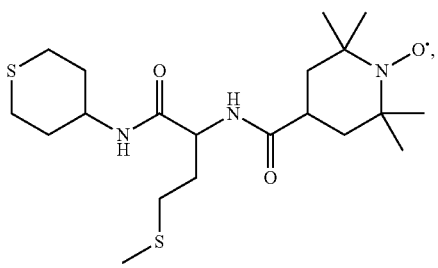
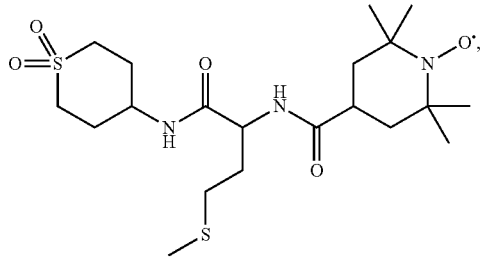
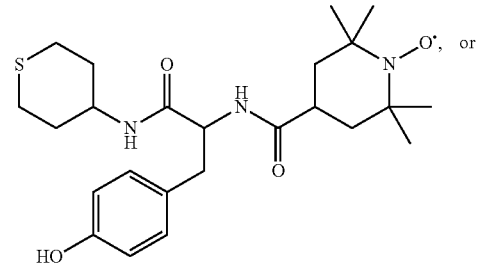

or a pharmaceutically acceptable salt thereof.

60. The compound of claim 1, wherein the compound is further defined as:

or a pharmaceutically acceptable salt thereof.

61. A pharmaceutical composition comprising:
a) a compound of claim 1; and
b) an excipient and/or a pharmaceutically acceptable carrier.

62. The pharmaceutical composition of claim 61, wherein the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion.

63. The pharmaceutical composition of claim 61, wherein the compound is:

or

64. The pharmaceutical composition of claim 61, wherein the compound is formulated as a nanoparticle.

65. The pharmaceutical composition of claim 61, wherein the composition comprises PLGA.

66. A method of treating a disease or disorder, wherein the disease or disorder is ischemia, ischemia/reperfusion injury, ischemic neuropathy, glaucoma, glaucomatous optic neuropathy, neuroinflammation, age-related macular degeneration, diabetic retinopathy, pulmonary arterial disease, peripheral arterial diseases, atherosclerosis, angina pectoris, or high blood pressure in a patient in need thereof comprising administering to the patient a therapeutically effective amount of a compound of claim 1.

67. The method of claim 66, wherein the patient is a mammal.

68. The method of claim 66, wherein the patient is a human.

69. The method of claim 66, wherein the disease is an eye disease, wherein the eye disease is glaucoma, glaucomatous optic neuropathy, age-related macular degeneration, or diabetic retinopathy.

70. The method of claim 66, wherein the disease or disorder is ischemia, ischemia/reperfusion injury, ischemic neuropathy, neuroinflammation, pulmonary arterial disease, peripheral arterial diseases, atherosclerosis, angina pectoris, or high blood pressure.

71. The method of claim 66, wherein the disease or disorder is ischemia/reperfusion injury.

72. The method of claim 66, wherein the disease or disorder is the result of an ischemic event.

73. The method of claim 72, wherein the ischemic event occurred less than 48 hours before administering.

74. The method of claim 72, wherein the ischemic event occurred less than 24 hours before administering.

75. The method of claim 72, wherein the ischemic event occurred less than 12 hours before administering.

76. The method of claim 72, wherein the ischemic event occurred less than 6 hours before administering.

77. The method of claim 66, wherein the compound or composition is formulated as a nanoparticle.

78. The method of claim 77, wherein the nanoparticle comprises PLGA.

* * * * *

UNITED STATES PATENT AND TRADEMARK OFFICE
CERTIFICATE OF CORRECTION

PATENT NO. : 12,234,228 B2  
APPLICATION NO. : 17/416278  
DATED : February 25, 2025  
INVENTOR(S) : Suchismita Acharya Page 1 of 1

It is certified that error appears in the above-identified patent and that said Letters Patent is hereby corrected as shown below:

In the Claims

In Claim 1, Column 67, Line 24, delete "$R_b$" and insert -- $R_h$ -- therefor.

In Claim 2, Column 69, Line 18, delete "$R_c$" and insert -- $R_e$ -- therefor.

Signed and Sealed this  
Twenty-third Day of September, 2025

John A. Squires  
*Director of the United States Patent and Trademark Office*